US008722052B2

(12) United States Patent
Bowie et al.

(10) Patent No.: US 8,722,052 B2
(45) Date of Patent: May 13, 2014

(54) VACCINIA VIRUS PROTEIN A46 PEPTIDE AND USE THEREOF

(75) Inventors: Andrew Graham Bowie, Dublin (IE); Barry Noel Harrington, Dublin (IE); Tatyana Sergeevna Lysakova, Kildare (IE); Brian Keogh, Dublin (IE)

(73) Assignee: The Provost, Fellows, Foundation Scholars, and the other members of Board, of the College of the Holy and Undivided Trinity of Queen Elizabeth, near Dublin, Dublin (IE)

( * ) Notice: Subject to any disclaimer, the term of this patent is extended or adjusted under 35 U.S.C. 154(b) by 24 days.

(21) Appl. No.: 13/129,657

(22) PCT Filed: Nov. 17, 2009

(86) PCT No.: PCT/IE2009/000080
§ 371 (c)(1),
(2), (4) Date: May 17, 2011

(87) PCT Pub. No.: WO2010/055500
PCT Pub. Date: May 20, 2010

(65) Prior Publication Data
US 2011/0293641 A1 Dec. 1, 2011

Related U.S. Application Data

(60) Provisional application No. 61/193,319, filed on Nov. 17, 2008.

(51) Int. Cl.
*A61K 39/12* (2006.01)
*A61K 39/275* (2006.01)
*A61K 39/08* (2006.01)
*C12N 7/04* (2006.01)

(52) U.S. Cl.
USPC ............ 424/184.1; 424/186.1; 424/199.1; 424/204.1; 424/232.1; 435/235.1; 435/236; 514/1.1; 514/21.6

(58) Field of Classification Search
None
See application file for complete search history.

(56) References Cited

U.S. PATENT DOCUMENTS

| 3,773,919 | A | 11/1973 | Boswell | |
|---|---|---|---|---|
| 2002/0192217 | A1* | 12/2002 | Calandra et al. | 424/145.1 |
| 2005/0163805 | A1* | 7/2005 | O'Neill et al. | 424/232.1 |

FOREIGN PATENT DOCUMENTS

| EP | 0 058 481 | 8/1982 |
|---|---|---|
| WO | 2004/031225 | 4/2004 |
| WO | 2005/117975 | 12/2005 |

OTHER PUBLICATIONS

Jones et al. 2005 (Characterization of cell-penetrating peptide-mediated delivery; British Journal of Pharmacology, 145:1093-1102).*

Luke A.J. O'Neill, "Targeting Signal transduction as a strategy to treat inflammatory diseases," Nature Reviews: Drug Discovery, http://www.nature.com/reviews/drugdisc, Jun. 9, 2006, pp. 1-15.
Mary T. Harte et al., "The Poxvirus Protein A52R Targets Toll-like Receptor Signaling Complexes to Suppress Host Defense," J. Exp. Med, Feb. 3, 2003, vol. 197, No. 3, pp. 343-351.
Sinead E. Keating et al., "IRAK-2 Participates in Multiple Toll-like Receptor Signaling Pathways to NF$_\kappa$B via Activation of TRAF6 Ubiquitination," The Journal of Biological Chemistry, Nov. 16, 2007, vol. 282, No. 46, pp. 33435-33443.
Sharon L. McCoy et al., "Identification of a Peptide Derived from Vaccinia Virus A52R Protein That Inhibits Cytokine Secretion in Response to TLR-Dependent Signaling and Reduces In Vivo Bacterial-Induced Inflammation," The Journal of Immunology, 2005, pp. 3006-3014.
Paul A. Wender et al., "The design, synthesis, and evaluation of molecules that enable or enhance cellular uptake: Peptoid molecular transporters," PNAS, Nov. 21, 2000, vol. 97, No. 24, pp. 13003-13008.
Luke A.J. O'Neill et al., "The family of five: TIR-domain-containing adaptors in Toll-like receptor signaling," Nature Reviews: Immunology, May 2007, vol. 7, pp. 353-364.
Vladimir U. Toshchakov et al., "Differential Involvement of BB Loops of Toll-IL-1 Resistance (TIR) Domain-Containing Adapter Proteins in TLR4-versus TLR2-Mediated Signal Transduction," The Journal of Immunology, 2005, pp. 494-500.
Vladimir Y. Toshchakov et al., "Cutting Edge: Differential Inhibition of TLR Signaling Pathways by Cell-Permeable Peptides Representing BB Loops of TLRs," Journal of Immunology, 2007, pp. 2655-2660.
Allan Tsung et al., "A Novel Inhibitory Peptide of Toll-like Receptor Signaling Limits Lipopolysaccharide-Induced Production of Inflammatory Mediators and Enhances Survival in Mice," Shock, 2007, vol. 27, No. 4, pp. 364-369.
Shizuo Akira et al., "Pathogen Recognition and Innate Immunity," Cell, Feb. 24, 2006, vol. 124, pp. 783-801.
Andrew Bowie et al., "A46R and A52R from vaccinia virus are antagonists of host IL-1 and toll-like receptor signaling," PNAS, Aug. 29, 2000, vol. 97, No. 18, pp. 10162-10167.
Rajagopal N. Aravalli et al., "Inhibition of Toll-like Receptor Signaling in Primary Murine Microglia," J. Neuroimmune Pharmacol., Nov. 1, 2007, 7 pages.
Loyd V. Allen Jr. et al., Edition, Lippincott Williams *Ansel's Pharmaceutical Dosage Forms and Drug Delivery Systems: Eighth Edition*, Lippincott Williams & Wilkins Publishing, Jan. 1, 2005, Chapters 7, 8, 14, 15 and 20, pp. 204-259, 427-459, and 652-671.
D. Tisch-Idelson et al., "Structure-function relationship in the interaction of mastoparan analogs with neutrophil NADPH oxidase," Biochemical Pharmacology, 2001, vol. 61, pp. 1063-1071.
J. Stack et al., "Vaccinia virus protein A46R targets multiple Toll-like-interleukin-1 receptor adaptors and contributes to virulence," The Journal of Experimental Medicine, Mar. 21, 2005, vol. 201, No. 6, pp. 1007-1018.
Database UniProt (Online), "SubName: Full=Putative uncharacterized protein," XP002570997, Sep. 19, 2006, retrieved from EBI accession No. UNIPROT:QONP39.
L. V. Allen, Jr., "Ansel's Pharmaceutical Dosage Forms and Drug Delivery Systems: Eighth Edition," Aug. 2004, published by Lippincott Williams & Wilkins, pp. 204-259, 426-459, and 652-671.

(Continued)

*Primary Examiner* — Ja'na Hines
*Assistant Examiner* — Mary Lyons
(74) *Attorney, Agent, or Firm* — Jacobson Holman PLLC

(57) ABSTRACT

A peptide for inhibiting Toll-like receptor 4 (TLR4) signalling comprising the amino acid sequence of SEQ ID NO. 4, SEQ ID NO 55, SEQ ID NO 68, SEQ ID NO. 69, SEQ ID NO 70, SEQ ID NO 71, SEQ ID NO 72, SEQ ID NO 79, SEQ ID NO 82, SEQ ID NO 85, SEQ ID NO 88, SEQ ID NO 91, SEQ ID NO 94, SEQ ID NO 97, SEQ ID NO 100, SEQ ID NO 103, SEQ ID NO 106, SEQ ID NO 109, SEQ ID NO 112, or SEQ ID NO 115. The peptide may comprise a delivery sequence such as a cationic peptide.

9 Claims, 30 Drawing Sheets

(56) References Cited

OTHER PUBLICATIONS

K. De Filippo et al., "Neutrophil Chemokines KC and Macrophage-Inflammatory Protein-2 Are Newly Synthesized by Tissue Macrophages Using Distinct TLR Signaling Pathways," The Journal of Immunology, 2008, vol. 180, pp. 4308-4315.

I. Domart-Coulon et al., "Cytotoxicity Assessment of Antibiofouling Compounds and By-products in Marine Bivalve Cell Cultures," Toxicology in Vitro, 2000, vol. 14, pp. 245-251.

K. B. Gorden et al., "Synthetic TLR Agonists Reveal Functional Difference between Human TLR7 and TLR8," Journal of Immunology, 2005, vol. 174, pp. 1259-1268.

P. Henneke et al., "Cellular Activation, Phagocytosis, and Bactericidal Activity Against Group B Streptococcus Involve Parallel Myeloid Differentiation Factor 88-Dependent and Independent Signaling Pathways," Journal of Immunology, 2002, pp. 3970-3977.

Y. Imai et al., "Identification of Oxidative Stress and Toll-like Receptor 4 Signaling as a Key Pathway of Acute Lung Injury," Cell, Apr. 18, 2008, vol. 133, pp. 235-249.

H. Kanzler et al., "Therapeutic targeting of innate immunity with Toll-like receptor agonists and antagonists," Nature Medicine, May 2007, vol. 13, No. 5, pp. 552-559.

Krappmann D. et al., "Regulation of NF-kappa B activity by I kappa B alpha and I kappa B beta stability," Immunobiology, Dec. 1997, vol. 198, pp. 3-13, abstract only.

S. Kumar et al., "P38 Map Kinases: Key Signalling Molecules as Therapeutic Targets for Inflammatory Diseases," Nature Reviews: Drug Discovery, Sep. 2003, vol. 2, pp. 717-726.

R. Langer et al., "Biocompatibility of polymeric delivery systems for macromolecules," Journal of Biomedical Materials Research, 1981, vol. 15, pp. 267-277.

E. Latz et al., "TLR9 signals after translocating from the ER to CpG DNA in the lysosome," Feb. 2004, vol. 5, No. 2, pp. 190-198.

M. Loiarro et al., "Peptide-mediated Interference of TIR Domain Dimerization in MyD88 Inhibits Interleukin-1-dependent Activation of NF-κB," The Journal of Biological Chemistry, Apr. 22, 2005, vol. 280, No. 16, pp. 15809-15814.

E. Lolis et al., "Therapeutic Approaches to Innate Immunity: Severe Sepsis and Septic Shock," Nature Reviews: Drug Discovery, Aug. 2003, vol. 2, pp. 635-645.

K. S. Michelsen et al., "Lack of Toll-Like Receptor 4 or Myeloid Differentiation Factor 88 Reduces Atherosclerosis and Alters Plaque Phenotype in Mice Deficient in Agolipoprotein E," Proceedings of the National Academy of Sciences of the United States of America, Jul. 20, 2004, vol. 101, No. 29, pp. 10679-10684.

C. L. Murriel et al., "Influence of protein transduction domains on intracellular delivery of macromolecules," Expert Opinion Drug Delivery, 2006, vol. 3, No. 6, pp. 739-746.

S. R. Schwarze et al., "In Vivo Protein Transduction: Delivery of a Biologically Active Protein into the Mouse," Science, Sep. 3, 1999, vol. 285, Issue 5433, pp. 1569-1572.

K. R. Sidman et al., "Controlled Release of Macromolecules and Pharmaceuticals from Synthetic Polypeptides Based on Glutamic Acid," Biopolymers, 1983, vol. 22, pp. 547-556.

S. Takashiba et al., "Differentiation of Monocytes to Macrophages Primes Cells for Lipopolysaccharide Stimulation via Accumulation of Cytoplasmic Nuclear Factor κB," Infection and Immunity, Nov. 1999, vol. 67, No. 11, pp. 5573-5578.

Sung-Chun Tang et al., "Pivotal Role for Neuronal Toll-Like Receptors in Ischemic Brain Injury and Functional Deficits," Proceedings of the National Academy of Sciences of the United States of America, Aug. 21, 2007, vol. 104, No. 34, pp. 13798-13803.

V. Y. Toshchakov et al., "Cell-penetrating TIR BB loop decoy peptides: a novel class of TLR signaling inhibitors and a tool to study topology of TIR-TIR interactions," Expert Opinion Biological Therapy, 2007, vol. 7, No. 7, pp. 1035-1050.

T. Vogl et al., "Mrp8 and Mrp14 are endogenous activators of Toll-like receptor 4, promoting lethal, endotoxin-induced shock," Nature Medicine, Sep. 2007, vol. 13, No. 9, pp. 1042-1049.

H. Wu et al., "TLR4 activation mediated kidney ischemia/reperfusion injury," The Journal of Clinical Investigation, Oct. 2007, vol. 117, No. 10, pp. 2847-2859.

Y. Zhai et al., "Cutting Edge: TLR4 Activation Mediates Liver Ischemia/Reperfusion Inflammatory Response via IFN Regulatory Factor 3-Dependent MyD88-Independent Parkway," Journal of Immunology, 2004, vol. 173, pp. 7115-7119.

\* cited by examiner

A.

B.

A.

LPS 10ng/ml

B.

C.

SEQUENCE LISTING

```
<160> NUMBER OF SEQ ID NOS: 117

<210> SEQ ID NO 1
<211> LENGTH: 11
<212> TYPE: PRT
<213> ORGANISM: Vaccinia Virus

<400> SEQUENCE: 1

Glu Cys Ala Val Asn Thr Pro Val Ser Met Thr
1               5                   10

<210> SEQ ID NO 2
<211> LENGTH: 11
<212> TYPE: PRT
<213> ORGANISM: Vaccinia Virus

<400> SEQUENCE: 2

Thr Pro Val Ser Met Thr Tyr Leu Tyr Asn Lys
1               5                   10

<210> SEQ ID NO 3
<211> LENGTH: 11
<212> TYPE: PRT
<213> ORGANISM: Vaccinia Virus

<400> SEQUENCE: 3

Thr Tyr Leu Tyr Asn Lys Tyr Ser Phe Lys Leu
1               5                   10

<210> SEQ ID NO 4
<211> LENGTH: 11
<212> TYPE: PRT
<213> ORGANISM: Vaccinia Virus

<400> SEQUENCE: 4

Lys Tyr Ser Phe Lys Leu Ile Leu Ala Glu Tyr
1               5                   10

<210> SEQ ID NO 5
<211> LENGTH: 11
<212> TYPE: PRT
<213> ORGANISM: Vaccinia Virus

<400> SEQUENCE: 5

Leu Ile Leu Ala Glu Tyr Ile Arg His Arg Asn
1               5                   10

<210> SEQ ID NO 6
<211> LENGTH: 11
<212> TYPE: PRT
<213> ORGANISM: Vaccinia Virus

<400> SEQUENCE: 6

Tyr Ile Arg His Arg Asn Thr Ile Ser Gly Asn
1               5                   10

<210> SEQ ID NO 7
```

```
<211> LENGTH: 11
<212> TYPE: PRT
<213> ORGANISM: Vaccinia Virus

<400> SEQUENCE: 7

Arg Asn Thr Ile Ser Gly Asn Ile Tyr Ser Ala
1               5                   10

<210> SEQ ID NO 8
<211> LENGTH: 11
<212> TYPE: PRT
<213> ORGANISM: Vaccinia Virus

<400> SEQUENCE: 8

Gly Asn Ile Tyr Ser Ala Leu Met Thr Leu Asp
1               5                   10

<210> SEQ ID NO 9
<211> LENGTH: 11
<212> TYPE: PRT
<213> ORGANISM: Vaccinia Virus

<400> SEQUENCE: 9

Asp Ser Gly Leu Phe Asp Phe Val Asn Phe Val
1               5                   10

<210> SEQ ID NO 10
<211> LENGTH: 11
<212> TYPE: PRT
<213> ORGANISM: Vaccinia Virus

<400> SEQUENCE: 10

Asp Phe Val Asn Phe Val Lys Asp Met Ile Cys
1               5                   10

<210> SEQ ID NO 11
<211> LENGTH: 11
<212> TYPE: PRT
<213> ORGANISM: Vaccinia Virus

<400> SEQUENCE: 11

Val Lys Asp Met Ile Cys Cys Asp Ser Arg Ile
1               5                   10

<210> SEQ ID NO 12
<211> LENGTH: 11
<212> TYPE: PRT
<213> ORGANISM: Vaccinia Virus

<400> SEQUENCE: 12

Asp Ser Arg Ile Val Val Ala Leu Ser Ser Leu
1               5                   10

<210> SEQ ID NO 13
<211> LENGTH: 11
<212> TYPE: PRT
<213> ORGANISM: Vaccinia Virus

<400> SEQUENCE: 13

Val Ala Leu Ser Ser Leu Val Ser Lys His Trp
1               5                   10

<210> SEQ ID NO 14
<211> LENGTH: 11
<212> TYPE: PRT
<213> ORGANISM: Vaccinia Virus
```

```
<400> SEQUENCE: 14

Leu Val Ser Lys His Trp Glu Leu Thr Asn Lys
1               5                   10

<210> SEQ ID NO 15
<211> LENGTH: 11
<212> TYPE: PRT
<213> ORGANISM: Vaccinia Virus

<400> SEQUENCE: 15

Glu Leu Thr Asn Lys Lys Tyr Arg Cys Met Ala
1               5                   10

<210> SEQ ID NO 16
<211> LENGTH: 169
<212> TYPE: PRT
<213> ORGANISM: Vaccinia Virus

<400> SEQUENCE: 16

Ile Gly Cys Ala Val Asn Thr Pro Val Ser Met Thr Tyr Leu Tyr Asn
1               5                   10                  15

Lys Tyr Ser Phe Lys Leu Ile Leu Ala Glu Tyr Ile Arg His Arg Asn
                20                  25                  30

Thr Ile Ser Gly Asn Ile Tyr Ser Ala Leu Met Thr Leu Asp Asp Leu
            35                  40                  45

Ala Ile Lys Gln Tyr Gly Asp Ile Asp Leu Leu Phe Asn Glu Lys Leu
        50                  55                  60

Lys Val Asp Ser Asp Ser Gly Leu Phe Asp Phe Val Asn Phe Val Lys
65                  70                  75                  80

Asp Met Ile Cys Cys Asp Ser Arg Ile Val Val Ala Leu Ser Ser Leu
                85                  90                  95

Val Ser Lys His Trp Glu Leu Thr Asn Lys Lys Tyr Arg Cys Met Ala
                100                 105                 110

Leu Ala Glu His Ile Ser Asp Ser Ile Pro Ile Ser Glu Leu Ser Arg
            115                 120                 125

Leu Arg Tyr Asn Leu Cys Lys Tyr Leu Arg Gly His Thr Glu Ser Ile
        130                 135                 140

Glu Asp Lys Phe Asp Tyr Phe Glu Asp Asp Ser Ser Thr Cys Ser
145                 150                 155                 160

Ala Val Thr Asp Arg Glu Thr Asp Val
                165

<210> SEQ ID NO 17
<211> LENGTH: 20
<212> TYPE: PRT
<213> ORGANISM: Artificial
<220> FEATURE:
<223> OTHER INFORMATION: Synthesised sequence

<400> SEQUENCE: 17

Gly Cys Ala Val Asn Thr Pro Val Ser Met Thr Arg Arg Arg Arg Arg
1               5                   10                  15

Arg Arg Arg Arg
            20

<210> SEQ ID NO 18
<211> LENGTH: 20
<212> TYPE: PRT
<213> ORGANISM: Artificial
<220> FEATURE:
```

-continued

<223> OTHER INFORMATION: Synthesised sequence

<400> SEQUENCE: 18

Thr Pro Val Ser Met Thr Tyr Leu Tyr Asn Lys Arg Arg Arg Arg
1               5                   10                  15

Arg Arg Arg Arg
            20

<210> SEQ ID NO 19
<211> LENGTH: 20
<212> TYPE: PRT
<213> ORGANISM: Artificial
<220> FEATURE:
<223> OTHER INFORMATION: Synthesised sequence

<400> SEQUENCE: 19

Thr Tyr Leu Tyr Asn Lys Tyr Ser Phe Lys Leu Arg Arg Arg Arg
1               5                   10                  15

Arg Arg Arg Arg
            20

<210> SEQ ID NO 20
<211> LENGTH: 20
<212> TYPE: PRT
<213> ORGANISM: Artificial
<220> FEATURE:
<223> OTHER INFORMATION: Synthesised sequence

<400> SEQUENCE: 20

Lys Tyr Ser Phe Lys Leu Ile Leu Ala Glu Tyr Arg Arg Arg Arg
1               5                   10                  15

Arg Arg Arg Arg
            20

<210> SEQ ID NO 21
<211> LENGTH: 20
<212> TYPE: PRT
<213> ORGANISM: Artificial
<220> FEATURE:
<223> OTHER INFORMATION: Synthesised sequence

<400> SEQUENCE: 21

Leu Ile Leu Ala Glu Tyr Ile Arg His Arg Asn Arg Arg Arg Arg
1               5                   10                  15

Arg Arg Arg Arg
            20

<210> SEQ ID NO 22
<211> LENGTH: 20
<212> TYPE: PRT
<213> ORGANISM: Artificial
<220> FEATURE:
<223> OTHER INFORMATION: Synthesised sequence

<400> SEQUENCE: 22

Tyr Ile Arg His Arg Asn Thr Ile Ser Gly Asn Arg Arg Arg Arg
1               5                   10                  15

Arg Arg Arg Arg
            20

<210> SEQ ID NO 23
<211> LENGTH: 20
<212> TYPE: PRT
<213> ORGANISM: Artificial
<220> FEATURE:

```
<223> OTHER INFORMATION: Synthesised sequence

<400> SEQUENCE: 23

Arg Asn Thr Ile Ser Gly Asn Ile Tyr Ser Ala Arg Arg Arg Arg
1               5                   10                  15

Arg Arg Arg Arg
            20

<210> SEQ ID NO 24
<211> LENGTH: 20
<212> TYPE: PRT
<213> ORGANISM: Artificial
<220> FEATURE:
<223> OTHER INFORMATION: Synthesised sequence

<400> SEQUENCE: 24

Gly Asn Ile Tyr Ser Ala Leu Met Thr Leu Asp Arg Arg Arg Arg
1               5                   10                  15

Arg Arg Arg Arg
            20

<210> SEQ ID NO 25
<211> LENGTH: 20
<212> TYPE: PRT
<213> ORGANISM: Artificial
<220> FEATURE:
<223> OTHER INFORMATION: Synthesised sequence

<400> SEQUENCE: 25

Asp Ser Gly Leu Phe Asp Phe Val Asn Phe Val Arg Arg Arg Arg
1               5                   10                  15

Arg Arg Arg Arg
            20

<210> SEQ ID NO 26
<211> LENGTH: 20
<212> TYPE: PRT
<213> ORGANISM: Artificial
<220> FEATURE:
<223> OTHER INFORMATION: Synthesised sequence

<400> SEQUENCE: 26

Asp Phe Val Asn Phe Val Lys Asp Met Ile Cys Arg Arg Arg Arg
1               5                   10                  15

Arg Arg Arg Arg
            20

<210> SEQ ID NO 27
<211> LENGTH: 20
<212> TYPE: PRT
<213> ORGANISM: Artificial
<220> FEATURE:
<223> OTHER INFORMATION: Synthesised sequence

<400> SEQUENCE: 27

Val Lys Asp Met Ile Cys Cys Asp Ser Arg Ile Arg Arg Arg Arg
1               5                   10                  15

Arg Arg Arg Arg
            20

<210> SEQ ID NO 28
<211> LENGTH: 20
<212> TYPE: PRT
<213> ORGANISM: Artificial
<220> FEATURE:
```

<223> OTHER INFORMATION: Synthesised sequence

<400> SEQUENCE: 28

Asp Ser Arg Ile Val Val Ala Leu Ser Ser Leu Arg Arg Arg Arg
1               5                   10                  15

Arg Arg Arg Arg
            20

<210> SEQ ID NO 29
<211> LENGTH: 20
<212> TYPE: PRT
<213> ORGANISM: Artificial
<220> FEATURE:
<223> OTHER INFORMATION: Synthesised sequence

<400> SEQUENCE: 29

Val Ala Leu Ser Ser Leu Val Ser Lys His Trp Arg Arg Arg Arg
1               5                   10                  15

Arg Arg Arg Arg
            20

<210> SEQ ID NO 30
<211> LENGTH: 20
<212> TYPE: PRT
<213> ORGANISM: Artificial
<220> FEATURE:
<223> OTHER INFORMATION: Synthesised sequence

<400> SEQUENCE: 30

Leu Val Ser Lys His Trp Glu Leu Thr Asn Arg Arg Arg Arg Arg
1               5                   10                  15

Arg Arg Arg Arg
            20

<210> SEQ ID NO 31
<211> LENGTH: 20
<212> TYPE: PRT
<213> ORGANISM: Artificial
<220> FEATURE:
<223> OTHER INFORMATION: Synthesised sequence

<400> SEQUENCE: 31

Glu Leu Thr Asn Lys Lys Tyr Arg Cys Met Ala Arg Arg Arg Arg
1               5                   10                  15

Arg Arg Arg Arg
            20

<210> SEQ ID NO 32
<211> LENGTH: 20
<212> TYPE: PRT
<213> ORGANISM: Artificial
<220> FEATURE:
<223> OTHER INFORMATION: Synthesised sequence

<400> SEQUENCE: 32

Lys Ala Leu Ser Ile Phe Tyr Glu Lys Tyr Leu Arg Arg Arg Arg
1               5                   10                  15

Arg Arg Arg Arg
            20

<210> SEQ ID NO 33
<211> LENGTH: 9
<212> TYPE: PRT
<213> ORGANISM: Artificial
<220> FEATURE:

<223> OTHER INFORMATION: Synthesised sequence

<400> SEQUENCE: 33

Arg Arg Arg Arg Arg Arg Arg Arg Arg
1               5

<210> SEQ ID NO 34
<211> LENGTH: 11
<212> TYPE: PRT
<213> ORGANISM: Artificial
<220> FEATURE:
<223> OTHER INFORMATION: Synthesised sequence

<400> SEQUENCE: 34

Tyr Gly Arg Lys Lys Arg Arg Gln Arg Arg Arg
1               5                   10

<210> SEQ ID NO 35
<211> LENGTH: 16
<212> TYPE: PRT
<213> ORGANISM: Artificial
<220> FEATURE:
<223> OTHER INFORMATION: Synthesised sequence

<400> SEQUENCE: 35

Arg Gln Ile Lys Ile Trp Phe Gln Asn Arg Arg Met Lys Trp Lys Lys
1               5                   10                  15

<210> SEQ ID NO 36
<211> LENGTH: 22
<212> TYPE: PRT
<213> ORGANISM: Artificial
<220> FEATURE:
<223> OTHER INFORMATION: Synthesised sequence

<400> SEQUENCE: 36

Lys Tyr Ser Phe Lys Leu Ile Leu Ala Glu Tyr Tyr Gly Arg Lys Lys
1               5                   10                  15

Arg Arg Gln Arg Arg Arg
            20

<210> SEQ ID NO 37
<211> LENGTH: 22
<212> TYPE: PRT
<213> ORGANISM: Artificial
<220> FEATURE:
<223> OTHER INFORMATION: Synthesised sequence

<400> SEQUENCE: 37

Arg Asn Thr Ile Ser Gly Asn Ile Tyr Ser Ala Tyr Gly Arg Lys Lys
1               5                   10                  15

Arg Arg Gln Arg Arg Arg
            20

<210> SEQ ID NO 38
<211> LENGTH: 20
<212> TYPE: PRT
<213> ORGANISM: Artificial
<220> FEATURE:
<223> OTHER INFORMATION: Synthesised sequence

<400> SEQUENCE: 38

Arg Arg Arg Arg Arg Arg Arg Arg Lys Tyr Ser Phe Lys Leu Ile
1               5                   10                  15

Leu Ala Glu Tyr
            20

```
<210> SEQ ID NO 39
<211> LENGTH: 20
<212> TYPE: PRT
<213> ORGANISM: Artificial
<220> FEATURE:
<223> OTHER INFORMATION: Synthesised sequence

<400> SEQUENCE: 39

Arg Arg Arg Arg Arg Arg Arg Arg Arg Arg Asn Thr Ile Ser Gly Asn
1               5                   10                  15

Ile Tyr Ser Ala
            20

<210> SEQ ID NO 40
<211> LENGTH: 19
<212> TYPE: PRT
<213> ORGANISM: Artificial
<220> FEATURE:
<223> OTHER INFORMATION: Synthesised sequence

<400> SEQUENCE: 40

Tyr Ser Phe Lys Leu Ile Leu Ala Glu Tyr Arg Arg Arg Arg Arg Arg
1               5                   10                  15

Arg Arg Arg

<210> SEQ ID NO 41
<211> LENGTH: 18
<212> TYPE: PRT
<213> ORGANISM: Artificial
<220> FEATURE:
<223> OTHER INFORMATION: Synthesised sequence

<400> SEQUENCE: 41

Ser Phe Lys Leu Ile Leu Ala Glu Tyr Arg Arg Arg Arg Arg Arg Arg
1               5                   10                  15

Arg Arg

<210> SEQ ID NO 42
<211> LENGTH: 17
<212> TYPE: PRT
<213> ORGANISM: Artificial
<220> FEATURE:
<223> OTHER INFORMATION: Synthesised sequence

<400> SEQUENCE: 42

Lys Tyr Ser Phe Lys Leu Ile Leu Arg Arg Arg Arg Arg Arg Arg Arg
1               5                   10                  15

Arg

<210> SEQ ID NO 43
<211> LENGTH: 14
<212> TYPE: PRT
<213> ORGANISM: Artificial
<220> FEATURE:
<223> OTHER INFORMATION: Synthesised sequence

<400> SEQUENCE: 43

Lys Tyr Ser Phe Lys Arg Arg Arg Arg Arg Arg Arg Arg Arg
1               5                   10

<210> SEQ ID NO 44
<211> LENGTH: 20
<212> TYPE: PRT
<213> ORGANISM: Artificial
```

```
<220> FEATURE:
<223> OTHER INFORMATION: Synthesised sequence

<400> SEQUENCE: 44

Ala Tyr Ser Phe Lys Leu Ile Leu Ala Glu Tyr Arg Arg Arg Arg
1               5                   10                  15

Arg Arg Arg Arg
            20

<210> SEQ ID NO 45
<211> LENGTH: 20
<212> TYPE: PRT
<213> ORGANISM: Artificial
<220> FEATURE:
<223> OTHER INFORMATION: Synthesised sequence

<400> SEQUENCE: 45

Lys Ala Ser Phe Lys Leu Ile Leu Ala Glu Tyr Arg Arg Arg Arg
1               5                   10                  15

Arg Arg Arg Arg
            20

<210> SEQ ID NO 46
<211> LENGTH: 20
<212> TYPE: PRT
<213> ORGANISM: Artificial
<220> FEATURE:
<223> OTHER INFORMATION: Synthesised sequence

<400> SEQUENCE: 46

Lys Tyr Ala Phe Lys Leu Ile Leu Ala Glu Tyr Arg Arg Arg Arg
1               5                   10                  15

Arg Arg Arg Arg
            20

<210> SEQ ID NO 47
<211> LENGTH: 20
<212> TYPE: PRT
<213> ORGANISM: Artificial
<220> FEATURE:
<223> OTHER INFORMATION: Synthesised sequence

<400> SEQUENCE: 47

Lys Tyr Ser Ala Lys Leu Ile Leu Ala Glu Tyr Arg Arg Arg Arg
1               5                   10                  15

Arg Arg Arg Arg
            20

<210> SEQ ID NO 48
<211> LENGTH: 20
<212> TYPE: PRT
<213> ORGANISM: Artificial
<220> FEATURE:
<223> OTHER INFORMATION: Synthesised sequence

<400> SEQUENCE: 48

Lys Tyr Ser Phe Ala Leu Ile Leu Ala Glu Tyr Arg Arg Arg Arg
1               5                   10                  15

Arg Arg Arg Arg
            20

<210> SEQ ID NO 49
<211> LENGTH: 20
<212> TYPE: PRT
<213> ORGANISM: Artificial
```

```
<220> FEATURE:
<223> OTHER INFORMATION: Synthesised sequence

<400> SEQUENCE: 49

Lys Tyr Ser Phe Lys Ala Ile Leu Ala Glu Tyr Arg Arg Arg Arg
1               5                   10                  15

Arg Arg Arg Arg
            20

<210> SEQ ID NO 50
<211> LENGTH: 20
<212> TYPE: PRT
<213> ORGANISM: Artificial
<220> FEATURE:
<223> OTHER INFORMATION: Synthesised sequence

<400> SEQUENCE: 50

Lys Tyr Ser Phe Lys Leu Ala Leu Ala Glu Tyr Arg Arg Arg Arg
1               5                   10                  15

Arg Arg Arg Arg
            20

<210> SEQ ID NO 51
<211> LENGTH: 20
<212> TYPE: PRT
<213> ORGANISM: Artificial
<220> FEATURE:
<223> OTHER INFORMATION: Synthesised sequence

<400> SEQUENCE: 51

Lys Tyr Ser Phe Lys Leu Ile Ala Ala Glu Tyr Arg Arg Arg Arg
1               5                   10                  15

Arg Arg Arg Arg
            20

<210> SEQ ID NO 52
<211> LENGTH: 20
<212> TYPE: PRT
<213> ORGANISM: Artificial
<220> FEATURE:
<223> OTHER INFORMATION: Synthesised sequence

<400> SEQUENCE: 52

Lys Tyr Ser Phe Lys Leu Ile Leu Ala Ala Tyr Arg Arg Arg Arg
1               5                   10                  15

Arg Arg Arg Arg
            20

<210> SEQ ID NO 53
<211> LENGTH: 20
<212> TYPE: PRT
<213> ORGANISM: Artificial
<220> FEATURE:
<223> OTHER INFORMATION: Synthesised sequence

<400> SEQUENCE: 53

Lys Tyr Ser Phe Lys Leu Ile Leu Ala Glu Ala Arg Arg Arg Arg
1               5                   10                  15

Arg Arg Arg Arg
            20

<210> SEQ ID NO 54
<211> LENGTH: 4
<212> TYPE: PRT
<213> ORGANISM: Vaccinia virus
```

```
<400> SEQUENCE: 54

Phe Lys Leu Ile
1

<210> SEQ ID NO 55
<211> LENGTH: 6
<212> TYPE: PRT
<213> ORGANISM: Vaccinia virus

<400> SEQUENCE: 55

Ser Phe Lys Leu Ile Leu
1               5

<210> SEQ ID NO 56
<211> LENGTH: 15
<212> TYPE: PRT
<213> ORGANISM: Artificial
<220> FEATURE:
<223> OTHER INFORMATION: Synthesised sequence

<400> SEQUENCE: 56

Ser Phe Lys Leu Ile Leu Arg Arg Arg Arg Arg Arg Arg Arg Arg
1               5                   10                  15

<210> SEQ ID NO 57
<211> LENGTH: 15
<212> TYPE: PRT
<213> ORGANISM: Artificial
<220> FEATURE:
<223> OTHER INFORMATION: Synthesised sequence

<400> SEQUENCE: 57

Arg Arg Arg Arg Arg Arg Arg Arg Arg Ser Phe Lys Leu Ile Leu
1               5                   10                  15

<210> SEQ ID NO 58
<211> LENGTH: 6
<212> TYPE: PRT
<213> ORGANISM: Vaccinia virus

<400> SEQUENCE: 58

Thr Ile Ser Gly Asn Ile
1               5

<210> SEQ ID NO 59
<211> LENGTH: 15
<212> TYPE: PRT
<213> ORGANISM: Artificial
<220> FEATURE:
<223> OTHER INFORMATION: Synthesised sequence

<400> SEQUENCE: 59

Thr Ile Ser Gly Asn Ile Arg Arg Arg Arg Arg Arg Arg Arg Arg
1               5                   10                  15

<210> SEQ ID NO 60
<211> LENGTH: 15
<212> TYPE: PRT
<213> ORGANISM: Artificial
<220> FEATURE:
<223> OTHER INFORMATION: Synthesised sequence

<400> SEQUENCE: 60

Arg Arg Arg Arg Arg Arg Arg Arg Arg Thr Ile Ser Gly Asn Ile
1               5                   10                  15
```

```
<210> SEQ ID NO 61
<211> LENGTH: 20
<212> TYPE: PRT
<213> ORGANISM: Artificial
<220> FEATURE:
<223> OTHER INFORMATION: Synthesised sequence

<400> SEQUENCE: 61

Asp Ile Val Lys Leu Thr Val Tyr Asp Cys Ile Arg Arg Arg Arg
1               5                   10                  15

Arg Arg Arg Arg
            20

<210> SEQ ID NO 62
<211> LENGTH: 14
<212> TYPE: PRT
<213> ORGANISM: Artificial
<220> FEATURE:
<223> OTHER INFORMATION: Synthesised sequence

<400> SEQUENCE: 62

Arg Arg Arg Arg Arg Arg Arg Arg Arg Phe Lys Leu Ile Leu
1               5                   10

<210> SEQ ID NO 63
<211> LENGTH: 14
<212> TYPE: PRT
<213> ORGANISM: Artificial
<220> FEATURE:
<223> OTHER INFORMATION: Synthesised sequence

<400> SEQUENCE: 63

Arg Arg Arg Arg Arg Arg Arg Arg Arg Ser Phe Lys Leu Ile
1               5                   10

<210> SEQ ID NO 64
<211> LENGTH: 13
<212> TYPE: PRT
<213> ORGANISM: Artificial
<220> FEATURE:
<223> OTHER INFORMATION: Synthesised sequence

<400> SEQUENCE: 64

Arg Arg Arg Arg Arg Arg Arg Arg Arg Phe Lys Leu Ile
1               5                   10

<210> SEQ ID NO 65
<211> LENGTH: 15
<212> TYPE: PRT
<213> ORGANISM: Artificial
<220> FEATURE:
<223> OTHER INFORMATION: Synthesised sequence

<400> SEQUENCE: 65

Arg Arg Arg Arg Arg Arg Arg Arg Arg Ser Phe Lys Leu Phe Leu
1               5                   10                  15

<210> SEQ ID NO 66
<211> LENGTH: 17
<212> TYPE: PRT
<213> ORGANISM: Artificial
<220> FEATURE:
<223> OTHER INFORMATION: Synthesised sequence

<400> SEQUENCE: 66

His His His His His His Lys Tyr Ser Phe Lys Leu Ile Leu Ala Glu
1               5                   10                  15
```

Tyr

<210> SEQ ID NO 67
<211> LENGTH: 17
<212> TYPE: PRT
<213> ORGANISM: Artificial
<220> FEATURE:
<223> OTHER INFORMATION: Synthesised sequence

<400> SEQUENCE: 67

His His His His His His Arg Asn Thr Ile Ser Gly Asn Ile Tyr Ser
1               5                   10                  15

Ala

<210> SEQ ID NO 68
<211> LENGTH: 5
<212> TYPE: PRT
<213> ORGANISM: Vaccinia virus

<400> SEQUENCE: 68

Phe Lys Leu Ile Leu
1               5

<210> SEQ ID NO 69
<211> LENGTH: 4
<212> TYPE: PRT
<213> ORGANISM: vaccinia virus

<400> SEQUENCE: 69

Lys Leu Ile Leu
1

<210> SEQ ID NO 70
<211> LENGTH: 8
<212> TYPE: PRT
<213> ORGANISM: vaccinia virus

<400> SEQUENCE: 70

Lys Tyr Ser Phe Lys Leu Ile Leu
1               5

<210> SEQ ID NO 71
<211> LENGTH: 9
<212> TYPE: PRT
<213> ORGANISM: vaccinia virus

<400> SEQUENCE: 71

Ser Phe Lys Leu Ile Leu Ala Glu Tyr
1               5

<210> SEQ ID NO 72
<211> LENGTH: 10
<212> TYPE: PRT
<213> ORGANISM: vaccinia virus

<400> SEQUENCE: 72

Tyr Ser Phe Lys Leu Ile Leu Ala Glu Tyr
1               5                   10

<210> SEQ ID NO 73
<211> LENGTH: 14
<212> TYPE: PRT
<213> ORGANISM: artificial
<220> FEATURE:
<223> OTHER INFORMATION: Synthesised sequence

```
<400> SEQUENCE: 73

Phe Lys Leu Ile Leu Arg Arg Arg Arg Arg Arg Arg Arg
1               5                   10

<210> SEQ ID NO 74
<211> LENGTH: 13
<212> TYPE: PRT
<213> ORGANISM: artificial
<220> FEATURE:
<223> OTHER INFORMATION: Synthesised sequence

<400> SEQUENCE: 74

Lys Leu Ile Leu Arg Arg Arg Arg Arg Arg Arg Arg Arg
1               5                   10

<210> SEQ ID NO 75
<211> LENGTH: 17
<212> TYPE: PRT
<213> ORGANISM: artificial
<220> FEATURE:
<223> OTHER INFORMATION: Synthesised sequence

<400> SEQUENCE: 75

Arg Arg Arg Arg Arg Arg Arg Arg Arg Lys Tyr Ser Phe Lys Leu Ile
1               5                   10                  15

Leu

<210> SEQ ID NO 76
<211> LENGTH: 18
<212> TYPE: PRT
<213> ORGANISM: artificial
<220> FEATURE:
<223> OTHER INFORMATION: Synthesised sequence

<400> SEQUENCE: 76

Arg Arg Arg Arg Arg Arg Arg Arg Arg Ser Phe Lys Leu Ile Leu Ala
1               5                   10                  15

Glu Tyr

<210> SEQ ID NO 77
<211> LENGTH: 19
<212> TYPE: PRT
<213> ORGANISM: artificial
<220> FEATURE:
<223> OTHER INFORMATION: Synthesised sequence

<400> SEQUENCE: 77

Arg Arg Arg Arg Arg Arg Arg Arg Arg Tyr Ser Phe Lys Leu Ile Leu
1               5                   10                  15

Ala Glu Tyr

<210> SEQ ID NO 78
<211> LENGTH: 13
<212> TYPE: PRT
<213> ORGANISM: artificial
<220> FEATURE:
<223> OTHER INFORMATION: Synthesised sequence

<400> SEQUENCE: 78

Arg Arg Arg Arg Arg Arg Arg Arg Arg Lys Leu Ile Leu
1               5                   10

<210> SEQ ID NO 79
<211> LENGTH: 7
```

```
<212> TYPE: PRT
<213> ORGANISM: vaccinia virus

<400> SEQUENCE: 79

Tyr Ser Phe Lys Leu Ile Leu
1               5

<210> SEQ ID NO 80
<211> LENGTH: 16
<212> TYPE: PRT
<213> ORGANISM: artificial
<220> FEATURE:
<223> OTHER INFORMATION: Synthesised sequence

<400> SEQUENCE: 80

Tyr Ser Phe Lys Leu Ile Leu Arg Arg Arg Arg Arg Arg Arg Arg Arg
1               5                   10                  15

<210> SEQ ID NO 81
<211> LENGTH: 16
<212> TYPE: PRT
<213> ORGANISM: artificial
<220> FEATURE:
<223> OTHER INFORMATION: Synthesised sequence

<400> SEQUENCE: 81

Arg Arg Arg Arg Arg Arg Arg Arg Arg Tyr Ser Phe Lys Leu Ile Leu
1               5                   10                  15

<210> SEQ ID NO 82
<211> LENGTH: 5
<212> TYPE: PRT
<213> ORGANISM: vaccinia virus

<400> SEQUENCE: 82

Lys Leu Ile Leu Ala
1               5

<210> SEQ ID NO 83
<211> LENGTH: 14
<212> TYPE: PRT
<213> ORGANISM: artificial
<220> FEATURE:
<223> OTHER INFORMATION: Synthesised sequence

<400> SEQUENCE: 83

Lys Leu Ile Leu Ala Arg Arg Arg Arg Arg Arg Arg Arg Arg
1               5                   10

<210> SEQ ID NO 84
<211> LENGTH: 14
<212> TYPE: PRT
<213> ORGANISM: artificial
<220> FEATURE:
<223> OTHER INFORMATION: Synthesised sequence

<400> SEQUENCE: 84

Arg Arg Arg Arg Arg Arg Arg Arg Arg Lys Leu Ile Leu Ala
1               5                   10

<210> SEQ ID NO 85
<211> LENGTH: 6
<212> TYPE: PRT
<213> ORGANISM: vaccinia virus

<400> SEQUENCE: 85

Phe Lys Leu Ile Leu Ala
```

<210> SEQ ID NO 86
<211> LENGTH: 15
<212> TYPE: PRT
<213> ORGANISM: artificial
<220> FEATURE:
<223> OTHER INFORMATION: Synthesised sequence

<400> SEQUENCE: 86

Phe Lys Leu Ile Leu Ala Arg Arg Arg Arg Arg Arg Arg Arg Arg
1               5                   10                  15

<210> SEQ ID NO 87
<211> LENGTH: 15
<212> TYPE: PRT
<213> ORGANISM: artificial
<220> FEATURE:
<223> OTHER INFORMATION: Synthesised sequence

<400> SEQUENCE: 87

Arg Arg Arg Arg Arg Arg Arg Arg Arg Phe Lys Leu Ile Leu Ala
1               5                   10                  15

<210> SEQ ID NO 88
<211> LENGTH: 7
<212> TYPE: PRT
<213> ORGANISM: vaccinia virus

<400> SEQUENCE: 88

Ser Phe Lys Leu Ile Leu Ala
1               5

<210> SEQ ID NO 89
<211> LENGTH: 16
<212> TYPE: PRT
<213> ORGANISM: artificial
<220> FEATURE:
<223> OTHER INFORMATION: Synthesised sequence

<400> SEQUENCE: 89

Ser Phe Lys Leu Ile Leu Ala Arg Arg Arg Arg Arg Arg Arg Arg Arg
1               5                   10                  15

<210> SEQ ID NO 90
<211> LENGTH: 16
<212> TYPE: PRT
<213> ORGANISM: artificial
<220> FEATURE:
<223> OTHER INFORMATION: Synthesised sequence

<400> SEQUENCE: 90

Arg Arg Arg Arg Arg Arg Arg Arg Arg Ser Phe Lys Leu Ile Leu Ala
1               5                   10                  15

<210> SEQ ID NO 91
<211> LENGTH: 8
<212> TYPE: PRT
<213> ORGANISM: vaccinia virus

<400> SEQUENCE: 91

Tyr Ser Phe Lys Leu Ile Leu Ala
1               5

<210> SEQ ID NO 92
<211> LENGTH: 17
<212> TYPE: PRT

```
<213> ORGANISM: artificial
<220> FEATURE:
<223> OTHER INFORMATION: Synthesised sequence

<400> SEQUENCE: 92

Tyr Ser Phe Lys Leu Ile Leu Ala Arg Arg Arg Arg Arg Arg Arg
1               5                   10                  15

Arg

<210> SEQ ID NO 93
<211> LENGTH: 17
<212> TYPE: PRT
<213> ORGANISM: artificial
<220> FEATURE:
<223> OTHER INFORMATION: Synthesised sequence

<400> SEQUENCE: 93

Arg Arg Arg Arg Arg Arg Arg Arg Tyr Ser Phe Lys Leu Ile Leu
1               5                   10                  15

Ala

<210> SEQ ID NO 94
<211> LENGTH: 9
<212> TYPE: PRT
<213> ORGANISM: vaccinia virus

<400> SEQUENCE: 94

Lys Tyr Ser Phe Lys Leu Ile Leu Ala
1               5

<210> SEQ ID NO 95
<211> LENGTH: 18
<212> TYPE: PRT
<213> ORGANISM: artificial
<220> FEATURE:
<223> OTHER INFORMATION: Synthesised sequence

<400> SEQUENCE: 95

Lys Tyr Ser Phe Lys Leu Ile Leu Ala Arg Arg Arg Arg Arg Arg
1               5                   10                  15

Arg Arg

<210> SEQ ID NO 96
<211> LENGTH: 18
<212> TYPE: PRT
<213> ORGANISM: artificial
<220> FEATURE:
<223> OTHER INFORMATION: Synthesised sequence

<400> SEQUENCE: 96

Arg Arg Arg Arg Arg Arg Arg Arg Lys Tyr Ser Phe Lys Leu Ile
1               5                   10                  15

Leu Ala

<210> SEQ ID NO 97
<211> LENGTH: 6
<212> TYPE: PRT
<213> ORGANISM: vaccinia virus

<400> SEQUENCE: 97

Lys Leu Ile Leu Ala Glu
1               5

<210> SEQ ID NO 98
```

```
<211> LENGTH: 15
<212> TYPE: PRT
<213> ORGANISM: artificial
<220> FEATURE:
<223> OTHER INFORMATION: Synthesised sequence

<400> SEQUENCE: 98

Lys Leu Ile Leu Ala Glu Arg Arg Arg Arg Arg Arg Arg Arg Arg
1               5                   10                  15

<210> SEQ ID NO 99
<211> LENGTH: 15
<212> TYPE: PRT
<213> ORGANISM: artificial
<220> FEATURE:
<223> OTHER INFORMATION: Synthesised sequence

<400> SEQUENCE: 99

Arg Arg Arg Arg Arg Arg Arg Arg Arg Lys Leu Ile Leu Ala Glu
1               5                   10                  15

<210> SEQ ID NO 100
<211> LENGTH: 7
<212> TYPE: PRT
<213> ORGANISM: vaccinia virus

<400> SEQUENCE: 100

Phe Lys Leu Ile Leu Ala Glu
1               5

<210> SEQ ID NO 101
<211> LENGTH: 16
<212> TYPE: PRT
<213> ORGANISM: artificial
<220> FEATURE:
<223> OTHER INFORMATION: Synthesised sequence

<400> SEQUENCE: 101

Phe Lys Leu Ile Leu Ala Glu Arg Arg Arg Arg Arg Arg Arg Arg Arg
1               5                   10                  15

<210> SEQ ID NO 102
<211> LENGTH: 16
<212> TYPE: PRT
<213> ORGANISM: artificial
<220> FEATURE:
<223> OTHER INFORMATION: Synthesised sequence

<400> SEQUENCE: 102

Arg Arg Arg Arg Arg Arg Arg Arg Arg Phe Lys Leu Ile Leu Ala Glu
1               5                   10                  15

<210> SEQ ID NO 103
<211> LENGTH: 8
<212> TYPE: PRT
<213> ORGANISM: vaccinia virus

<400> SEQUENCE: 103

Ser Phe Lys Leu Ile Leu Ala Glu
1               5

<210> SEQ ID NO 104
<211> LENGTH: 17
<212> TYPE: PRT
<213> ORGANISM: artificial
<220> FEATURE:
<223> OTHER INFORMATION: Synthesised sequence
```

-continued

```
<400> SEQUENCE: 104

Ser Phe Lys Leu Ile Leu Ala Glu Arg Arg Arg Arg Arg Arg Arg
1               5                   10                  15

Arg

<210> SEQ ID NO 105
<211> LENGTH: 17
<212> TYPE: PRT
<213> ORGANISM: artificial
<220> FEATURE:
<223> OTHER INFORMATION: Synthesised sequence

<400> SEQUENCE: 105

Arg Arg Arg Arg Arg Arg Arg Arg Ser Phe Lys Leu Ile Leu Ala
1               5                   10                  15

Glu

<210> SEQ ID NO 106
<211> LENGTH: 9
<212> TYPE: PRT
<213> ORGANISM: vaccina virus

<400> SEQUENCE: 106

Tyr Ser Phe Lys Leu Ile Leu Ala Glu
1               5

<210> SEQ ID NO 107
<211> LENGTH: 18
<212> TYPE: PRT
<213> ORGANISM: artificial
<220> FEATURE:
<223> OTHER INFORMATION: Synthesised sequence

<400> SEQUENCE: 107

Tyr Ser Phe Lys Leu Ile Leu Ala Glu Arg Arg Arg Arg Arg Arg
1               5                   10                  15

Arg Arg

<210> SEQ ID NO 108
<211> LENGTH: 18
<212> TYPE: PRT
<213> ORGANISM: artificial
<220> FEATURE:
<223> OTHER INFORMATION: Synthesised sequence

<400> SEQUENCE: 108

Arg Arg Arg Arg Arg Arg Arg Arg Arg Tyr Ser Phe Lys Leu Ile Leu
1               5                   10                  15

Ala Glu

<210> SEQ ID NO 109
<211> LENGTH: 10
<212> TYPE: PRT
<213> ORGANISM: vaccinia virus

<400> SEQUENCE: 109

Lys Tyr Ser Phe Lys Leu Ile Leu Ala Glu
1               5                   10

<210> SEQ ID NO 110
<211> LENGTH: 19
<212> TYPE: PRT
<213> ORGANISM: artificial
<220> FEATURE:
```

-continued

<223> OTHER INFORMATION: Synthesised sequence

<400> SEQUENCE: 110

Lys Tyr Ser Phe Lys Leu Ile Leu Ala Glu Arg Arg Arg Arg Arg
1               5                   10                  15

Arg Arg Arg

<210> SEQ ID NO 111
<211> LENGTH: 19
<212> TYPE: PRT
<213> ORGANISM: artificial
<220> FEATURE:
<223> OTHER INFORMATION: Synthesised sequence

<400> SEQUENCE: 111

Arg Arg Arg Arg Arg Arg Arg Arg Arg Lys Tyr Ser Phe Lys Leu Ile
1               5                   10                  15

Leu Ala Glu

<210> SEQ ID NO 112
<211> LENGTH: 7
<212> TYPE: PRT
<213> ORGANISM: vaccinia virus

<400> SEQUENCE: 112

Lys Leu Ile Leu Ala Glu Tyr
1               5

<210> SEQ ID NO 113
<211> LENGTH: 16
<212> TYPE: PRT
<213> ORGANISM: artificial
<220> FEATURE:
<223> OTHER INFORMATION: Synthesised sequence

<400> SEQUENCE: 113

Lys Leu Ile Leu Ala Glu Tyr Arg Arg Arg Arg Arg Arg Arg Arg Arg
1               5                   10                  15

<210> SEQ ID NO 114
<211> LENGTH: 16
<212> TYPE: PRT
<213> ORGANISM: artificial
<220> FEATURE:
<223> OTHER INFORMATION: Synthesised sequence

<400> SEQUENCE: 114

Arg Arg Arg Arg Arg Arg Arg Arg Arg Lys Leu Ile Leu Ala Glu Tyr
1               5                   10                  15

<210> SEQ ID NO 115
<211> LENGTH: 8
<212> TYPE: PRT
<213> ORGANISM: vaccinia virus

<400> SEQUENCE: 115

Phe Lys Leu Ile Leu Ala Glu Tyr
1               5

<210> SEQ ID NO 116
<211> LENGTH: 17
<212> TYPE: PRT
<213> ORGANISM: artificial
<220> FEATURE:
<223> OTHER INFORMATION: Synthesised sequence

```
<400> SEQUENCE: 116

Phe Lys Leu Ile Leu Ala Glu Tyr Arg Arg Arg Arg Arg Arg Arg
1               5                   10                  15

Arg

<210> SEQ ID NO 117
<211> LENGTH: 17
<212> TYPE: PRT
<213> ORGANISM: Artificial
<220> FEATURE:
<223> OTHER INFORMATION: Synthesised sequence

<400> SEQUENCE: 117

Arg Arg Arg Arg Arg Arg Arg Arg Arg Phe Lys Leu Ile Leu Ala Glu
1               5                   10                  15

Tyr
```

VACCINIA VIRUS PROTEIN A46 PEPTIDE AND USE THEREOF

This is a national stage of PCT/IE09/000080 filed Nov. 17, 2009 and published in English, claiming benefit of U.S. provisional application No. 61/193,319, filed Nov. 17, 2008, hereby incorporated by reference.

BACKGROUND OF THE INVENTION

1. Field of the Invention

This invention relates to a peptide derived from a vaccinia virus protein. In particular the invention relates to a peptide derived from the vaccinia virus protein A46.

2. Description of Related Art

Pattern recognition receptors (PRRs) are critical for the ability of the innate immune response to detect pathogens. Examples of classes of PRRs include Toll-like receptors (TLRs), RIG-I-like receptors (RLRs) and NOD-like receptors (NLRs). TLRs recognize pathogen-associated molecular patterns (PAMPs) on microorganisms, leading to the activation of signaling pathways and subsequent altered gene expression. This leads to the production of anti-microbial effector cytokines such as the proinflammatory cytokines interleukin-1 (IL-1) and tumour necrosis factor α (TNFα), and the type I interferons (IFNs) IFNα and IFNβ. Specific TLRs have been shown to detect particular PAMPs, for example TLR2 recognises certain bacterial lipopeptides, TLR3 recognises double-stranded (ds) RNA, TLR4 responds to lipopolysaccharide (LPS), TLR7 or TLR8 to ssRNA, and TLR9 to dsDNA containing CpG motifs (Akira et al, 2006).

TLR4 is of particular interest here, and is one of the most important and studied of the TLRs, given its role in mediating the many effects of LPS on cells. Furthermore, TLR4 can respond to a variety of other cellular insults and endogenous danger signals, making it an attractive drug target for therapeutic intervention in the large range of diseases now appreciated to involve inappropriate or aberrant activation of innate immune signaling. Inhibitors of specific innate immune signaling pathways are an attractive strategy in certain disease contexts in order to disable pathways contributing to disease while maintaining some redundant pathogen detection systems. As such, a specific inhibitor of TLR4 would be a valuable asset.

An important example of a role for TLRs in disease processes is that of inflammation. Inflammation is a complex process underlying a large number of acute and chronic diseases such as sepsis, rheumatoid arthritis, multiple sclerosis and colitis. Most therapeutic approaches to blocking inflammation target individual effector cytokines such as TNF, often with good effect. There is now strong evidence that TLRs have a crucial role in initiating both pathogen-induced and sterile inflammation, and as such TLRs provide the initial trigger which ultimately leads to the production of such effector cytokines (O'Neill, 2006). Therefore, targeting the initial intracellular TLR signalling cascades directly is ultimately likely to be an even more effective approach.

TLR4 activators cause it to homodimerise, via its intracellular Toll-IL-1R (TIR) domain. This leads to the engagement of TIR domain-containing adaptor proteins with the receptor complex, namely myeloid differentiation factor 88 (MyD88), MyD88 adaptor-like (Mal, also called TIRAP), TIR domain-containing adaptor inducing IFNβ (TRIF), and TRIF-related adaptor molecule (TRAM). Together, MyD88 and Mal mediate a signaling pathway leading to NFκB and mitogen-activated protein kinase (MAPK) activation, while TRAM and TRIF control a pathway leading to NFκB and IFN regulatory factor (IRF) activation (O'Neill and Bowie, 2007). Other TLRs use different repertoires of TIR adaptors to signal, for example TLR2 utilises MyD88 and Mal, TLR3 utilises only TRIF and TLR9 utilises only MyD88 (O'Neill and Bowie, 2007).

Two vaccinia virus proteins, A46R and A52R, have been identified which can modulate intracellular signalling by TLRs and thus inhibit the TLR-initiated immune response. A52R potently blocks TLR-induced activation of the transcription factor NFκB (a well-known lead drug target) by interacting with the TLR signalling molecule IRAK2 (Harte et al, 2003; Keating et al, 2007). A46 has distinct targets, and can suppress TLR signaling axes utilising MyD88, Mal, TRIF or TRAM, leading to inhibition of MAP kinase, NFκB and IRF3 activation (Stack et al, 2005). This is because A46 has a TIR domain, which allows it to bind to mammalian TIR adaptors (Stack et al, 2005).

SUMMARY OF THE INVENTION

We describe a peptide derived from the vaccinia virus protein A46 and use thereof in methods for suppressing a pro-inflammatory response mediated by TLR4. The peptide may comprise the consensus sequence KLIL (SEQ ID No. 69), for example the peptide may be selected from one or more of the following (in which X indicates the presence of the amino acid residue):

| AMINO ACID RESIDUE | | | | | | | | | | | SEQ ID NO. | | |
| --- | --- | --- | --- | --- | --- | --- | --- | --- | --- | --- | --- | --- | --- |
| | | | | | | | | | | | Peptide (no delivery sequence) | Peptide with 9R delivery sequence at the C terminus | Peptide with 9R delivery sequence at the N terminus |
| K | Y | S | F | K | L | I | L | A | E | Y | | | |
| | | | | X | X | X | X | | | | 69 | 74 | 78 |
| | | | X | X | X | X | X | | | | 68 | 73 | 62 |
| | | X | X | X | X | X | X | | | | 55 | 56 | 57 |
| | X | X | X | X | X | X | X | | | | 79 | 80 | 81 |
| X | X | X | X | X | X | X | X | | | | 70 | 42 | 75 |
| | | | | X | X | X | X | X | | | 82 | 83 | 84 |
| | | | X | X | X | X | X | X | | | 85 | 86 | 87 |
| | | X | X | X | X | X | X | X | | | 88 | 89 | 90 |
| | X | X | X | X | X | X | X | X | | | 91 | 92 | 93 |
| X | X | X | X | X | X | X | X | X | | | 94 | 95 | 96 |
| | | | | X | X | X | X | X | X | | 97 | 98 | 99 |
| | | | X | X | X | X | X | X | X | | 100 | 101 | 102 |

-continued

| AMINO ACID RESIDUE | | | | | | | | | | | SEQ ID NO. | | |
|---|---|---|---|---|---|---|---|---|---|---|---|---|---|
| K | Y | S | F | K | L | I | L | A | E | Y | Peptide (no delivery sequence) | Peptide with 9R delivery sequence at the C terminus | Peptide with 9R delivery sequence at the N terminus |
|   |   | X | X | X | X | X | X | X | X |   | 103 | 104 | 105 |
|   | X | X | X | X | X | X | X | X | X |   | 106 | 107 | 108 |
| X | X | X | X | X | X | X | X | X | X |   | 109 | 110 | 111 |
|   |   |   |   | X | X | X | X | X | X | X | 112 | 113 | 114 |
|   |   |   | X | X | X | X | X | X | X | X | 115 | 116 | 117 |
|   |   | X | X | X | X | X | X | X | X | X | 71 | 41 | 76 |
|   | X | X | X | X | X | X | X | X | X | X | 72 | 40 | 77 |
| X | X | X | X | X | X | X | X | X | X | X | 4 | 20 | 38 |

In one embodiment the peptide may comprise the consensus sequence FKLIL (SEQ ID No. 68)

In accordance with the invention there is provided a peptide for inhibiting Toll-like receptor 4 (TLR4) signalling comprising the amino acid sequence of SEQ ID No. 69.

The invention further provides a peptide for inhibiting Toll-like receptor 4 (TLR4) signalling comprising the amino acid sequence of SEQ ID No. 68.

The invention also provides a peptide for inhibiting Toll-like receptor 4 (TLR4) signalling comprising the amino acid sequence of SEQ ID NO. 4, SEQ ID NO 55, SEQ ID NO 68, SEQ ID NO. 69, SEQ ID NO 70, SEQ ID NO 71, SEQ ID NO 72, SEQ ID NO 79, SEQ ID NO 82, SEQ ID NO 85, SEQ ID NO 88, SEQ ID NO 91, SEQ ID NO 94, SEQ ID NO 97, SEQ ID NO 100, SEQ ID NO 103, SEQ ID NO 106, SEQ ID NO 109, SEQ ID NO 112, or SEQ ID NO 115.

The amino acid sequence may be in the L-form. Alternatively, the amino acid sequence may be in the D-form.

The peptide may comprise a delivery sequence. The delivery sequence may be a cationic peptide. The delivery sequence may be between 8 and 16 amino acids in length. The delivery sequence may comprise the amino acid sequence of SEQ ID NO. 33, SEQ ID NO. 34, or SEQ ID NO. 35.

The delivery sequence may be attached to the C terminus of the peptide. The peptide may comprise an amino acid sequence selected from the group comprising: SEQ ID No. 20, SEQ ID No. 40, SEQ ID No. 41, SEQ ID No. 42, SEQ ID No. 56, SEQ ID No. 73, SEQ ID No. 74, SEQ ID No. 80, SEQ ID No. 83, SEQ ID No. 86, SEQ ID No. 89, SEQ ID No. 92, SEQ ID No. 95, SEQ ID No. 98, SEQ ID No. 101, SEQ ID No. 104, SEQ ID No. 107, SEQ ID No. 110, SEQ ID No. 113, and SEQ ID No. 116.

The delivery sequence may be attached to the N terminus of the peptide. The peptide may comprise an amino acid sequence selected from the group comprising: SEQ ID No. 38, SEQ ID No. 57, SEQ ID No. 62, SEQ ID No. 75, SEQ ID No. 76, SEQ ID No. 77, SEQ ID No. 78, SEQ ID No. 81, SEQ ID No. 84, SEQ ID No. 87, SEQ ID No. 90, SEQ ID No. 93, SEQ ID No. 96, SEQ ID No. 99, SEQ ID No. 102, SEQ ID No. 105, SEQ ID No. 108, SEQ ID No. 111, SEQ ID No. 114, and SEQ ID No. 117, The invention also provides a peptide for inhibiting Toll-like receptor 4 (TLR4) signalling comprising the amino acid sequence of SEQ ID No. 20, SEQ ID No. 38, SEQ ID No. 40, SEQ ID No. 41, SEQ ID No. 42, SEQ ID No. 56, SEQ ID No. 57, SEQ ID No. 62, SEQ ID No. 73, SEQ ID No. 75, SEQ ID No. 76, SEQ ID No. 77, SEQ ID No. 80, SEQ ID No. 81, SEQ ID No. 86, SEQ ID No. 87, SEQ ID No. 89, SEQ ID No. 90, SEQ ID No. 92, SEQ ID No. 93, SEQ ID No. 95, SEQ ID No. 96, SEQ ID No. 101, SEQ ID No. 102, SEQ ID No. 104, SEQ ID No. 105, SEQ ID No. 107, SEQ ID No. 108, SEQ ID No. 110, SEQ ID No.111, SEQ ID No.116, or SEQ ID No.117

The invention further provides a peptide comprising the amino acid sequence of SEQ ID NO. 20 or a fragment, analogue or derivative thereof.

The invention also provides a peptide comprising the amino acid sequence of SEQ ID NO. 62 or a fragment, analogue or derivative thereof.

The invention further still provides a peptide comprising the amino acid sequence of SEQ ID NO. 38 or a fragment, analogue or derivative thereof.

The invention further provides a peptide comprising the amino acid sequence of SEQ ID NO. 73 or a fragment, analogue or derivative thereof.

The invention also provides a peptidomimetic for inhibiting Toll-like receptor 4 (TLR4) signalling based on a peptide as described herein.

The invention further provides a pharmaceutical composition comprising a peptide or a peptidomemetic as described herein and a pharmaceutically acceptable excipient.

The invention also provides for the use of a peptide or a peptidomimetic or a pharmaceutical composition as described herein to inhibit Toll-like receptor 4 (TLR4) signalling. The TLR4 signalling may be activated by a pathogen or pathogen component leading to a cytokine response. The TLR4 signalling protein activated may be one or more of NFκB, IκBα, IRF3 and p38. The pathogen may be a bacterium or a bacterial component such as lipopolysaccharide.

The invention further provides a method of treatment or prophylaxis of a TLR4-associated disease comprising the step of administering an effective amount of a peptide aor a peptidomimetic or a pharmaceutical composition as described herein to a subject. The disease may be a disease of the immune system and/or is an inflammatory disease. For example, the disease may be one or more of: sepsis, rheumatoid arthritis, colitis, multiple sclerosis, irritable bowel disease, cancer, sterile inflammation, pathogen-associated inflammation, kidney ischemia/reperfusion injury, liver ischemia/reperfusion injury, plaque development in atherosclerosis-prone subjects, and acute lung injury.

The invention also provides a method of inhibiting TLR4-induced cytokine responses comprising the step of administering an effective amount of a peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, or SEQ ID No. 117 to a subject.

The invention further provides a method of inhibiting TLR4 induced responses comprising the step of administering an effective amount of a peptidomimetic based on the amino acid sequence of SEQ ID No. 4, SEQ ID No. 55, SEQ ID No. 68, SEQ ID No. 69, SEQ ID No. 70, SEQ ID No. 71, SEQ ID No. 72, SEQ ID No. 79, SEQ ID No. 82, SEQ ID No. 85, SEQ ID No. 88, SEQ ID No. 91, SEQ ID No. 94, SEQ ID No. 97, SEQ ID No. 100, SEQ ID No. 103, SEQ ID No. 106, SEQ ID No. 109, SEQ ID No. 112, or SEQ ID No. 115 to a subject.

The invention also provides a method of inhibiting TLR4 induced responses comprising the step of administering an effective amount of a pharmaceutical composition comprising a peptide having the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, SEQ ID No. 117, or peptidomimetic thereof and a pharmaceutically acceptable excipient to a subject.

The invention further provides a method of suppressing a pro-inflammatory immune response comprising the step of administering an effective amount of a peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No. 85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, SEQ ID No. 117, or peptidomimetic thereof to a subject.

The invention also provides for the use of a peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, or SEQ ID No. 117 to suppress an immune response wherein the immune response is mediated through the stimulation of TLR4 leading to the activation of a MAP kinase, or at least one transcription factor selected from NF-κB and at least one IRF. The IRF may be IRF3 or IRF7.

The invention also provides for the use of a peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, or SEQ ID No. 117 in the preparation of a medicament for down regulating a TLR4-mediated immune response. The immune response may be mediated through the activation of at least one MAP kinase or a transcription factors selected from NF-κB and at least one IRF. The IRF may be IRF3 or IRF7.

The invention further provides for a pharmaceutical composition comprising a therapeutically effective amount of a peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, or SEQ ID No. 117 and a pharmaceutically acceptable diluent, excipient or carrier.

The invention also provides for a method of prophylaxis and/or treatment of an immune-mediated condition comprising the step of administering an agent comprising a peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, SEQ ID No. 117, or peptidomimetic thereof to a subject wherein administration of the agent suppresses the activation of a MAP kinase or the transcription factors NF-κB and at least one IRF. The IRF may be IRF3 or IRF7. The immune mediated disorder may be an undesirable or aberrant immune response triggered by the activation of TLR4. The immune response may be directed to a self antigen. The immune response may be physiologically normal but is undesirable.

The immune mediated condition may be one or more selected from the group comprising: multiple sclerosis, rheumatoid arthritis, Crohn's disease, psoriasis, SLE, lupus, type I diabetes, colitis, inflammatory bowel disease, asthma, allergy diabetes mellitus, myasthenia gravis, systemic lupus erythematosis, autoimmune thyroiditis, dermatitis (including atopic dermatitis and eczematous dermatitis), Sjogren's Syndrome, including keratoconjunctivitis sicca secondary to Sjogren's Syndrome, alopecia areata, allergic responses due to arthropod bite reactions, aphthous ulcer, iritis, conjunctivitis, keratoconjunctivitis, ulcerative colitis, cutaneous lupus erythematosus, scieroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves ophthalmopathy, sarcoidosis, primary biliary cirrhosis, uveitis posterior, interstitial lung fibrosis, Alzheimer's disease and coeliac disease, or atopic disease.

The immune-mediated condition may be an autoimmune disease. The autoimmune disease may be one or more selected from the group comprising: multiple sclerosis, rheumatoid arthritis, Crohn's disease, psoriasis, SLE, lupus, type I diabetes, colitis, inflammatory bowel disease, asthma and allergy.

The invention further provides a method for down regulating an immune response of a subject following tissue transplantion comprising the step of administering an agent comprising a peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, SEQ ID No. 117, or peptidomimetic thereof to a subject.

The invention also provides a method of modulating intracellular signalling mediated by TLR4 comprising the step of administering a peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, or SEQ ID No. 117 to a subject.

The invention further provides for the use of an A464 peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, or SEQ ID No. 117 to modulate intracellular signalling mediated by TLR4 following the binding of a suitable agonist.

The invention also provides for a method for identifying a compound and/or substance suitable for modifying the biological activity of TLR4 comprising the steps of:
a) contacting a biological sample with a compound and/or substance to be tested in the presence of a peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No.

109, SEQ ID No. 110, SEQ ID No. 111, SEQ ID No. 112, SEQ ID No. 113, SEQ ID No. 114, SEQ ID No. 115, SEQ ID No. 116, or SEQ ID No. 117;

b) assaying the biological sample for a biological response; and c) comparing the biological response of a sample contacted with a compound and/or substance in the presence of a peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, or SEQ ID No. 117 to the biological response of a sample contacted with a compound and/or substance in the absence of the peptide.

The biological response may be one or more of MAP kinase activation, transcription factor activation and gene induction. The biological response may be inhibited by the presence of a peptide comprising the amino acid sequence of SEQ ID No. 4, SEQ ID No. 20, SEQ ID No. 38, SEQ ID No. 40, SEQ ID No. 41, SEQ ID No. 42, SEQ ID No. 55, SEQ ID No. 56, SEQ ID No. 57, SEQ ID No. 62, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No.79, SEQ ID No. 80, SEQ ID No. 81, SEQ ID No. 82, SEQ ID No. 83, SEQ ID No. 84, SEQ ID No.85, SEQ ID No. 86, SEQ ID No. 87, SEQ ID No. 88, SEQ ID No. 89, SEQ ID No. 90, SEQ ID No. 91, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, SEQ ID No. 101, SEQ ID No. 102, SEQ ID No. 103, SEQ ID No. 104, SEQ ID No. 105, SEQ ID No. 106, SEQ ID No. 107, SEQ ID No. 108, SEQ ID No. 109, SEQ ID No. 110, SEQ ID No. 111, SEQ ID No. 112, SEQ ID No. 113, SEQ ID No. 114, SEQ ID No. 115, SEQ ID No. 116, or SEQ ID No. 117.

The biological sample may be cultured cells. The biological sample may be a non-human animal.

The invention also provides for the use of a compound and/or substance identified by the method described herein as an adjuvant and/or booster of an immune response.

The invention further provides for a vaccine comprising a compound and/or a substance identified by the method described herein.

The invention further still provides for a composition comprising a compound and/or a substance identified by the method described herein and a pharmaceutically acceptable excipient.

In one embodiment, we describe a peptide comprising 11 amino acids derived from the vaccinia virus (VACV) protein A46, that when fused to a peptide delivery sequence, inhibits both murine and human Toll-like receptor 4 (TLR4) responses. One embodiment of the peptide, termed A464, has the amino acid sequence KYSFKLILAEYRRRRRRRRR (SEQ ID No. 20). The peptide is specific for TLR4 since other TLRs are not affected by it. We have also demonstrated that a peptide comprising the amino acid sequence SFKLIL (SEQ ID No. 55) can inhibit TLR4. Furthermore, we have also demonstrated that A464 (SEQ ID No. 20) has efficacy in vivo, to inhibit LPS-induced cytokine responses in mice.

In one aspect, the invention provides a peptide derived from vaccinia virus protein A46 for inhibiting Toll-like receptor 4 (TLR4) signalling. The peptide may comprise between 4 and 11 amino acids. The amino acid sequence of the peptide may be derived from the amino acid sequence of SEQ ID NO. 16.

The peptide may comprise the amino acid sequence of SEQ ID NO. 3, SEQ ID NO. 4, SEQ ID NO. 9, SEQ ID NO. 10, SEQ ID No. 54, or SEQ ID NO. 55 or a fragment, analogue or derivative thereof The amino acid sequence may be in the L-form, alternatively the amino acid sequence may be in the D-form.

The peptide may comprise a delivery sequence. The delivery sequence may be a cationic peptide. The delivery sequence may be between 8 and 16 amino acids in length. The delivery sequence may comprise the amino acid sequence of SEQ ID NO. 33, SEQ ID NO. 34, or SEQ ID NO. 35. The delivery sequence may be attached to the C terminus of the peptide. The delivery sequence may be attached to the N terminus of the peptide.

The invention further provides a peptide for inhibiting Toll-like receptor 4 (TLR4) signailing comprising the amino acid sequence of SEQ ID NO. 20, SEQ ID NO. 36, SEQ ID NO. 38, or SEQ ID NO. 57 or a fragment, analogue or derivative thereof.

The invention also provides for a peptide comprising the amino acid sequence of SEQ ID NO. 20 or a fragment, analogue or derivative thereof, a peptide comprising the amino acid sequence of SEQ ID NO. 36 or a fragment, analogue or derivative thereof, a peptide comprising the amino acid sequence of SEQ ID NO. 38 or a fragment, analogue or derivative thereof, and a peptide comprising the amino acid sequence of SEQ ID NO. 57 or a fragment, analogue or derivative thereof.

In another aspect the invention provides a peptidomimetic for inhibiting Toll-like receptor 4 (TLR4) signalling based on a peptide as described herein.

Further, the invention provides for a pharmaceutical composition comprising a peptide as described herein or a peptidomemetic as described herein and a pharmaceutically acceptable excipient.

The invention also provides for the use of a peptide or a peptidomimetic or a pharmaceutical composition as described herein to inhibit Toll-like receptor 4 (TLR4) signalling. The TLR4 signalling may be activated by a pathogen or pathogen component leading to a cytokine response. The TLR4 signalling protein activated may be one or more of NFκB, IκBα, IRF3 and p38. The pathogen may be a bacterium or a bacterial component such as lipopolysaccharide (LPS).

The invention also provides for a number of methods including:

A method of treatment or prophylaxis of a TLR4-associated disease comprising the step of administering an effective amount of a peptide or a peptidomimetic or a pharmaceutical composition as described herein to a subject. The disease may be a disease of the immune system and/or an inflammatory disease. The disease may be one or more of: sepsis, rheumatoid arthritis, colitis, multiple sclerosis, irritable bowel disease, cancer, sterile inflammation, pathogen-associated inflammation, kidney ischemia/reperfusion injury, liver ischemia/reperfusion injury, plaque development in atherosclerosis-prone subjects, and acute lung injury.

A method of inhibiting TLR4-induced cytokine responses comprising the step of administering an effective amount of a peptide comprising the amino acid sequence of SEQ ID NO. 3, SEQ ID NO. 4, SEQ ID NO. 9, SEQ ID NO. 10, SEQ ID NO. 20, SEQ ID NO. 36, SEQ ID NO. 38, SEQ ID NO. 54, SEQ ID NO. 55, or SEQ ID NO. 57 or a fragment, analogue or derivative thereof to a subject.

A method of inhibiting TLR4 induced responses comprising the step of administering an effective amount of a peptidomimetic based on the amino acid sequence of SEQ ID NO. 3, SEQ ID NO. 4, SEQ ID NO. 9, SEQ ID NO. 10, SEQ ID NO. 20, SEQ ID NO. 36, SEQ ID NO. 38, SEQ ID NO. 54, SEQ ID NO. 55, or SEQ ID NO. 57 or a fragment, analogue or derivative thereof to a subject.

A method of inhibiting TLR4 induced responses comprising the step of administering an effective amount of a pharmaceutical composition comprising a peptide having the amino acid sequence of SEQ ID NO. 3, SEQ ID NO. 4, SEQ ID NO. 9, SEQ ID NO. 10, SEQ ID NO. 20, SEQ ID NO. 36, SEQ ID NO. 38, SEQ ID NO. 54, SEQ ID NO. 55, or SEQ ID NO. 57 or a fragment, analogue derivative or peptidomimetic thereof and a pharmaceutically acceptable excipient to a subject.

A method of suppressing a pro-inflammatory immune response comprising the step of administering an effective amount of a peptide comprising the amino acid sequence of SEQ ID No.20 or an analogue, derivative, fragment, variant or peptidomimetic thereof thereof to a subject.

A method of prophylaxis and/or treatment of an immune-mediated condition comprising the step of administering an agent comprising a peptide comprising the amino acid sequence of SEQ ID No.20 or an analogue, derivative, fragment, variant or peptidomimetic thereof to a subject wherein administration of the agent suppresses the activation of a MAP kinase or the transcription factors NF-κB and at least one IRF. The IRF may be IRF3 or IRF7. The immune mediated disorder may be an undesirable or aberrant immune response triggered by the activation of TLR4. The immune response may be directed to a self antigen. The immune response may be physiologically normal but undesirable.

The immune mediated condition may be one or more selected from the group comprising: multiple sclerosis, rheumatoid arthritis, Crohn's disease, psoriasis, SLE, lupus, type I diabetes, colitis, inflammatory bowel disease, asthma, allergy diabetes mellitus, myasthenia gravis, systemic lupus erythematosis, autoimmune thyroiditis, dermatitis (including atopic dermatitis and eczematous dermatitis), Sjogren's Syndrome, including keratoconjunctivitis sicca secondary to Sjogren's Syndrome, alopecia areata, allergic responses due to arthropod bite reactions, aphthous ulcer, iritis, conjunctivitis, keratoconjunctivitis, ulcerative colitis, cutaneous lupus erythematosus, scieroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves ophthalmopathy, sarcoidosis, primary biliary cirrhosis, uveitis posterior, interstitial lung fibrosis, Alzheimer's disease and coeliac disease, or atopic disease.

The immune-mediated condition may be an autoimmune disease such as an autoimmune disease selected from one or more of the group comprising: multiple sclerosis, rheumatoid arthritis, Crohn's disease, psoriasis, SLE, lupus, type I diabetes, colitis, inflammatory bowel disease, asthma and allergy.

The invention further provides a method for down regulating an immune response of a subject following tissue transplantion comprising the step of administering an agent comprising a peptide comprising the amino acid sequence of SEQ ID No.20 or an analogue, derivative, fragment, variant or peptidomimetic thereof to a subject.

The invention also provides a method of modulating intracellular signalling mediated by TLR4 comprising the step of administering a peptide comprising the amino acid sequence of SEQ ID No.20 or a derivative, fragment, or variant thereof to a subject.

In a different aspect the invention provides for the use of a peptide comprising the amino acid sequence of SEQ ID No.20 or a fragment, analogue or derivative thereof to suppress an immune response wherein the immune response is mediated through the stimulation of TLR4 leading to the activation of a MAP kinase, or at least one transcription factor selected from NF-κB and at least one IRF. The IRF may be IRF3 or IRF7.

The invention further provides for the use of a peptide comprising the amino acid sequence of SEQ ID No.20 or a fragment, analogue or derivative thereof in the preparation of a medicament for down regulating a TLR4-mediated immune response. The immune response may be mediated through the activation of at least one MAP kinase or a transcription factors selected from NF-κB and at least one IRF. The IRF may be IRF3 or IRF7.

The invention also provides a pharmaceutical composition comprising a therapeutically effective amount of a peptide comprising the amino acid sequence of SEQ ID No.20 or a fragment, analogue or derivative thereof and a pharmaceutically acceptable diluent, excipient or carrier.

The invention further provides for the use of a peptide comprising the amino acid sequence of SEQ ID No.20 or a variant, derivative or fragment thereof to modulate intracellular signalling mediated by TLR4 following the binding of a suitable agonist.

In a further aspect, the invention provides a method for identifying a compound and/or substance suitable for modifying the biological activity of TLR4 comprising the steps of:
  (a) contacting a biological sample with a compound and/or substance to be tested in the presence and absence of a peptide comprising the amino acid sequence of SEQ ID No. 20 or a fragment, analogue or derivative thereof;
  (b) assaying the biological sample for a biological response; and
  (c) comparing the biological response of a sample contacted with a compound and/or substance in the presence of a peptide comprising the amino acid sequence of SEQ ID No. 20 or a fragment, analogue or derivative thereof to the biological response of a sample contacted with a compound and/or substance in the absence of a peptide comprising the amino acid sequence of SEQ ID No. 20 or a fragment, analogue or derivative thereof.

The biological response may be one or more of MAP kinase activation, transcription factor activation and gene induction. The biological response may be inhibited by the presence of a peptide comprising the amino acid sequence of SEQ ID No. 20 or a fragment, analogue or derivative thereof.

The biological sample may be cultured cells. Alternatively, the biological sample may be a non-human animal.

The invention further provides for the use of a compound and/or substance identified by the method described herein as an adjuvant and/or booster of an immune response.

The invention also provides a vaccine comprising a compound and/or a substance identified by the method described herein.

The invention further provides a composition comprising a compound and/or a substance identified by the method described herein and a pharmaceutically acceptable excipient.

The invention also provides a peptide having between 4 to 27 amino acids comprising the amino acid sequence of SEQ ID No. 54, SEQ ID No. 55 or SEQ ID No. 4.

Pharmaceutical Compositions

The invention extends in various aspects not only to a substance identified as a peptide, in accordance with what is disclosed herein, but also a pharmaceutical composition, medicament, drug or other composition comprising such a substance, a method comprising administration of such a composition to a patient, e.g. for treatment (which may include preventative treatment) to suppress an immune response mediated by TLR4, and a method of making a pharmaceutical composition comprising admixing such a substance with a pharmaceutically acceptable excipient, vehicle or carrier, and optionally other ingredients known to those skilled in the art. Such ingredients should be non-toxic and should not interfere with the efficacy of the active ingredient. The precise nature of the carrier or other material will depend on the route of administration, which may be, for example, oral, intravenous, intranasal or via oral or nasal inhalation.

The formulation may be a liquid, for example, a physiologic salt solution containing non-phosphate buffer at pH 6.8-7.6, or a lyophilised or freeze dried powder.

Mimetics

Non-peptide "small molecules" are often preferred for many in-vivo pharmaceutical uses.

Accordingly, a mimetic or mimic of the substance may be designed for pharmaceutical uses. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

Peptidomimetics

Whilst numerous strategies to improve the pharmaceutical properties of peptides found to exert biological effects are known in the art including, for example, amide bond replacements, incorporation of non-peptide moieties, peptide small molecule conjugates or backbone cyclisation, the optimisation of pharmacological properties for particular peptides still presents those involved in the optimisation of such pharmaceutical agents with considerable challenges.

Peptides of and for use in the invention may be modified such that they comprise amide bond replacement, incorporation of non peptide moieties, or backbone cyclisation. Suitably if cysteine is present the thiol of this residue is capped to prevent damage of the free sulphate group. Suitably a peptide of and for use in the invention may be modified from the natural sequence to protect the peptides from protease attack. Suitably a peptide of and for use in the invention may be further modified using at least one of C and/or N-terminal capping, and/or cysteine residue capping. Suitably a peptide of and for use in the invention may be capped at the N terminal residue with an acetyl group. Suitably a peptide of and for use in the invention may be capped at the C terminal with an amide group. Suitably the thiol groups of cysteines are capped with acetamido methyl groups.

Non-peptide "small molecules" are often preferred for many in vivo pharmaceutical uses. Accordingly, a peptidomimetic or mimic of the substance (particularly a peptide) may be designed for pharmaceutical uses. The designing of peptidomimetics to a known pharmaceutically active peptide is a known approach to the development of pharmaceuticals based on a "lead" compound. This might be desirable where the active compound is difficult or expensive to synthesise of where it is unsuitable for a particular method of administration, e.g. peptides are not well suited as active agents for oral compositions as they tend to quickly degraded by proteases in the alimentary canal. Peptidomimetic design, synthesis and testing may be used to avoid randomly screening large number of molecules for a target property.

As used herein, a mimetic or peptidomimetic is a compound that is capable of mimicking a peptide. Peptidomimetics are generally not substrates of proteases and are likely to be active in vivo for a longer period of time as compared to the peptide on which they are based. In addition, peptidomimetics may be less antigenic and show an overall higher bioavailability.

There are several steps commonly taken in the design of a peptidomimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the led compound. The peptidomimetic or peptidomimetics found by this approach can then be screened to see whether they have the target property, or to what extent they exhibit it. Further optimisation or modification can then be carried out to arrive at one or more final peptidomimetic for in vivo or clinical testing.

Fragments

The term "fragment" used herein means two or more consecutive amino acid residues of a peptide sequence from which the fragment is derived. A fragment retains the biological activity of the peptide from which it is derived. For example SEQ ID No. 68 and SEQ ID No. 62 can be considered as fragments of SEQ ID No. 4 and SEQ ID No. 20.

Analogues and Derivatives

The invention extends to peptides which are derivates or homologues of A464 (SEQ ID No. 20).

Thus, an analogue, homologue or derivative of any one of the peptides of the invention may include 1, 2, 3, 4, 5 or greater than 5 amino acid alterations.

As is well understood, homology at the amino acid level is generally in terms of amino acid similarity or identity. Similarity allows for 'conservative variation', such as substitution of one hydrophobic residue such as isoleucine, valine, leucine or methionine for another, or the substitution of one polar residue for another, such as lysine, glutamic acid for aspartic acid, or glutamine for asparagine.

Analogues of, and for use in, the invention as defined herein means a peptide modified by varying the amino acid sequence. Such derivatives of the amino acid sequence may involve insertion, addition, deletion and/or substitution for example conservative substitution of one or more amino acids.

Treatment/Therapy

The term 'treatment' is used herein to refer to any regime that can benefit a human or non-human animal. The treatment may be in respect of an existing condition or may be prophylactic (preventative treatment). Treatment may include curative, alleviation or prophylactic effects.

More specifically, reference herein to "therapeutic" and "prophylactic" treatment is to be considered in its broadest context. The term "therapeutic" does not necessarily imply that a subject is treated until total recovery. Similarly, "prophylactic" does not necessarily mean that the subject will not eventually contract a disease condition.

Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition. "Therapeutic" may also reduce the severity of an existing condition.

Administration

Peptides or derivatives thereof for use in the invention may be administered alone but will preferably be administered as a pharmaceutical composition, which will generally comprise a suitable pharmaceutical excipient, diluent or carrier selected depending on the intended route of administration.

Peptides or derivatives thereof for use in the invention may be administered to a patient in need of treatment via any suitable route. The precise dose will depend upon a number of factors, including the precise nature of the form of peptide to be administered.

Route of administration may include; parenterally (including subcutaneous, intramuscular, intravenous, by means of, for example a drip patch), some further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebuliser or inhaler, or by an implant.

In preferred embodiments, the composition is deliverable as an injectable composition, is administered orally, or is administered to the lungs as an aerosol via oral or nasal inhalation.

For administration via the oral or nasal inhalation routes, preferably the active ingredient will be in a suitable pharmaceutical formulation and may be delivered using a mechanical form including, but not restricted to an inhaler or nebuliser device.

For intravenous injection, the active ingredient will be in the form of a parenterally acceptable aqueous solution which is pyrogen-free and has suitable pH, isotonicity and stability.

Those of relevant skill in the art are well able to prepare suitable solutions using, for example, isotonic vehicles such as sodium chloride injection, Ringer's injection, Lactated Ringer's injection.

Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The composition may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3, 773, 919; EP-A-0058481) copolymers of L-glutamic acid and gamma ethyl-L-glutamate (Sidman et al, Biopolymers 22(1): 547-556, 1985), poly (2-hydroxyethyl-methacrylate) or ethylene vinyl acetate (Langer et al, J. Biomed. Mater. Res. 15: 167-277, 1981, and Langer, Chem. Tech. 12:98-105, 1982).

Examples of the techniques and protocols mentioned above and other techniques and protocols which may be used in accordance with the invention can be found in Ansel's Pharmaceutical Dosage Forms and Drug Delivery Systems, 8$^{th}$ Edition ISBN 0-781746-12-4, pages 186-505 and 653-671, the entire disclosures of which is herein incorporated by reference.

Dose

Peptides or derivatives thereof according to the invention is preferably administered to an individual in a "therapeutically effective amount", this being sufficient to show benefit to the individual.

The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

The optimal dose can be determined by physicians based on a number of parameters including, for example, age, sex, weight, severity of the condition being treated, the active ingredient being administered and the route of administration.

A "subject" in the context of the invention includes and encompasses mammals such as humans, primates and livestock animals (e.g. sheep, pigs, cattle, horses, donkeys); laboratory test animals such as mice, rabbits, rats and guinea pigs; and companion animals such as dogs and cats. It is preferred for the purposes of the invention that the mammal is a human.

Preferred features and embodiments of each aspect of the invention are as for each of the other aspects mutatis mutandis unless the context demands otherwise.

Unless otherwise defined, all technical and scientific terms used herein have the meaning commonly understood by a person who is skilled in the art in the field of the invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

The term "consists essentially of" or "consisting essentially of" as used herein means that a polypeptide may have additional features or elements beyond those described provided that such additional features or elements do not materially affect the ability of the polypeptide to function as a specific inhibitor of TLR4 responses. That is, the polypeptide may have additional features or elements that do not interfere with specific inhibition of TLR4 responses. For example, a polypeptide consisting essentially of a specified sequence may contain one, two, three, four, five or more additional amino acids, at either end or at both ends of the sequence provided that the additional amino acids do not interfere with, inhibit, block or interrupt the specific inhibition of TLR4 responses. Similarly, a polypeptide molecule may be chemically modified with one or more functional groups provided that such chemical groups do not interfere with, inhibit, block or interrupt the specific inhibition of TLR4 responses.

BRIEF DESCRIPTION OF THE DRAWINGS

The invention will be more clearly understood from the following description of an embodiment thereof, given by way of example only, with reference to the accompanying drawings, in which.

Figure 11:
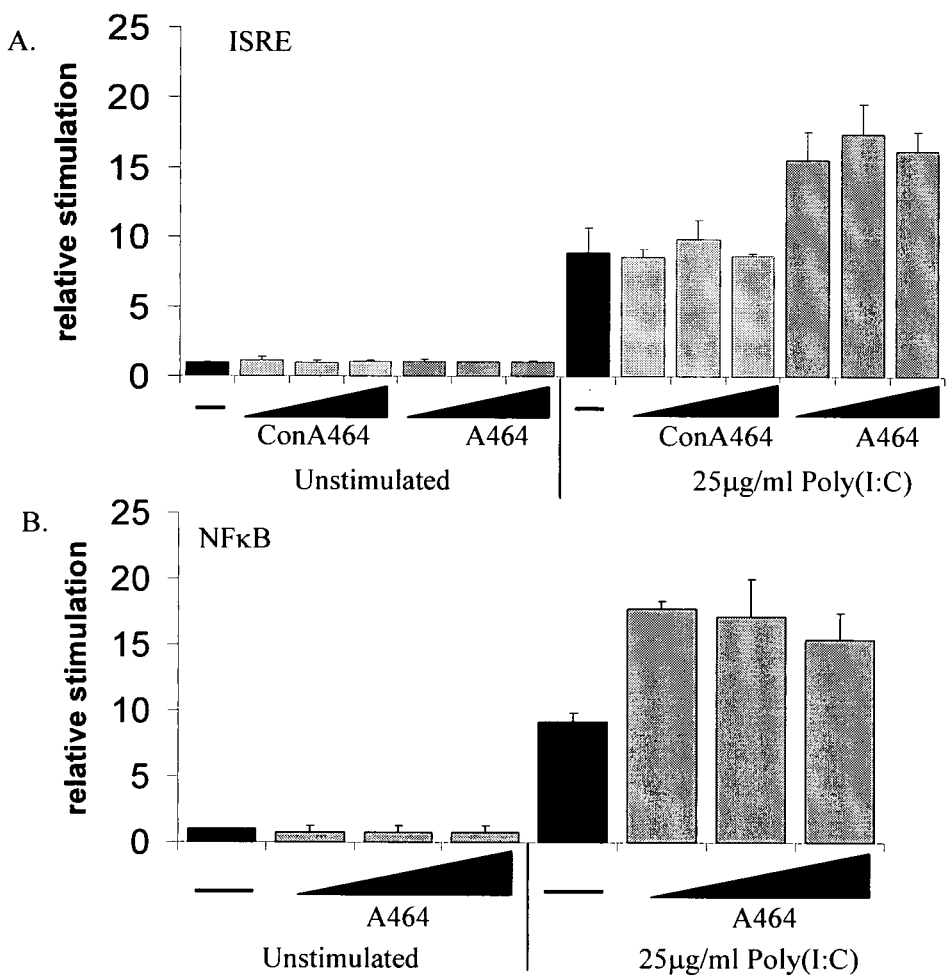
FIGS. 11A and B are bar charts showing the effect of A464 and scrambled A464 (ConA464) on poly(I:C)-induced TLR3 signalling in HEK293 cells. HEK293_TLR3 cells were seeded in 96 well plates ($1.5 \times 10^5$ cells/ml) 24 hours before transfection with the plasmid DNA. Cells were transfected with 60 ng of either ISRE-Luciferase (A) or NFκB-Luciferase (B) and 20 ng of TK-Renilla reporter gene plasmids. The total volume of plasmid DNA transfected into the cells was made up to 230 ng by adding pcDNA.
Figure 12:
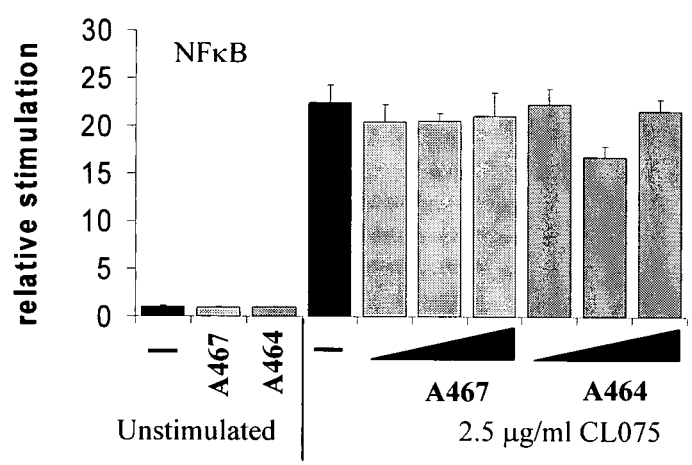
Figure 13:
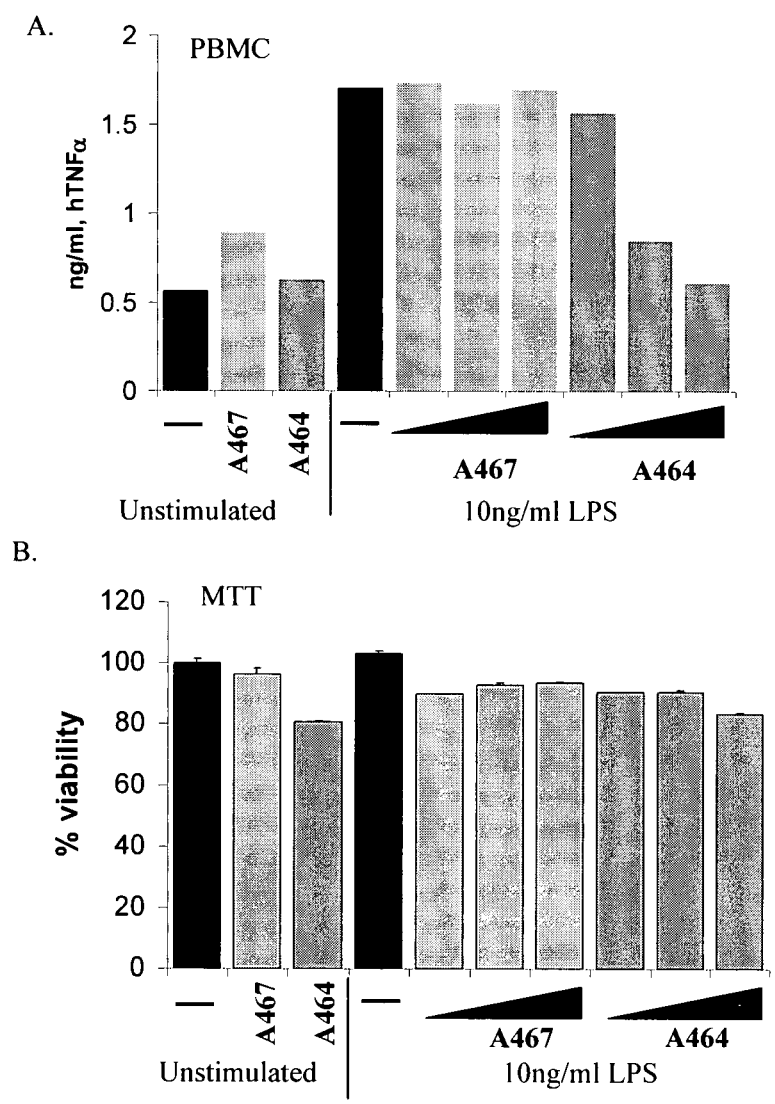
Figure 15:
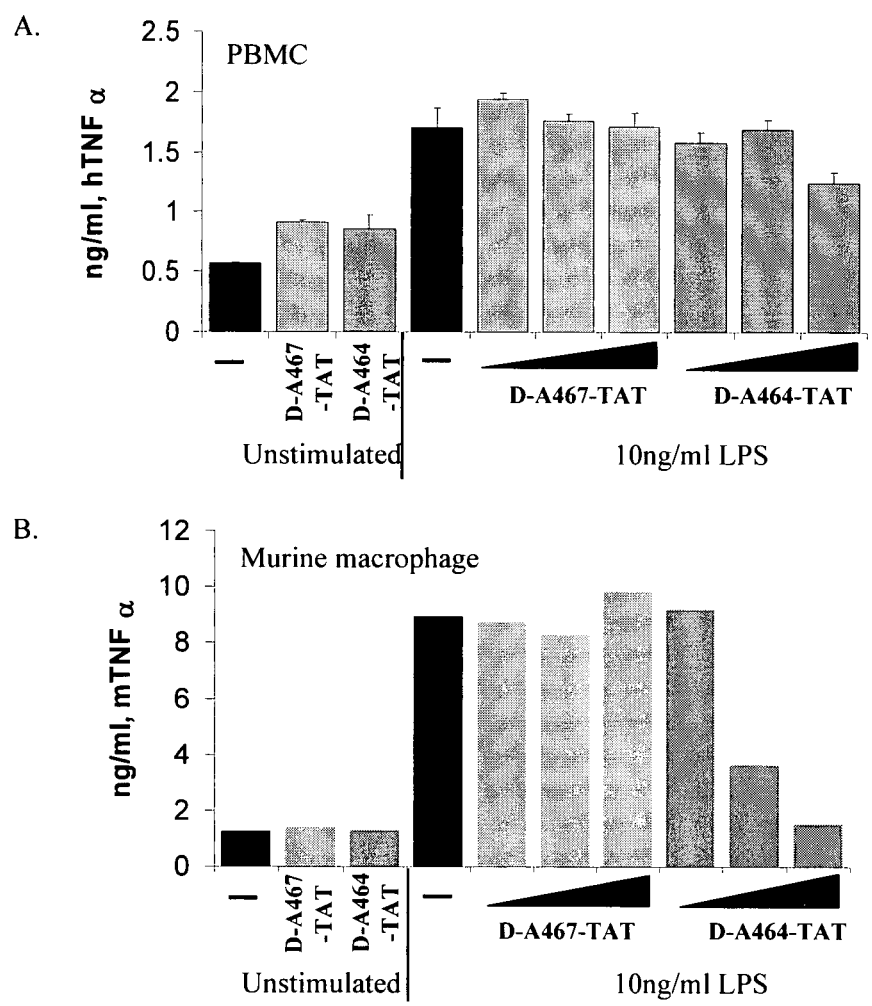
Figure 21:
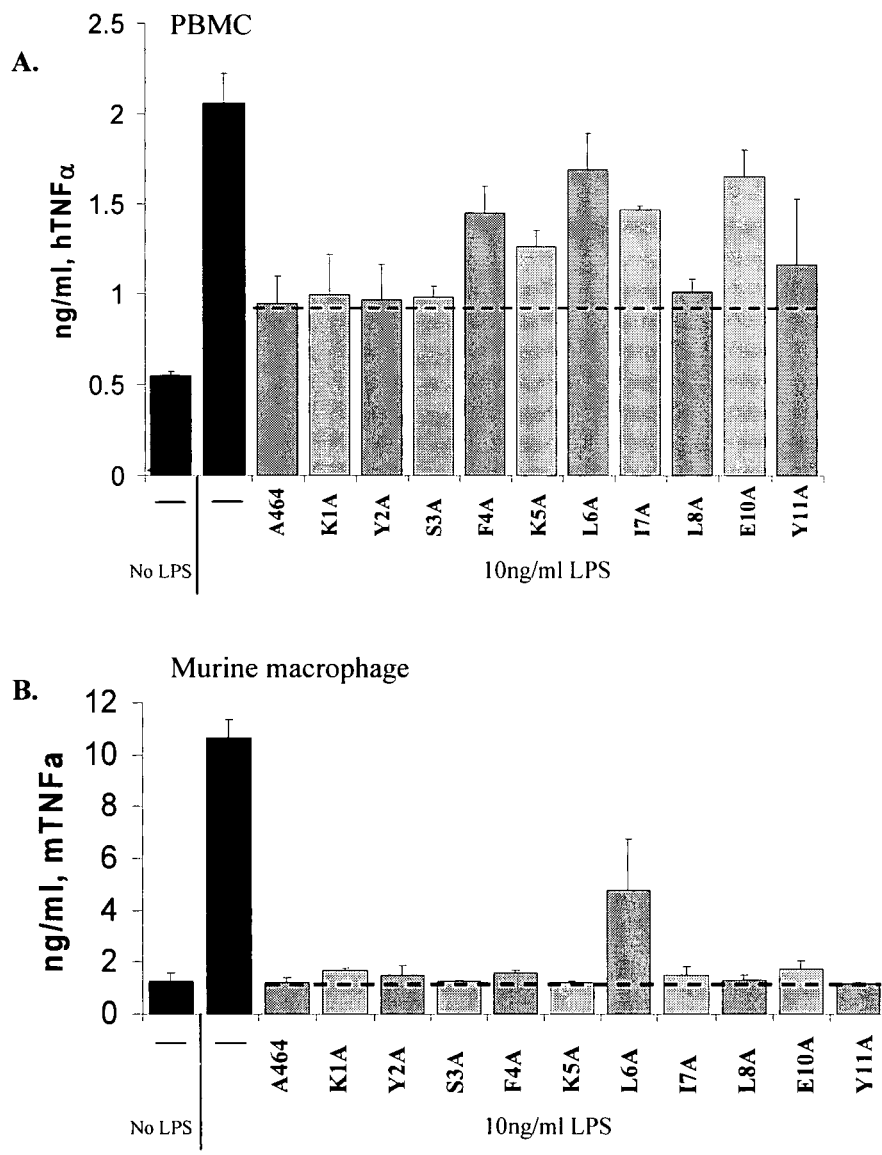
Figure 23:
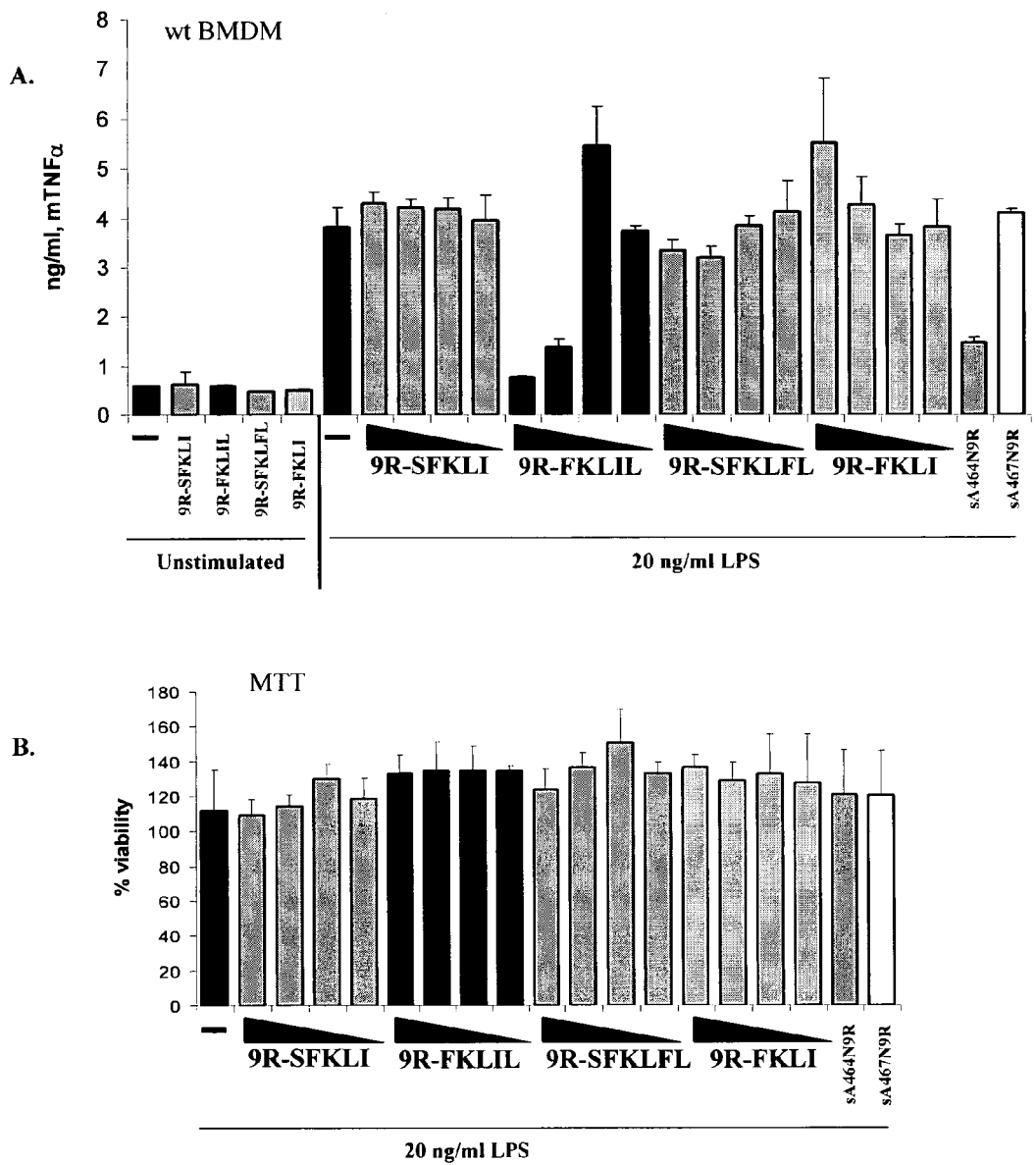

Scrambled A464 (ConA464) (SEQ ID NO. 32) and A464 (SEQ ID NO. 20) peptides were added to the cells at a concentration of 2, 5 or 10 μM the next day and cells were stimulated with 25 μg/ml poly(I:C) 1 hour after treatment with the peptide. Cells were harvested and reporter gene assays performed 6 hr after stimulation with the agonist. No peptides were added to the control wells (black bars). Data is representative of at least three experiments each performed in triplicate. Data are expressed as mean fold induction±s.d. relative to control levels;

FIG. 12 is a bar chart showing the effect of A467 and A464 on TLR8-induced NFκB activation in HEK293 cells. HEK293_TLR8 cells were transfected with 60 ng NFκB-Luciferase and 20 ng of TK-Renilla reporter genes, as in FIG. 11. A467 (SEQ ID NO. 23) and A464 (SEQ ID NO. 20) were added to the cells at a concentration of 1, 5 or 25 μM the next day and cells were stimulated with 2.5 μg/ml CL075 1 hour after treatment with the peptide. Cells were harvested and assayed for NFκB activation by reporter gene assay 6 hr after stimulation with the agonist. No peptides were added to the control wells (black bars). Data is representative of at least three experiments each performed in triplicate. Data are expressed as mean fold induction±s.d. relative to control levels;

FIGS. 13A and B are bar charts showing the effect of A467 and A464 on LPS-induced TNFα production and on cell viability in primary human cells. Peripheral blood mononuclear cells (PBMCs) were seeded in 96 well plates ($1 \times 10^6$ cells/ml) 24 hours before treatment. A467 (SEQ ID NO. 23) and A464 (SEQ ID NO. 20) were added to the cells at 1, 5 and 25 μM 1 hour before stimulating with 10 ng/ml LPS. The peptides were added into the unstimulated control wells at 25 μM. Supernatants were collected 6 hours after stimulation and assayed for TNFα production by ELISA (A). The cells were assayed for viability by the MTT assay (B). No peptides were added to the control wells (black bars). Data is representative of at least three experiments each performed in triplicate and is expressed as mean±s.d;

FIGS. 14A and B are bar charts showing the comparison of the inhibitory effect of the L- and D-forms of A464 on LPS-induced TNFα in primary human and murine cells. PBMC ($1 \times 10^6$ cells/ml, (A)) or immortalised murine macrophages ($1.5 \times 10^5$ cells/ml, (B)) were seeded in 96 well plates 24 hours before treatment. L-form and D-form A464 peptides (with the 9R delivery peptide on the C-terminus, SEQ ID NO. 20) were added to the cells at a concentration of 1, 5 or 25 μM 1 hour before stimulating with 10 ng/ml LPS. Supernatants were collected 6 hours after stimulation and assayed for either human (A) or murine (B) TNFα production by ELISA. No peptides were added to the control wells (black bars). Data is representative of at least three experiments each performed in triplicate and is expressed as mean±s.d;

FIGS. 15A and B are bar charts showing the effect of the D-form A464 peptide with the TAT delivery sequence on LPS induced TNFα in primary human and murine cells. PBMC (A) and immortalised murine macrophages (B) were seeded in 96 well plates 24 hours before treatment. D-form of A467 (SEQ ID NO. 37) and A464 (SEQ ID NO. 36) with the TAT delivery sequence were added to the cells at a concentration of 1, 5 or 25 μM 1 hour before stimulating with 10 ng/ml LPS. The peptides were added into the unstimulated control wells at 25 μM. Supernatants were collected 6 hours after stimulation and assayed for either human (A) or murine (B) TNFα production by ELISA. No peptides were added to the control wells (black bars). Data is representative of at least three experiments each performed in triplicate and is expressed as mean±s.d;

FIGS. 16A and B are bar charts showing the effect of attaching 9R to the N-terminus of A464 on LPS-induced TNFα in primary human and murine cells. Immortalised murine macrophages (A) and PBMC (B) were seeded in 96 well plates 24 hours before treatment. L-form of A467 (SEQ ID NO. 39) and A464 (SEQ ID NO. 38) with the 9R-delivery sequence at the N-terminus were added to the cells at a concentration of 1, 5 or 25 μM 1 hour before stimulating with 10 ng/ml LPS. The peptides were added into the unstimulated control wells at 25 $_R$M. Supernatants were collected 6 hours after stimulation and assayed for either murine (A) or human (B) TNFα production by ELISA. No peptides were added to the control wells (black bars). Data is representative of at least three experiments each performed in triplicate and is expressed as mean±s.d;

FIGS. 17A and B are bar charts showing the effect of the D-form A464 with 9R at the N-terminus on LPS-induced TNFα in primary human and murine cells. Immortalised murine macrophages (A) and PBMC (B) were seeded in 96 well plates 24 hours before treatment. D-form of A467 (SEQ ID NO. 39) and A464 (SEQ ID NO. 38) peptides with the 9R-delivery sequence at N-terminus were added to the cells at a concentration of 1, 5 or 25 μM 1 hour before stimulating with 10 ng/ml LPS. The peptides were added into the unstimulated control wells at 25 μM. Supernatants were collected 6 hours after stimulation and assayed for either murine (A) or human (B) TNFα production by ELISA. No peptides were added to the control wells (black bars). Data is representative of at least three experiments each performed in triplicate and is expressed as mean±s.d;

FIGS. 18A and B are bar charts showing the effect of shortened A464 peptides with deletions of N- and C-terminal amino acids on LPS-induced TNFα in murine macrophages. Immortalised murine macrophages were seeded in 96 well plates ($1.5 \times 10^5$ cells/ml) 24 hours before treatment. A464 peptides with a deletion of one (N-1) (SEQ ID NO. 40) or two (N-2) (SEQ ID NO. 41) amino acids from the N-terminus (A), or three (C-3) (SEQ ID NO. 42) or six (C-6) (SEQ ID NO. 43)

amino acids from the C-terminus (B), were added to the cells at a concentration of 1, 5 or 25 µM 1 hour before stimulating with 10 ng/ml LPS. Peptides were added to the control wells at 25 µM. Normal full-length A464 (SEQ ID NO. 20) was used at 5 µM as a positive control. Supernatants were collected 6 hours after stimulation and assayed for TNFα by ELISA. No peptides were added to the control wells (black bars). Data is representative of at least three experiments each performed in triplicate and is expressed as mean±s.d;

FIGS. 19A and B are bar charts showing the effect of shortened A464 peptides with deletions of N- and C-terminal amino acids on LPS-induced TNFα in human PBMC. A464 peptides with a deletion of one (N-1) (SEQ ID NO. 40) or two (N-2) (SEQ ID NO. 41) amino acids from the N-terminus (A), or three (C-3) (SEQ ID NO. 42) or six (C-6) (SEQ ID NO. 43) amino acids from the C-terminus (B), were added to the cells at a concentration of 1, 5 or 25 µM 1 hour before stimulating with 10 ng/ml LPS. Peptides were added to the control wells at 25 µM. Normal full-length A464 (SEQ ID NO. 20) was used at 5µM as a positive control. Supernatants were collected 6 hours after stimulation and assayed for TNFα by ELISA. No peptides were added to the control wells (black bars). Data is representative of at least three experiments each performed in triplicate and is expressed as mean±s.d;

FIGS. 20A and B are bar charts showing the effect of shortened A464 peptides with deletions of N- and C-terminal amino acids on TLR4- and TLR3-induced NFκB activation in HEK293 cells. HEK293_TLR4 (A) and HEK293_TLR3 (B) cells were seeded in 96 well plates ($1.5 \times 10^5$ cells/ml) 24 hours before transfection with the plasmid DNA. Cells were transfected with 60 ng NFκB-Luciferase and 20 ng of TK-Renilla reporter genes, as in FIG. 11. A464N-2 (SEQ ID NO. 41) and A464C-3 (SEQ ID NO. 42) peptides were added to the cells at a concentration of 1, 5 or 25 µM the next day and cells were stimulated with either 10 ng/ml LPS (A) or 25 µg/ml Poly(I:C) (B) 1 hour after treatment with peptides. Cells were harvested and assayed for NFκB activation by reporter gene assay 6 hours after stimulation with the agonists. No peptides were added to the control wells (black bars). Data is representative of three experiments each performed in triplicate and is expressed as mean fold induction±s.d. relative to control levels;

FIGS. 21A and B are bar charts showing the results of an alanine scan of A464 in human PBMC and murine macrophages. Primary human PBMC ($1 \times 10^6$ cells/ml, (A)) and immortalised murine macrophages ($1.5 \times 10^5$ cells/ml, (B)) were seeded in 96 well plates 24 hours before treatment. Peptides with an Alanine substitution at each position in A464 (SEQ ID NO. 44 to 53) were added to the cells at a concentration 5 µM 1 hour before stimulating with 10 ng/ml LPS. Supernatants were collected 6 hours after stimulation with the agonist and assayed for human (A) and murine (B) TNFα by ELISA. Normal A464 (SEQ ID NO. 20) peptide was used at 5 µM as a positive control. No peptides were added to the control wells (black bars). Data is representative of at least three experiments each performed in triplicate and is expressed as mean±s.d;

FIGS. 22A and B are bar charts showing the effect of short A467 and A464 peptides, with 9R on either N- or C-terminus, on LPS- induced TNFα production in murine RAW264.7 cells. Cells were seeded in 96 well plates ($1.5 \times 10^5$ cells/ml) 24 hours before treatment. Short A467 and short A464 peptides with the 9R delivery sequence on either the C-terminus (sA464C9R) (SEQ ID NO. 56) (A) or the N-terminus (sA464N9R) (SEQ ID NO. 57) (B) were added to the cells at a concentration of 5 or 25 µM 1 hour before stimulating with 10 ng/ml LPS. Normal full length A467 (SEQ ID NO. 23) and A464 (SEQ ID NO. 20) peptides were added at a concentration of 5 µM as positive controls. Supernatants were collected 6 hours after stimulation with the agonist and assayed for TNFα, by ELISA. No peptides were added to the control wells (black bars). Data is representative of at least three experiments each performed in triplicate and is expressed as mean±s.d;

FIG. 23A is a bar chart showing the effect of shorter versions of sA464N9R (SEQ ID NO. 57) peptide on TLR4-induced murine TNFα in immortalised murine macrophages. BMDM cells were seeded in 96 well plates ($1.5 \times 10^5$ cells/ml) 24 hours before treatment. Short peptide sA464N9R (SEQ ID NO. 57) with a deletion of one amino acid from either N-terminus (9R-FKLIL) (SEQ ID NO. 62) or C-terminus (9R-SFKLI) (SEQ ID NO. 63) or both (9R-FKLI) (SEQ ID NO. 64) and one with substitution of Isoleucine (I) to Phenylalanine (F) (9R-SFKLFL) (SEQ ID NO. 65), were added to the cells at 1, 3, 6.25 and 12.5 µM 1 hour before stimulating with 20 ng/ml LPS. Peptides were added to the control wells at 50 µM. Short sA464N9R (SEQ ID NO. 57) was used at 12.5 µM as positive control and sA467N9R was used as negative control. Supernatants were collected 6 hours after stimulation and assayed for TNFα by ELISA. No peptides were added to the control wells (black bars). The cells were also assayed for viability by the MTT assay (FIG. 23B). Data is representative of at least three experiments each performed in triplicate and is expressed as mean±s.d.

Figure 25:
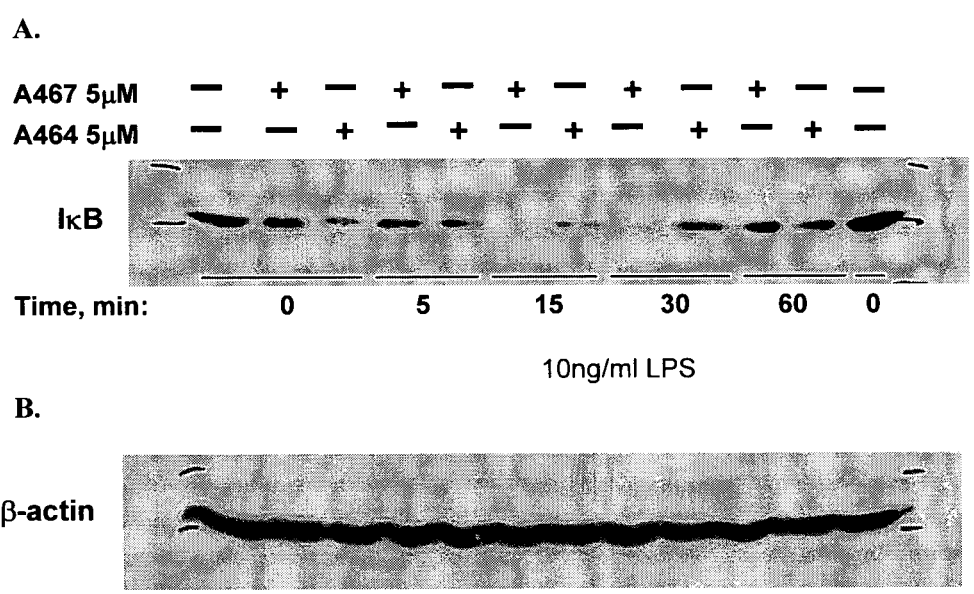
Figure 26:
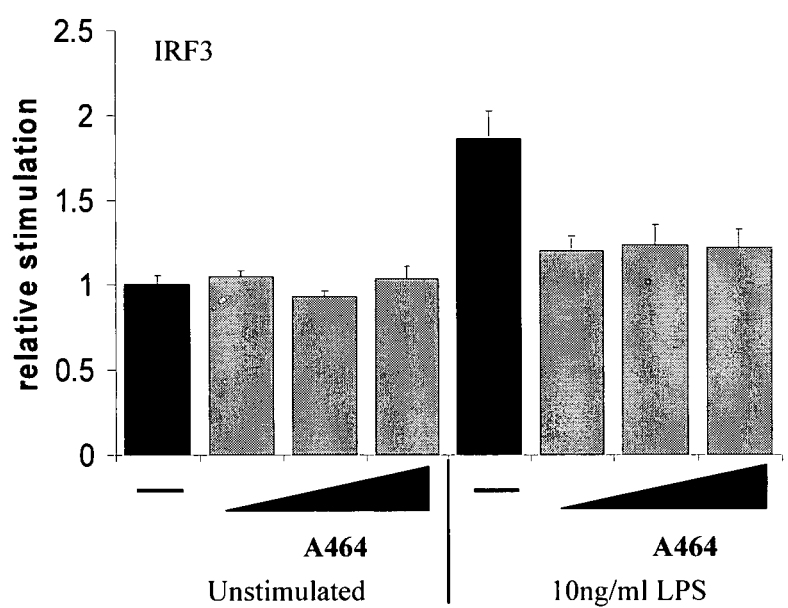

FIGS. 24A and B are bar charts showing the effect of A464 on ligand-independent TLR4 signalling in HEK293 cells. HEK293_TLR4 cells were seeded in 96 well plate ($1.5 \times 10^5$ cells/ml) 24 hours before transfection with NFκB-luciferase and TK-Renilla reporter gene plasmids. NFκB activation was stimulated by transfecting either 50 or 100 ng of CD4/TLR4-encoding plasmid or by stimulating with 10 ng/ml LPS. The total amount of plasmid DNA transfected into the cells was made up to 230ng by adding pcDNA. A464 (SEQ ID NO. 20) was added to the cells at a concentration of 5 or 25 µM 2 hours (A) or 9 hours (B) after the transfection or LPS-stimulation. Cells were harvested and assayed for NFκB activation by reporter gene assay 24 hours post-transfection. No peptides were added to the control wells (black bars). Data is representative of two experiments, each performed in triplicate and is expressed as mean fold induction±s.d. relative to control levels;

FIGS. 25A and B are immunoblots showing the effect of A464 on LPS-induced IκBα degradation in murine RAW264.7 cells. Cells were seeded in 6-well plates at 1.5× 105 cells/ml 24 hours prior to treatment with peptides. A467 (SEQ ID NO. 23) and A464 (SEQ ID NO. 20) were then added to the wells 1 hour before stimulation at a concentration of 5 µM. Cells were stimulated with 10 ng/ml LPS for a period of 5, 15, 30 or 60 min and then harvested on ice and lysed in 1% NP-40 containing lysis buffer. Lysates then were denatured using 5× sample buffer with DTT and resolved by SDS-PAGE. The proteins were transferred to PVDF membrane and the membrane was immunoblotted for IκBα (A). Equal protein loading was confirmed by re-probing the blot for β-actin (B). The blots shown are representative of two experiments;

FIG. 26 is a bar chart showing the effect of A464 on LPS-induced IRF3 activation in HEK293 cells. HEK293_TLR4 cells were seeded in 96 well plate ($1.5 \times 10^5$ cells/ml) 24 hours before transfection with the plasmid DNA. Cells were transfected with a plasmid encoding IRF3-GAL4, together with pFR-luciferase and TK-Renilla reporter gene plasmids. The total amount of plasmid DNA transfected into the cells was made up to 230 ng/well by adding pcDNA. A464

Figure 28:
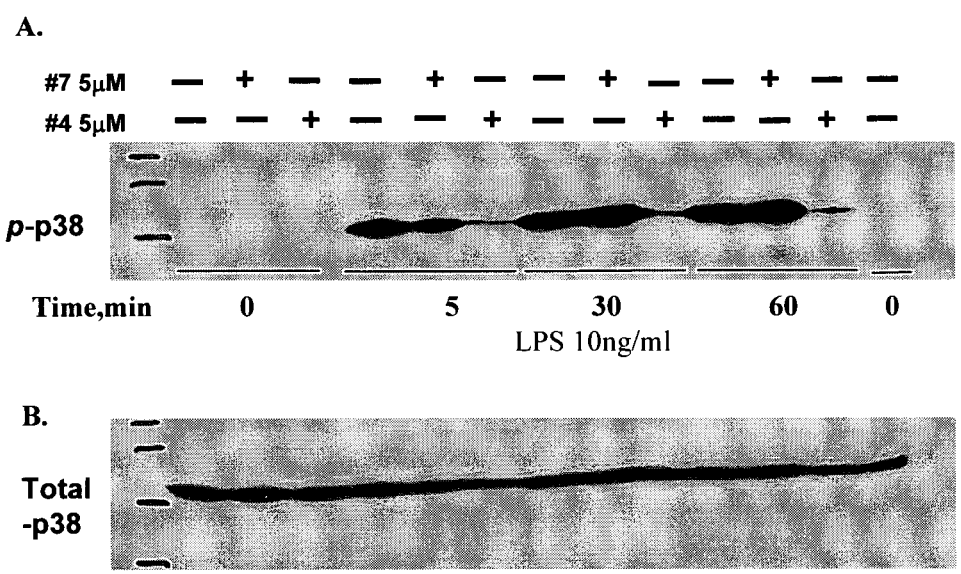
Figure 29:
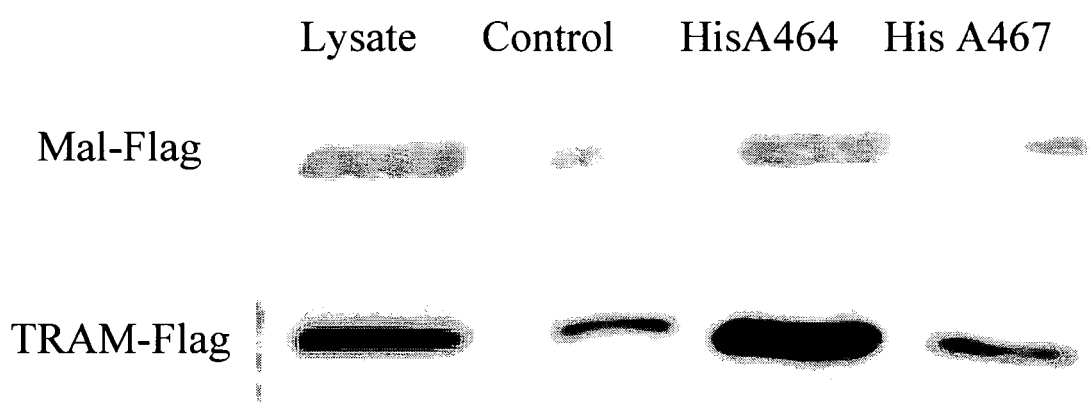
Figure 30:
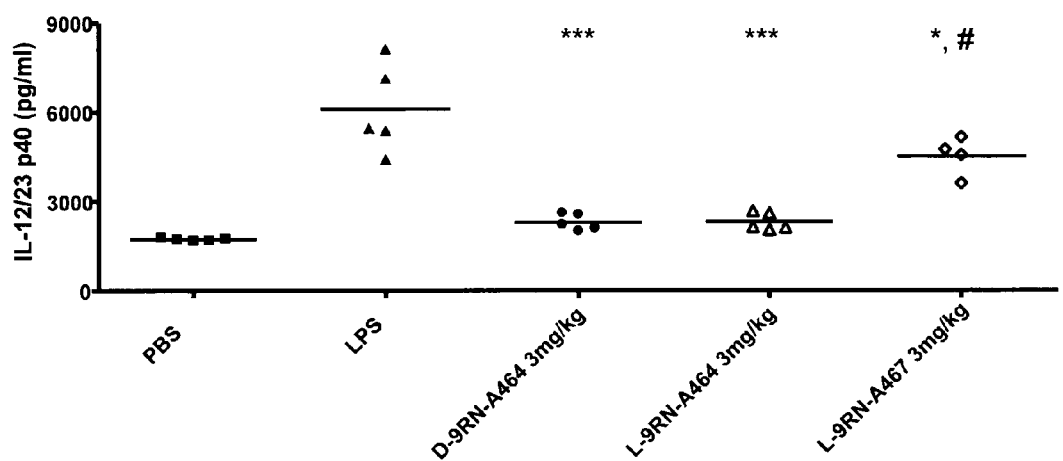

(SEQ ID NO. 20) was added to the cells at a concentration of 1, 5 or 10 µM the next day, and cells were stimulated with 10 ng/ml LPS 1 hour after treatment with the peptide for 6 hours. Cells were harvested and assayed for IRF3 activation by reporter gene assay. No peptides were added to the control wells (black bars). Data is representative of two experiments, each performed in triplicate and is expressed as mean fold induction±s.d. relative to control levels;

FIGS. 27A, B and C are immunoblots showing the effect of A464 on LPS-induced appearance of phospho-JNK in murine RAW264.7 cells. Cells were set up as for FIG. 25 above and 5 µM A467 (SEQ ID NO. 23) or A464 (SEQ ID NO. 20) were added to the wells 1 hour before stimulation. Cells were stimulated with 10 ng/ml LPS for a period of 5, 15, 30 or 60 min, then harvested and lysed. Proteins were resolved by SDS-PAGE, and transferred membranes immunoblotted for phospho-JNK (A), total JNK (B) or β-actin (C). The blots shown are representative of two experiments;

FIGS. 28A and B are immunoblots showing the effect of A464 on LPS-induced appearance of phospho-p38 MAPK in murine RAW264.7. Cells were set up as for FIG. 24 above and 5 µM A467 (SEQ ID NO. 23) or A464 (SEQ ID NO. 20) were added to the wells 1 hour before stimulation. Cells were stimulated with 10 ng/ml LPS for a period of 5, 30 or 60 min, then harvested and lysed. Proteins were resolved by SDS-PAGE, and transferred membranes immunoblotted for phospho-p38 (A) or total p38 (B). The blots shown are representative of two experiments;

FIG. 29 shows an immunoblot of a His-pulldown of overexpressed TLR4 adaptor proteins Mal and TRAM with His-tagged A464 peptide by affinity chromatography. HEK293_T cells were seeded in 6 well plate ($1.5 \times 10^5$ cells/ml) 24 hours before transfection with 1 µg/well Flag-Mal and 2 µg/well Flag-TRAM encoding plasmids. The total amount of plasmid DNA transfected into the cells was made up to 2 µg by adding pcDNA. 24 hours post-transfection cells were lysed in 1% NP-40 lysis buffer containing 20 mM imidazole. The experimental lysates were incubated with 25 µM His-A464 peptide ((H-H-H-H-H-H-KYSFKLILAEY) (SEQ ID NO. 66) and 40 µL of Ni-agarose beads for 2 hr at 4° C. Control samples were incubated with either beads only or beads and 25 µM His-A467 peptide (H-H-H-H-H-H-RNTISGNIYSA) (SEQ ID NO. 67). After incubation beads were washed 5 times in lysis buffer with imidazole. Proteins were resolved by SDS-PAGE, and transferred membranes immunoblotted for Flag. Data is representative of four experiments; and FIG. 30 is a graph showing that A464 inhibits LPS-induced IL-12/23 p40 in vivo. Groups of 5 female BALB/c mice were injected i.v. with a single bolus of one of the following: PBS, 1 µg LPS, 1 µg LPS with 3 mg/kg D-9RN-A464 (SEQ ID NO. 38), 1 µg LPS with 3 mg/kg L-9RN-A464 (SEQ ID NO. 38), or 1 µg LPS with 3 mg/kg L-9RN-A467 (SEQ ID NO. 39). Four hours later, blood was harvested and serum derived. The serum was assayed for IL-12p40 by ELISA. Concentrations are expressed as pg/ml. * $p<0.05$, *** $p<0.001$ samples versus LPS. # $p<0.01$ samples versus PBS. Serum levels of IL-12p40 in mice receiving D-9RN-A464 or L-9RN-A464 with LPS were not significantly different from mice receiving only PBS.

DETAILED DESCRIPTION OF THE INVENTION

Vaccinia virus proteins A52R and A46R have a distinct profile of inhibition against the TLR system, it may be possible to generate a repertoire of peptides with differential anti-inflammatory effects on the TLR system, whereby some peptides would specifically inhibit one distinct TLR signalling axis, while other peptides would block a number of pathways. This is particularly important to preserve anti-pathogen immunity while inhibiting an over active inflammatory response that causes pathogenesis. Although exogenous proteins with intracellular targets are unlikely to be attractive therapeutics, peptides based on critical amino acid sequences from inhibitory proteins, and peptide derivatives such as peptidomimetics have more potential. In fact others have shown that a peptide containing 11 amino acids of the A52R sequence fused to a cell-penetrating peptide (called P13, SEQ ID NO. 61) can reduce in vivo bacterial-induced inflammation, and LPS-induced inflammatory mediators in mice (McCoy et al, 2005; Tsung et al, 2007).

Figure 14:
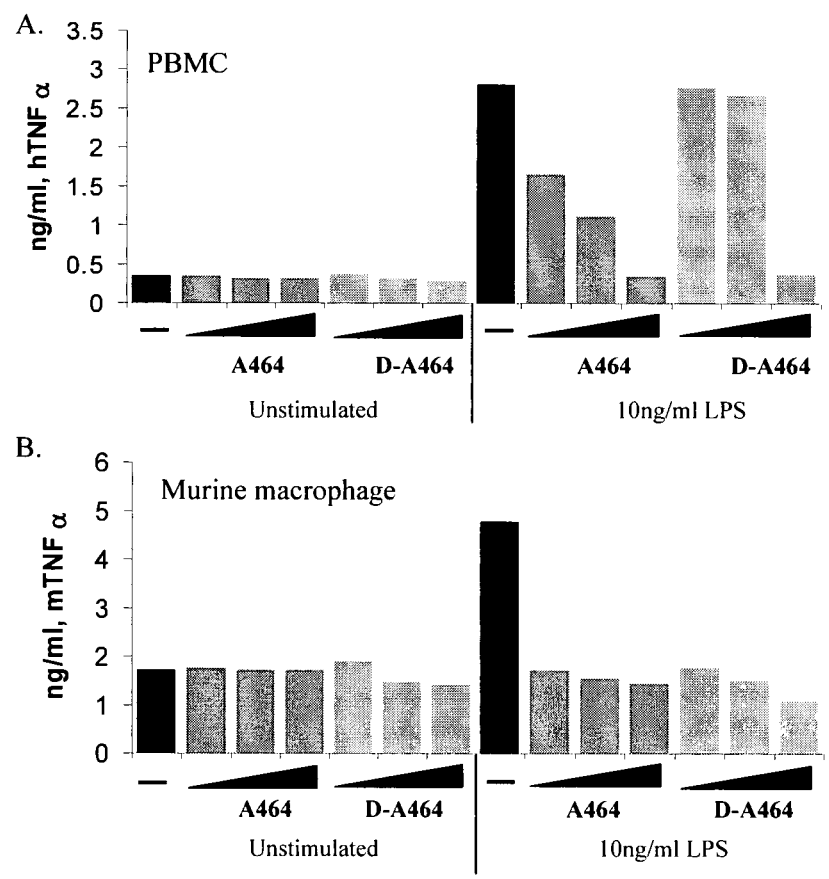

We describe an 11 amino acid peptide derived from the A46 protein sequence that inhibits TLR4 responses when fused to a cell-penetrating peptide. This peptide has several potential advantages over P13 (SEQ ID NO. 61): firstly, it is specific for one TLR, namely TLR4. This is surprising given that full-length A46 protein can inhibit multiple TLRs. Secondly it is active in human cells, which is not the case for P13 (SEQ ID NO. 61) (see FIG. 4). Thirdly, it inhibits TLR4 responses in vitro at a lower concentration than that reported for P13 (SEQ ID NO. 61, McCoy et al, 2005): FIG. 14 shows significant inhibition of TLR4 by A464 (SEQ ID No. 20) at 1 µM, in both murine and human cells. Furthermore, shorter forms of the peptide, namely SFKLIL (SEQ ID NO. 55) and FKLIL (SEQ ID NO. 62) are also shown to inhibit TLR4 when fused to a delivery peptide, making the development of a peptidomimetic more likely than would be the case with P13 (SEQ ID NO. 61).

Peptides derived from mammalian TIR protein BB loops have been shown to inhibit TLR signalling in vitro (Toshchakov et al, 2005; Loiarro et al, 2005; Toshchakov and Vogel, 2007; Toshchakov et al, 2007), which might suggest that a peptide from the A46 BB loop would also be inhibitory. However, the peptide discovered here, A464 (SEQ ID NO. 4 and 20), is from a region of A46 upstream of the BB loop. In fact, peptides derived from the A46 BB loop fused to cell-penetrating peptides, such as A467 (SEQ ID NO. 23), were found not to be inhibitory. Interestingly, A464 (SEQ ID NO. 20) has activity against TLR4 at a much lower concentration than peptides from mammalian BB loops (Toshchakov et al, 2007), and acts in a more specific manner since the only TLR it targets is TLR4.

The invention will be more clearly understood from the following examples.

EXAMPLES

Materials and Methods:
Plasmids

The empty vector pcDNA3.1 and the pFR-luciferase reporter construct containing five yeast Gal4 binding sites were purchased from Stratagene. NFκB-luciferase reporter construct containing 5×κB elements inserted into a pGL3 basic vector was obtained from R. Hofmeister, University of Rosenburg (93042 Rosenburg, Germany). The TK-Renilla luciferase reporter plasmid containing the Herpes Simplex Virus (HSV) thymidine kinase promoter and the *Renilla reniformis* luciferase gene in a pRL vector was from Promega. The plasmid encoding the fusion protein CD4-TLR4 was a gift from R. Medzhitov (Yale University, New Haven, Conn., USA). The plasmid encoding TLR3 was a gift from D. Golenbock (University of Massachusetts Medical School, Worchester, Mass., USA). The plasmids encoding Flag-Mal and Flag-TRAM were gifts from K. Fitzgerald (University of Massachusetts Medical School, Worchester, Mass., USA).

Cell Culture

The human embryonic kidney cell line 293 (HEK293) and HEK293 cells stably transfected with the Interleukin-1 Receptor (HEK293_R1) were a gift from Tularik Inc (San Francisco, Calif. 94080, USA). HEK293 cells stably transfected with Toll-Like Receptor (TLR) 2, 3, 4 and 8 (HEK293_TLR2, HEK293_TLR3, HEK293_TLR4 and HEK293_TLR8) were a gift from K. Fitzgerald (University of Massachusetts Medical School, Worcester, Mass., USA). Immortalised murine macrophages derived from bone marrow were a gift from D. Golenbock (University of Massachusetts Medical School, Worcester, Mass., USA). The mouse leukaemia monocyte-macrophage cell line RAW264.7, the human acute monocytic leukemia cell line THP-1 and the human leukemic monocyte lymphoma cell line U937 were obtained from the European Collection of Animal Cell Cultures (ECACC, Salisbury, UK). Adherent cells were grown in Dulbecco's Modified Eagle's Medium (DMEM) and suspension cells were grown in RPMI medium supplemented with 10% (v/v) heat inactivated foetal calf serum (FCS), 2 mM L-glutamine and 100 µg/ml gentamycin (referred to as complete medium). Cells were subcultured every two to three days when 60-80% confluent. Human peripheral blood mononuclear cells (PBMC) were isolated from the buffy coat of heparinized whole blood by density centrifugation on low-endotoxin ficoll-hypaque. Isolated PBMCs were washed three times in sterile phosphate-buffered saline (PBS: 137 mM NaCl, 2.7 mM KCl, 10 mM $Na_2HPO_4$, 2 mM $NaH_2PO_4$), counted and seeded at a density of $1 \times 10^6$ cells/ml in complete RPMI medium.

Antibodies

Antibodies used were mouse anti-β-actin antibody (Sigma), anti-Flag monoclonal antibody (Sigma), rabbit polyclonal anti-phosphospecific p38 antibody (Cell Signalling), anti-p38 antibody (Cell Signalling), rabbit polyclonal anti-phosphospecific JNK antibody (Biosource), anti-JNK antibody (Biosource), and mouse monoclonal anti-IκBα antibody (a gift from Ron Hay, University of Dundee, Scotland).

Receptor Agonists

Ultra-pure lipopolysaccharide (LPS) from *Eschericia coli* (>99.9% pure in respect to protein, DNA and TLR2 agonists contaminants) was from Alexis Corporation, the synthetic double-stranded RNA poly(I:C) was from Amersham Biosciences, IL-1α was from the National Cancer Institute (Frederick, Wash., USA) and TNFα was a gift from Zeneca Pharmaceutics (Macclesfield, UK). CpG DNA and PMA were a gift from K. Mills (Trinity College Dublin, Dublin, Ireland).

Reconstitution of Peptides

Peptides were chemically synthesised commercially by Genscript (www.genscript.com) and were at least 95% pure. Peptides were reconstituted with molecular biology grade sterile water to 10 mM and stored at −80° C. Working stocks of 1 mM and 200 µM were stored at 4° C. for a maximum of 2 weeks or else kept at −20° C.

Enzyme-Linked ImmunoSorbent Assay (ELISA)

Cytokine and chemokine production from cells or mouse serum was measured by ELISA using Duoset kits from R&D systems, according to the manufacturer's instructions.

MTT Assay

Cell viability was measured by assessing mitochondrial function using an MTT (3-(4,5-Dimethylthiazol-2-yl)-2,5-diphenyltetrazolium bromide) assay. Cells were seeded into 96 well plates and treated with peptides and agonists as described above in relation to the Figs. Wells containing medium only served as a blank control. To terminate treatment of cells, medium was removed and the cells were washed once with PBS. 200 µl per well of 1 mg/ml MTT in PBS was added directly to the cells and the plates were incubated at 37° C. for 14-16 hrs in the dark. MTT was then removed and 200 µl per well of dimethyl sulphoxide (DMSO) was added and cells incubated for 20 min at 37° C. in the dark, prior to absorbance being read at 595 nm on a spectrophotometer.

Reporter Gene Assays

HEK293 cells were transfected using GeneJuice® a proprietary non-toxic transfection reagent. 200 µl/well cells at a density of $1 \times 10^5$ cells/ml were seeded the day before transfection. 0.8 µl of GeneJuice was mixed with 9.2 µl of serum-free DMEM (SFM) per transfection and incubated for 5 min at room temperature before adding the appropriate amount of the plasmid DNA. The GeneJuice/SFM/DNA mixture was then incubated at room temperature for 15 min before adding to the cells. 10 µl per well of the GeneJuice/SMF/DNA mixture was added to the cells in triplicate and the cells were allowed to recover for 18-20 hours before stimulation. For the NFκB and ISRE reporter gene assays, 60 ng per well of either NFκB-luciferase or ISRE-luciferase reporter genes were used, together with 20 ng of the constitutively active internal control Renilla-luciferase gene reporter. To measure IRF3 activation, the Stratagene PathDetect System™ was used which employs a plasmid encoding a fusion protein of IRF3 and the Gal4 DNA-binding domain (DBD), together with the pFR-luciferase reporter plasmid which contains five yeast Gal4 binding sites that control expression of the firefly luciferase gene. The DBD of the fusion trans-activator protein binds to the reporter plasmid at the Gal4 binding sites. Phosphorylation of the IRF3 transcription activation domain of the fusion trans-activator protein activates transcription of the luciferase gene from the reporter plasmid. Therefore, activity of luciferase reflects the activation of IRF3. As before, Renilla-luciferase gene reporter plasmid was used as an internal control. In all cases the total amount of DNA per well was kept constant at 230 ng by the addition of pcDNA3.1. Cells were harvested 6 hours post-stimulation and lysed for 20 min using 50 µl of passive lysis buffer (Promega, Madison, Wis., USA) with vigorous shaking. 20 µl of the lysates were placed in two different plates to analyse for Firefly and Renilla luciferase activity. The substrate for firefly-luciferase was 40 µl of luciferase assay mix (20 mM tricine, 1.07 mM $(MgCO_3)_4$ $Mg(OH)_2$ $5H2O$, 2.67 mM $MgSO_4$, 0.1M EDTA, 33.3 mM DTT, 270 mM coenzyme A, 470 mM luciferin and 530 mM ATP), and the substrate for *Renilla luciferase* was 40 µl of coelentrazine (2 µg/ml in PBS). Luciferase activity was analysed using a luminometer.

Western Blot Analysis

RAW264.7 cells were seeded at a density of $1 \times 10^5$ cells/ml in 6 well plates. After treatment with peptides and agonists, as described above in relation to the Figs, the medium was removed and the cells were washed once with PBS before scraping them in 100 µl lysis buffer (100 mM NaCl, 50 mM HEPES (pH 7.5), 1 mM EDTA, 0.5% NP-40, 10% Glycerol) and incubating them on ice for 40 min. Samples were spun at 15,000×g for 10min and supernatants collected and stored at −20° C. A Bradford assay was used to determine the protein concentration in the samples. 1 µl of the sample was added to 480 µl Quick Start® Bradford Dye Reagent (BioRad Laboratories Inc, Hercules, Calif. 94547, USA) together with 19 µl deionised distilled water. The protein concentration was determined by monitoring the change in the solution absorbance at 280 nm using a spectrophotometer compared to protein standards. Cell lysates with a known protein concentration were then diluted with water to obtain a concentration of 30-40 mg/ml protein in each sample. 20 µl of the diluted samples were mixed with 5× Sample Buffer (62.5 mM Tris pH 6.8, 2% (w/v) SDS, 10% (v/v) Glycerol, 0.1% (w/v) Bromophenol Blue, 50 mM DTT) and boiled for 5 min at 99° C. Cooled samples were resolved on a sodium dodecyl sulphate (SDS) polyacrylamide gel, the resolved proteins were transferred to ImmobilonTM polyvinylidene difluoride (PVDF) membrane, and membranes were blocked for 1 hour at room temperature or over night at 4° C. With 5% (w/v) Marvel™ (non-fat dried milk) in 1% (v/v) PBS-Tween for IκBα, INK, β-actin and p38 and 1% (v/v) TBS-Tween for phospho-JNK and phospho-p38. The membrane then was incubated in the relevant primary antibody diluted 1:1000 in either 5% (w/v) Marvel™ in 1% (v/v) PBS-Tween for IκB, JNK, β-actin and p38 and in 3% (w/v) BSA in 1%(v/v) TBS-Tween for phospho-JNK and phospho-p38, for 2 hours at room temperature or overnight at 4° C. Thereafter, the membranes were washed, incubated in appropriate secondary antibody and then developed using standard enhanced chemiluminescence (ECL) reagents.

His Peptide Pulldown Assay

HEK293_T cells were seeded in 6 well plates (1.5×10$^5$ cells/ml) 24 hours before transfection. 8 μl of GeneJuice was mixed with 32 μl of serum-free DMEM (SFM) per transfection and incubated for 5 min at room temperature before adding 1 μg per transfection of Flag-Mal or 2 μg of Flag-TRAM encoding plasmid DNA. GeneJuice/SFM/DNA mixture was then incubated for 15 min at room temperature before adding to the cells. The total amount of plasmid DNA transfected into the cells was made up to 2 μg by adding pcDNA. 40 μl per well of the final mixture was added per well. 24 hours post-transfection supernatant was removed and cells were washed once with ice-cold 1× PBS before lysing in 600 μl of 1% NP-40 lysis buffer (100 mM NaCl, 50 mM HEPES (pH 7.5), 1 mM EDTA, 1% NP-40, 10% Glycerol) containing 20 mM imidazole on ice for 45 min. The lysates containing either Flag-Mal or Flag-TRAM were pooled together to ensure equal amount of the protein in each sample. 550 μl of lysates were incubated with 25 μl of either His-A464 (H-H-H-H-H-H-KYSFKLILAEY—SEQ ID No. 66) or His-A467 (H-H-H-H-H-H-RNTISGNIYSA—SEQ ID No. 67) peptide and 40 μl of Ni-agarose beads or beads only (control) for 2 hr at 4° C. rolling to avoid sedimentation of the beads. After incubation beads were washed 5 times in 1% NP-40 lysis buffer with 20 mM imidazole. After the final wash the buffer was completely removed and 35 μl of 1.5× Sample Buffer (62.5 mM Tris pH 6.8, 2% (w/v) SDS, 10% (v/v) Glycerol, 0.1% (w/v) Bromophenol Blue, 50 mM DTT) was added to each tube. Samples were boiled for 5 min at 99° C. and then were resolved on 10% sodium dodecyl sulphate (SDS) polyacrylamide gel. The resolved proteins were transferred to ImmobilonTM polyvinylidene difluoride (PVDF) membrane, and membranes were blocked for 1 hour at room temperature or over night at 4° C. in blocking buffer (5% (w/v) MarvelTM (non-fat dried milk) in 1% PBS-Tween). The membrane then was incubated in the anti-Flag primary antibody diluted 1:10000 in the blocking buffer, for 2 hours at room temperature or overnight at 4° C. Thereafter, the membranes were washed 6 times in 1% (v/v) PBS-Tween, and then incubated in anti-mouse secondary antibody diluted 1:10000 in blocking buffer. The signal was read using Odyssey Infrared Imaging System, LI-COR® Biosciences.

Example 1

Identification of TLR Inhibitory Peptides Derived from VACV A46

As the full-length A46 protein can inhibit TLR signalling and TLR-dependent gene induction (Stack et al, 2005), peptides derived from the A46 protein were assayed for TLR inhibitory effects. Secondary prediction programs suggest that A46 folds like a TIR domain, consistent with its ability to interact with mammalian TIR-containing proteins. A46-derived peptides were designed based on two regions of the A46 sequence that represent conserved TIR motifs. Firstly, the BB loop of the TIR domain is know to be important for signalling, and may mediate protein-protein interactions. Further, peptides derived from mammalian TIR protein BB loops have been shown to inhibit TLR signalling (Toshchakov et al, 2005; Loiarro et al, 2005; Toshchakov and Vogel, 2007; Toshchakov et al, 2007). Secondly, another region thought to be important for TIR-TIR interactions is the CD/DD loop. Truncated versions of A46 which retained the predicted CD/DD loop region are still inhibitory against TLRs. Therefore this region was also considered of interest. The predicted position of these loops in A46 (from Western Reserve strain of VACV, Protein ID: P26672) is shown below (underlined):

```
                                 (SEQ ID NO. 16)
MAFDISVNASKTINALVYFSTQQNKLVIRNEVNDTHYTVEFDRDKVVD 1    2    3    4    5
TFISYNRHNDTIEIRGVLPEETNIGCAVNTPVSMTYLYNKYSFKLILA 6   7    8                                9
EYIRHRNTISGNIYSALMTLDDLAIKQYGDIDLLFNEKLKVDSDSGLF
                              BB 10   11     12   13    14    15
DFVNFVKDMICCDSRIVVALSSLVSKHWELTNKKYRCMALAEHISDSI
      CD                        DD

PISELSRLRYNLCKYLRGHTESIEDKFDYFEDDDSSTCSAVTDRETDV
```

The numbers 1-15 refer to the position of the first amino acid in 15 peptides synthesised, to cover the BB, CD and DD loop regions of A46. Each peptide contained 11 amino acids from A46, and they overlap by approx 5 amino acids each. Peptides 1-8 surround the predicted BB loop of the protein, and peptides 9-15 cover the CD/DD loop regions. Peptides 1 to 15 have the following sequences:

| SEQ ID No. | Sequence | Peptide No. | Description |
|---|---|---|---|
| 1 | GCAVNTPVSMT | 1 | 461 |
| 2 | TPVSMTYLYNK | 2 | 462 |
| 3 | TYLYNKYSFKL | 3 | 463 |
| 4 | KYSFKLILAEY | 4 | 464 |
| 5 | LILAEYIRHRN | 5 | 465 |
| 6 | YIRHRNTISGN | 6 | 466 |
| 7 | RNTISGNIYSA | 7 | 467 |
| 8 | GNIYSALMTLD | 8 | 468 |
| 9 | DSGLFDFVNFV | 9 | 469 |
| 10 | DFVNFVKDMIC | 10 | 4610 |
| 11 | VKDMICCDSRI | 11 | 4611 |
| 12 | DSRIVVALSSL | 12 | 4612 |
| 13 | VALSSLVSKHW | 13 | 4613 |

-continued

| SEQ ID No. | Sequence | Peptide No. | Description |
|---|---|---|---|
| 14 | LVSKHWELTNK | 14 | 4614 |
| 15 | ELTNKKYRCMA | 15 | 4615 |

In order to deliver these peptides into cells, peptides 1 to 15 were linked to cell-penetrating peptides (also called peptide/protein transduction domains), which are short cationic peptides of normally 8-16 amino acids in length (Murriel & Dowdy, 2006). Cationic peptides are thought to allow delivery of their cargo into cells by a receptor-independent, fluid-phase macropinocytosis (Murriel & Dowdy, 2006). Once peptide-enclosed macropinosomes enter the cytoplasm, low pH stimulates endosomal release of the peptide-conjugated cargo (Murriel & Dowdy, 2006). Common cell-penetrating peptides employed include the amino acids 47-57 of HIV TAT (YGRKKRRQRRR) (SEQ ID No. 34), amino acids 43-58 of the antennapedia homeotic transcription factor (Ant, RQIKIWFQNRRMKWKK) (SEQ ID No. 35) and synthetic peptide carriers such as polyarginine (for example containing nine R residues, here termed 9R) (SEQ ID No. 33) (Murriel & Dowdy, 2006). As the rate of cellular uptake of the 9R peptide (SEQ ID No. 33) has been shown to be significantly faster than TAT (SEQ ID No. 34) or Ant (SEQ ID No. 35) for cells in vitro (Wender et al, 2000), the 9R peptide (SEQ ID No. 33) was selected to be fused to the A46-derived peptides (SEQ ID No. 1 to 15) in order to test their ability to inhibit TLR signaling in vitro. Wender et al (2000) showed that a polyarginine peptide containing only 6, 7 or 8 Rs is also taken up by cells, although less effectively than 9R (SEQ ID No. 33).

9R (SEQ ID NO. 33) was fused to the C-terminus of the A46-derived peptides (SEQ ID No. 1 to 15). The sequences of the peptides therefore were:

```
A461:
GCAVNTPVSMTRRRRRRRRR      (SEQ ID No. 17)

A462:
TPVSMTYLYNKRRRRRRRRR      (SEQ ID No. 18)

A463:
TYLYNKYSFKLRRRRRRRRR      (SEQ ID No. 19)

A464:
KYSFKLILAEYRRRRRRRRR      (SEQ ID No. 20)

A465:
LILAEYIRHRNRRRRRRRRR      (SEQ ID No. 21)

A466:
YIRHRNTISGNRRRRRRRRR      (SEQ ID No. 22)

A467:
RNTISGNIYSARRRRRRRRR      (SEQ ID No. 23)

A468:
GNIYSALMTLDRRRRRRRRR      (SEQ ID No. 24)

A469:
DSGLFDFVNFVRRRRRRRRR      (SEQ ID No. 25)

A4610:
DFVNFVKDMICRRRRRRRRR      (SEQ ID No. 26)

A4611:
VKDMICCDSRIRRRRRRRRR      (SEQ ID No. 27)

A4612:
DSRIVVALSSLRRRRRRRRR      (SEQ ID No. 28)

A4613:
VALSSLVSKHWRRRRRRRRR      (SEQ ID No. 29)

A4614:
LVSKHWELTNKRRRRRRRRR      (SEQ ID No. 30)

A4615:
ELTNKKYRCMARRRRRRRRR      (SEQ ID No. 31)
```

(The peptides were named as A46X where X represents the peptide number from the order in which it appears in SEQ ID No. 16)

Figure 1:
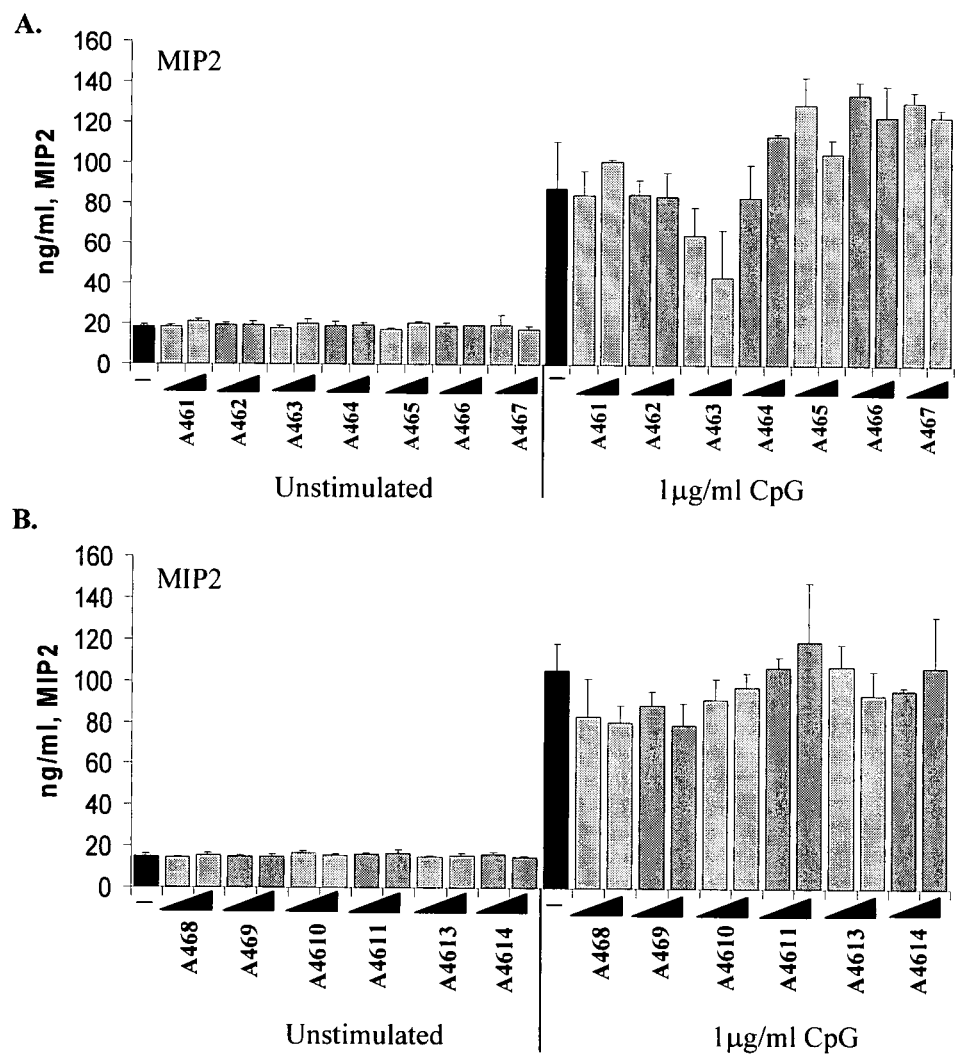
FIGS. 1A and B are bar charts showing the effect of peptides derived from A46 on CpG-induced MIP-2 production murine RAW264.7 cells. Cells were seeded in 96 well plates ($1.5 \times 10^5$ cells/nil) at least 24 hours before treatment. A46 peptides were added to the cells at a concentration of 5 or 20 µM 1 hour before stimulating with 1 µg/ml CpG. Supernatants were collected 24 hours after stimulation and assayed for MIP2 by ELISA. No peptides were added into the control wells (black bars). (A) peptides A461-A467 (SEQ ID NO. 17 to 23). (B) peptides A468-A4614 (SEQ ID NO. 24 to 30) (excluding A4612 SEQ ID NO. 28). Data is representative of at least two experiments each performed in triplicate and is expressed as mean±s.d.
Figure 2:
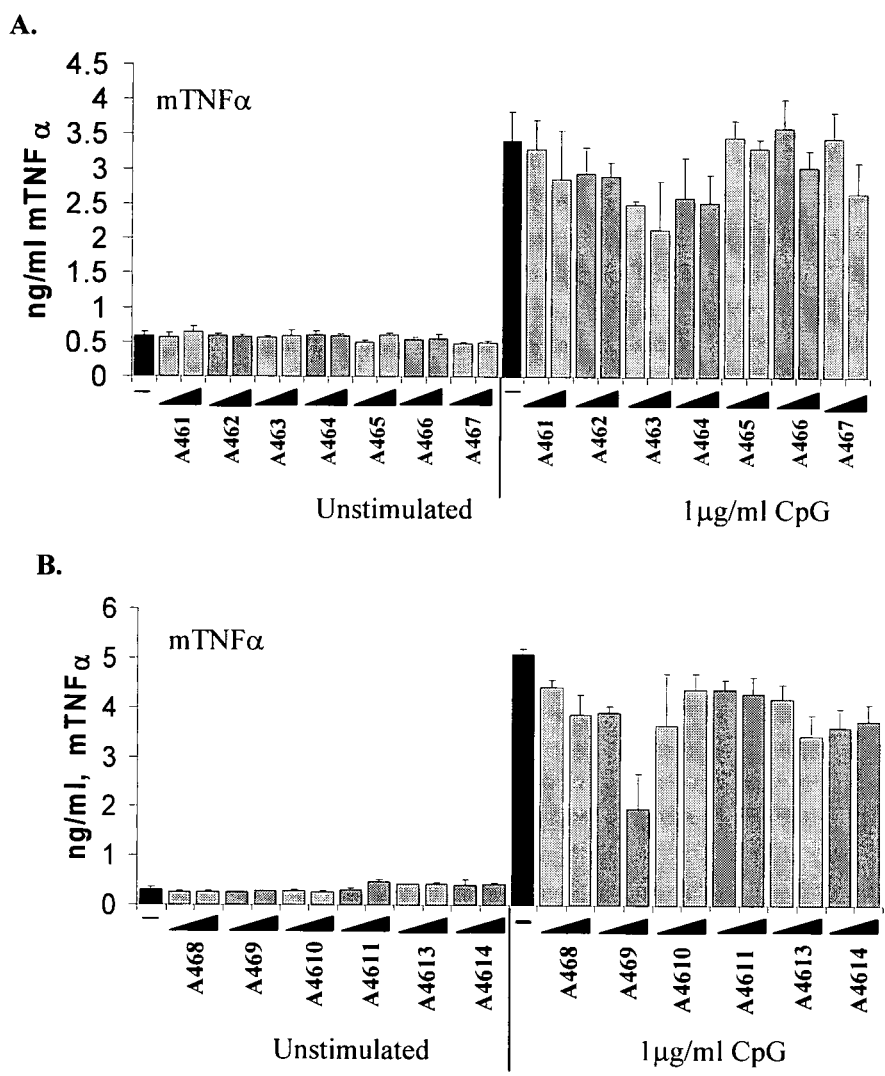
FIGS. 2A and B are bar charts showing the effect of peptides derived from A46 on CpG-induced TNFα in murine RAW264.7 cells. A46 peptides were added to the cells at a concentration of 5 or 20 µM 1 hour before stimulating with 1 pg/ml CpG. Supernatants were collected 24 hours after stimulation and assayed for TNFα by ELISA. No peptides were added into the control wells (black bars). (A) peptides A461-A467 (SEQ ID NO. 17 to 23). (B) peptides A468-A4614 (SEQ ID NO. 24 to 30) (excluding A4612 SEQ ID NO. 28). Data is representative of at least two experiments each performed in triplicate and is expressed as mean±s.d.

These peptides were initially screened for effects on TLR-induced gene induction in vitro using the murine macrophage cell line RAW264.7. Unmethylated CpG dinucleotides of bacterial DNA sequences are detected by TLR9, which leads to production of pro-inflammatory cytokines and chemokines, including TNFα via a MyD88-dependent pathway (Latz et al, 2004). RAW264.7 cells showed very potent cytokine production when stimulated with 1 µg/ml CpG (FIG. 1). The effect of the peptides on two TLR9-induced cytokines, namely TNFα and MIP-2, was measured by ELISA. TNFα is NFκB-dependent, and MIP-2 as well as NFκB also requires IRFs for transcriptional activation (De Filippo et al, 2008). The cells were plated out at $1 \times 10^5$ cells/ml 24 hours before treatment. Peptides were added at concentrations of 5 and 20 µM 1 hour before stimulation with CpG and supernatants were collected 24 hours post-CpG stimulation for MIP-2 and mTNFα measurement. This showed that only A463 (SEQ ID No. 19) inhibited CpG-induced MIP-2 secretion (FIG. 1), while only A469 (SEQ ID No. 25) inhibited TNFα production (FIG. 2).

Figure 3:
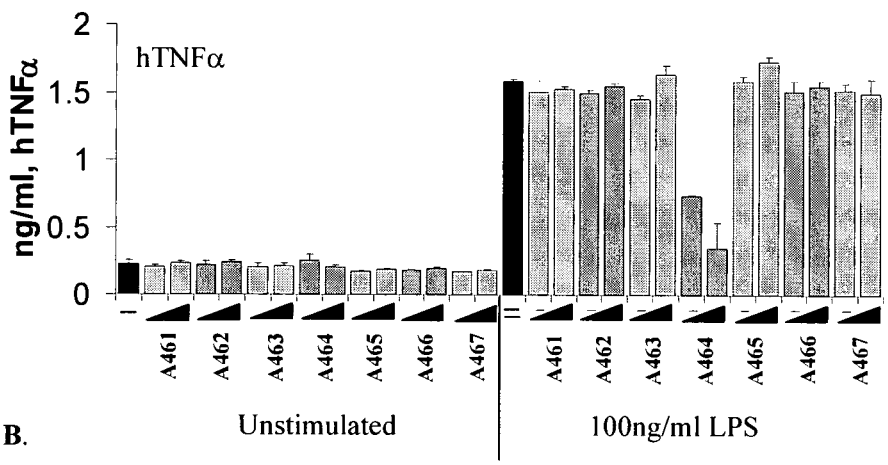
FIGS. 3A and B are bar charts showing the effect of peptides derived from A46 on LPS-induced TNFα in human U937 cells. Cells were differentiated with 200 nM PMA and seeded in 96 well plates ($2 \times 10^5$ cells/ml) 24 hours before treatment. A46 peptides were added to the cells at a concentration of 5 or 20 µM 1 hour before stimulating with 100 ng/ml LPS. Supernatants were collected 24 hours after stimulation and assayed for TNFα by ELISA. No peptides were added into the control wells (black bars). (A) peptides A461-A467 (SEQ ID NO. 17 to 23). (B) peptides A468-A4614 (SEQ ID NO. 24 to 30) (excluding A4612 SEQ ID NO. 28). Data is representative of at least two experiments each performed in triplicate and is expressed as mean±s.d.
Figure 3:
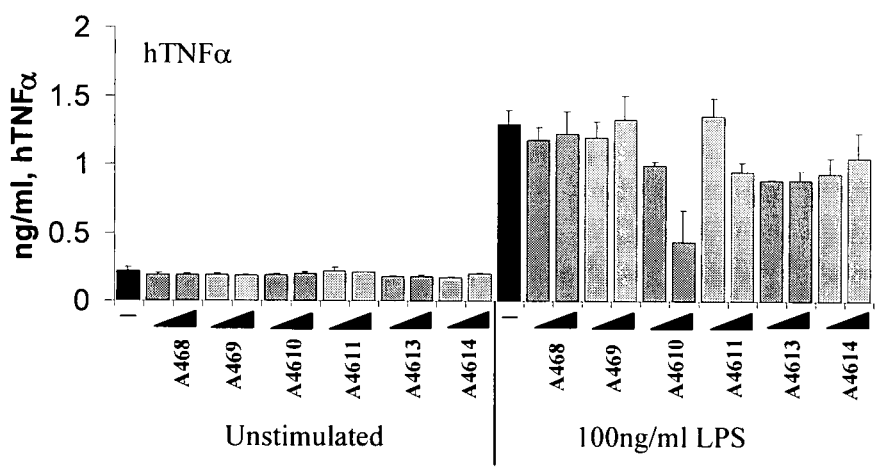

LPS is a component of a cell wall of Gram-negative bacteria which is recognised by a homodimer of TLR4 and signals to NFκB via both a MyD88- and TRIF-dependent pathway (O'Neill and Bowie, 2007). In order to examine the effect of the peptides on TLR4-dependent gene induction in human cells, the human monocytic lymphoma cell line U937 was used. U937 cells were differentiated into macrophages by treatment with 200 nM PMA for 24 hours before any further manipulations. The A46 peptides (SEQ ID No. 17 to 31) were added to the cells as described for RAW264.7 above and the cells were stimulated with 100 ng/ml LPS for 24 hours. In this case, A464 (SEQ ID No. 20) was found to potently inhibit TLR4-mediated TNFα production, while A4610 (SEQ ID No. 26) was also effective, but less so (FIG. 3).

A more detailed investigation of A463 (SEQ ID No. 19), A464 (SEQ ID No. 20), A469 (SEQ ID No. 21) and A4610 (SEQ ID No. 22) was undertaken, and this showed that generally A463 (SEQ ID No. 19), A469 (SEQ ID No. 21) and A4610 (SEQ ID No. 22), as well as inhibiting TLRs, also reduced cell viability (as assessed by the MTT assay, which measures activity of mitochondrial reductase, which can be related to the number of living cells (Domart-Coulon et al, 2000; Henneke et al, 2002). Thus, future work focused on A464 (SEQ ID No. 20), which was found to be less toxic, and to be more potent than the other peptides at lower doses.

Example 2

A464 is an Inhibitor of Murine and Human TLR4

Figure 4:
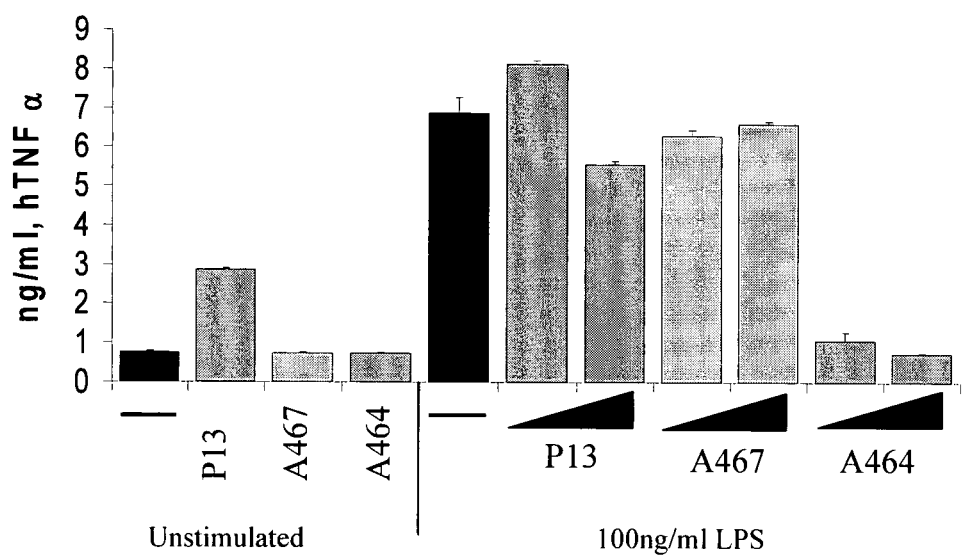
FIG. 4 is a bar chart showing the comparison of effect of P13, A467 and A464 peptides on LPS induced TNFα in human THP-1 cells. Cells were seeded in 96 well plates ($3 \times 10^5$ cells/ml) and differentiated with 200 nM PMA for at least 24 hours before treatment. P13 (SEQ ID No. 61), A467 (SEQ ID NO. 23) and A464 (SEQ ID NO. 20) peptides were added to the cells at a concentration of 20 or 40 µM 1 hour before stimulating with 100 ng/ml LPS. Supernatants were collected 6 hours after stimulation with the agonist and assayed for TNFα by ELISA. The peptides were added to the unstimulated wells at 40 µM. No peptides were added to the control wells (black bars). Data is representative of at least three experiments each performed in triplicate and is expressed as mean±s.d.

A464 (SEQ ID No. 20) showed a very potent inhibitory effect on LPS (TLR4)-induced TNFα production in U937 human cells, as shown in FIG. 4, and little or no effect on CpG (TLR9)-induced cytokine production (FIG. 1A and FIG. 2A).

Figure 5:
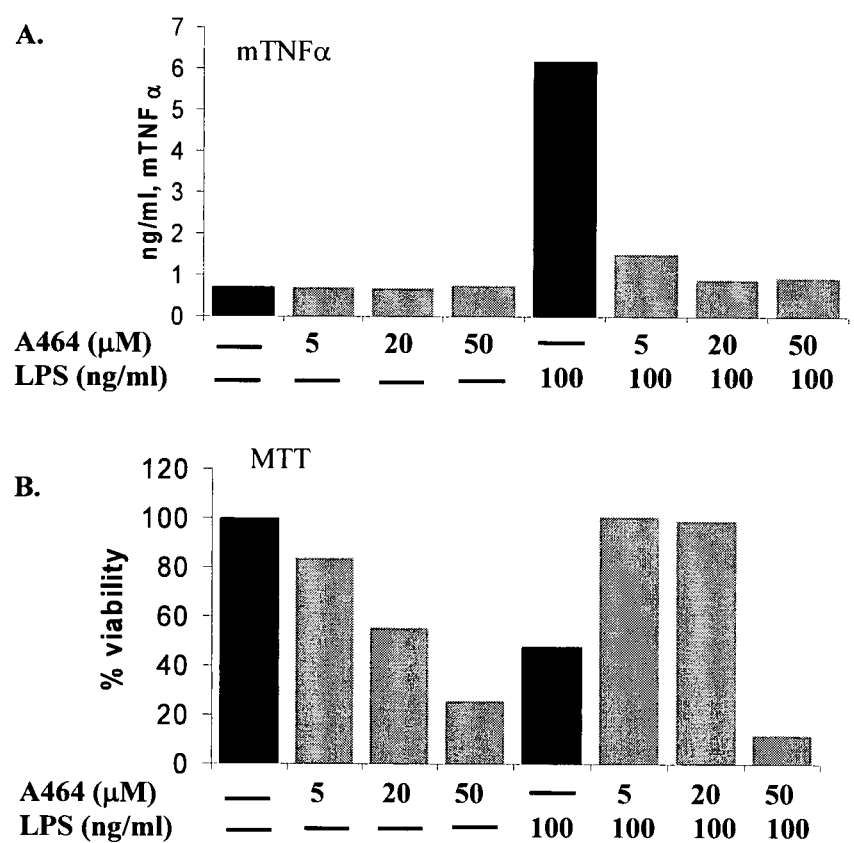
FIGS. 5A and B are bar charts showing the dose-dependent inhibitory effect of A464R on LPS-induced TNFα in murine RAW264.7 cells. A464 (SEQ ID NO. 20) was added to the cells at a concentration of 5, 20 or 50 µM 1 hour before stimulating with 100 ng/ml LPS. Supernatant was collected 24 hours after stimulation and assayed for TNFα by ELISA (A) and cells were assayed for viability by the MTT assay (B.). No peptides were added to the control wells (black bars). Data is representative of at least three experiments each performed in triplicate and is expressed as mean±s.d.

A52 is another vaccinia virus protein which can inhibit TLR signaling, and it has been shown that a peptide containing 11 amino acids of the A52 sequence together with a 9R delivery sequence (termed P13, SEQ ID NO. 61) can reduce in vivo bacterial-induced inflammation in a murine model (McCoy et al, 2005). Therefore the ability of A464 (SEQ ID No. 20) and P13 (SEQ ID NO. 61) to inhibit TLR4-induced cytokine production in human cells was compared. For this, the human acute monocytic leukemia cell line THP-1, which is widely used to study LPS responses, was employed. THP-1 cells were stimulated with 100 ng/ml LPS. In this experiment the supernatants were collected 6 hours after stimulation, because TNFα production by these cells was shown to be highest after only 4-6 hours post-stimulation (Takashiba et al, 1999). In the majority of the further described ELISA experiments assaying for TNFα, the supernatants were harvested 6 hours after stimulation, unless otherwise stated. Here and for following experiments, A467 (SEQ ID No. 23) was used as a control peptide, since we found it to be inert towards TLRs in every cell type and TLR pathway tested. As before 20 μM A464 (SEQ ID No. 20) inhibited TLR4-mediated TNFα production (FIG. 4). Surprisingly however, P13 (SEQ ID NO. 61), even at a high dose of 40 μM, was ineffective at inhibiting TLR4 (FIG. 4). In fact we consistently found that P13 (SEQ ID NO. 61) was unable to block TLR responses in human cells, suggesting that any in vivo effects of P13 (SEQ ID NO. 61) might be restricted to the murine system. In contrast, A464 (SEQ ID No. 20) was inhibitory against TLR4 in both human (FIG. 4) and murine cells. FIG. 5 shows that A464 (SEQ ID No. 20) potently inhibited LPS-induced murine TNFα production in RAW264.7 cells at just 5 μM (FIG. 5A). A simultaneous MTT assay showed no toxicity at the concentrations of 5 and 20 μM in the presence of LPS, and some cytotoxicity at 20 μM in the absence of LPS (FIG. 5B).

Figure 6:
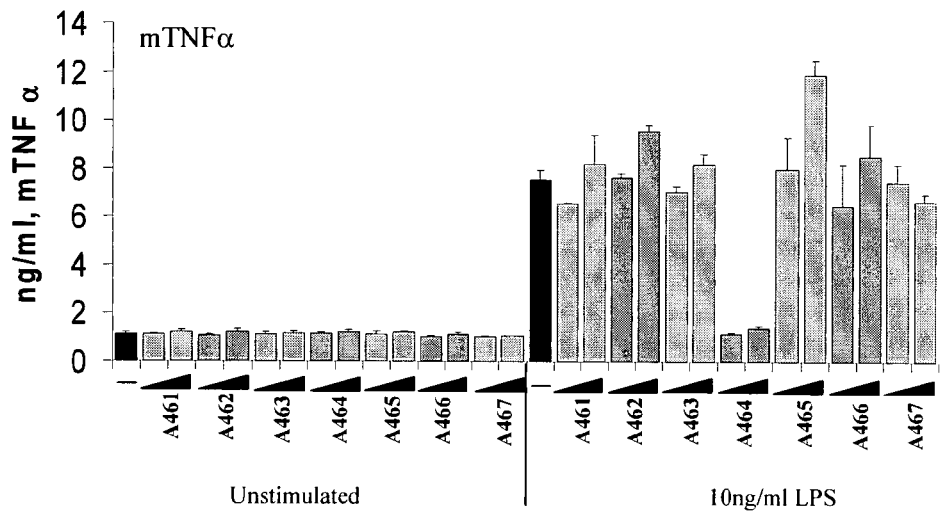
FIGS. 6A and B are bar charts showing the effect of peptides derived from A46 on LPS-induced TNFα in murine RAW264.7 cells. A46 peptides were added to the cells at a concentration of 1 or 5 µM 1 hour before stimulating with 10 ng/ml LPS. Supernatants were collected 6 hours after stimulation and assayed for TNFα by ELISA. No peptides were added into the control wells (black bars). (A) peptides A461-A467 (SEQ ID NO. 17 to 23). (B) peptides A468-A4614 (SEQ ID NO. 24 to 30) (excluding A4610 SEQ ID NO. 26 and A4612 SEQ ID NO. 28). Data is representative of at least two experiments each performed in triplicate and is expressed as mean±s.d.
Figure 6:
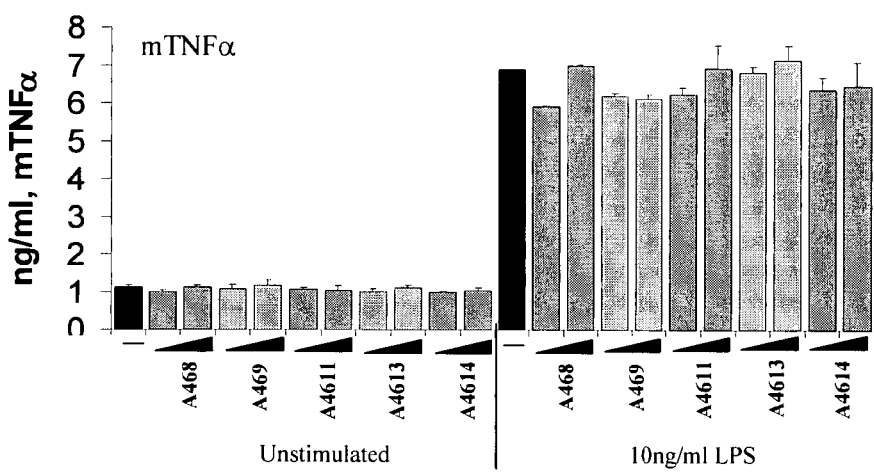
Figure 7:
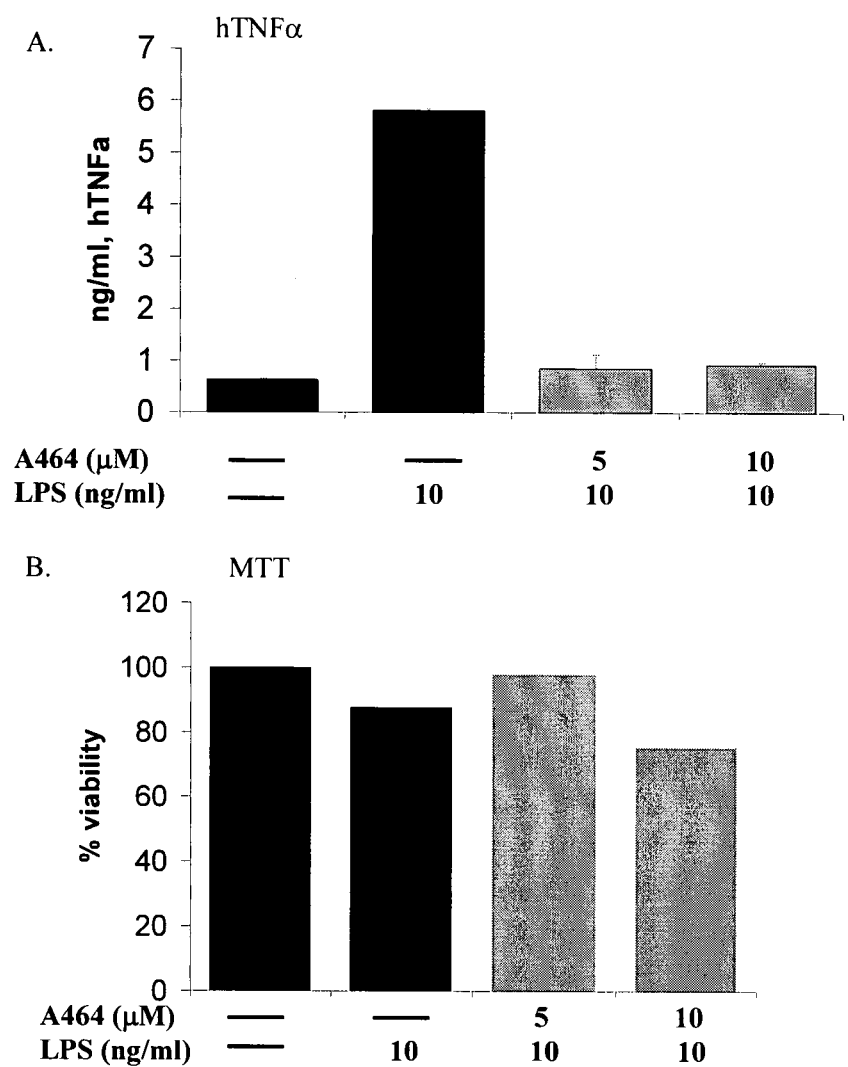
FIGS. 7A and B are bar charts showing the effect of A464 on TNFα production and cell viability of human THP-1 cells stimulated with LPS. Cells were seeded in 96 well plates ($3 \times 10^5$ cells/ml) and differentiated with 200 nM PMA for 24 hours before treatment. A464 (SEQ ID NO. 20) was added to the cells at a concentration of 5 or 10 µM 1 hour before stimulating with 10 ng/ml LPS. Supernatants were collected 6 hours after stimulation and assayed for TNFα by ELISA (A) and cells were assayed for viability by the MTT assay (B.). No peptides were added to the control wells (black bars). Data is representative of at least three experiments each performed in triplicate and is expressed as mean±s.d.
Figure 8:
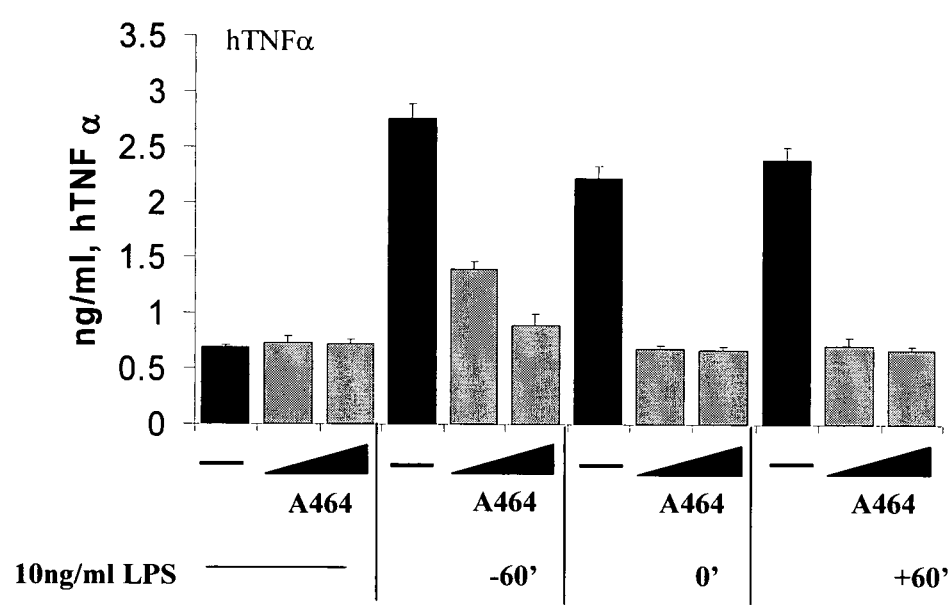
FIG. 8 is a bar chart showing an investigation of the inhibitory potential of A464 when added to cells after, during and before stimulation with LPS. THP-1 cells were seeded in 96 well plates ($3 \times 10^5$ cells/ml) and differentiated with 200 nM PMA for 24 hours before treatment. A464 (SEQ ID NO. 20) was added to the cells at a concentration of 5 or 10 µM. Cells were stimulated at different time points in relation to addition of the peptide: 1 hour before adding the peptide (−60'), at the same time as peptide (0'), or 1 hour after the peptide was added (+60'). Supernatants were collected 6 hours after stimulation and assayed for TNFα by ELISA. No peptides were added to the control wells (black bars). Data is representative of at least three experiments each performed in triplicate and is expressed as mean±s.d.

Next, lower doses of A464 (SEQ ID No. 20) were tested for efficacy against TLR4 in murine cells, compared to the other A46-derived peptides. As shown in FIG. 6, only A464 (SEQ ID No. 20), and not A461 (SEQ ID No. 17), A462 (SEQ ID No. 18), A463 (SEQ ID No. 19), A465 (SEQ ID No. 21), A466 (SEQ ID No. 22), A467 (SEQ ID No. 23), A468 (SEQ ID No. 24), A469 (SEQ ID No. 25), A4611 (SEQ ID No. 27), A4613 (SEQ ID No. 29) or A4614 (SEQ ID No. 30), inhibited LPS-induced mTNFα at 1 and 5 μM. Further, in human THP-1 cells complete inhibition of TLR4 was achieved at 5 and 10 μM peptide with no cytotoxicity (FIG. 7). Seeing such a strong inhibition of the TLR4-induced cytokine production by the peptide, it was interesting to assay the potency of the peptide to inhibit the signal when the cells were stimulated before the peptide was added, and this showed that 5 and 10 μM A464 (SEQ ID No. 20) almost completely inhibited LPS-induced hTNFα production even when added 1 hour after the stimulation with LPS (FIG. 8).

Figure 9:
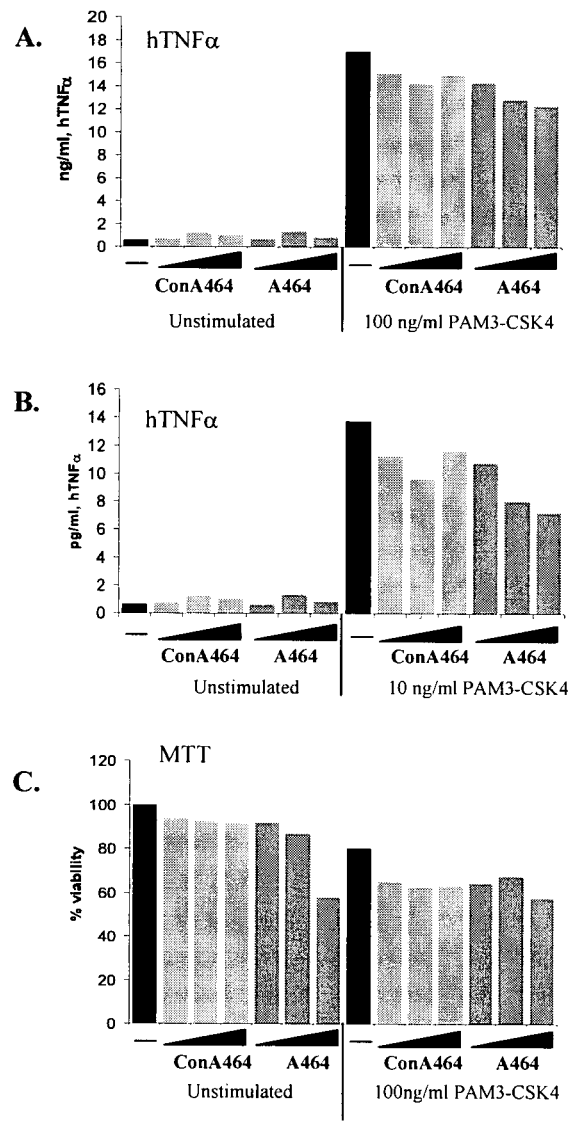
FIGS. 9A and B are bar charts showing the effect of A464 on Pam3CysK4-induced TNFα in human THP-1 cells. Cells were seeded in 96 well plates ($3 \times 10^5$ cells/ml) and differentiated with 200 nM PMA for 24 hours before treatment. A464 (SEQ ID NO. 20) was added to the cells at a concentration of 1, 5 or 10 μM 1 hour before stimulating with either 100 ng/ml (A) or 10 ng/ml Pam3CysK4 (B). Supernatants were collected 24 hours after stimulation and assayed for TNFα by ELISA. Cells from (B) were also assayed for viability by the MTT assay (C). No peptides were added to the control wells (black bars). Data is representative of at least three experiments each performed in triplicate and is expressed as mean±s.d.
Figure 10:
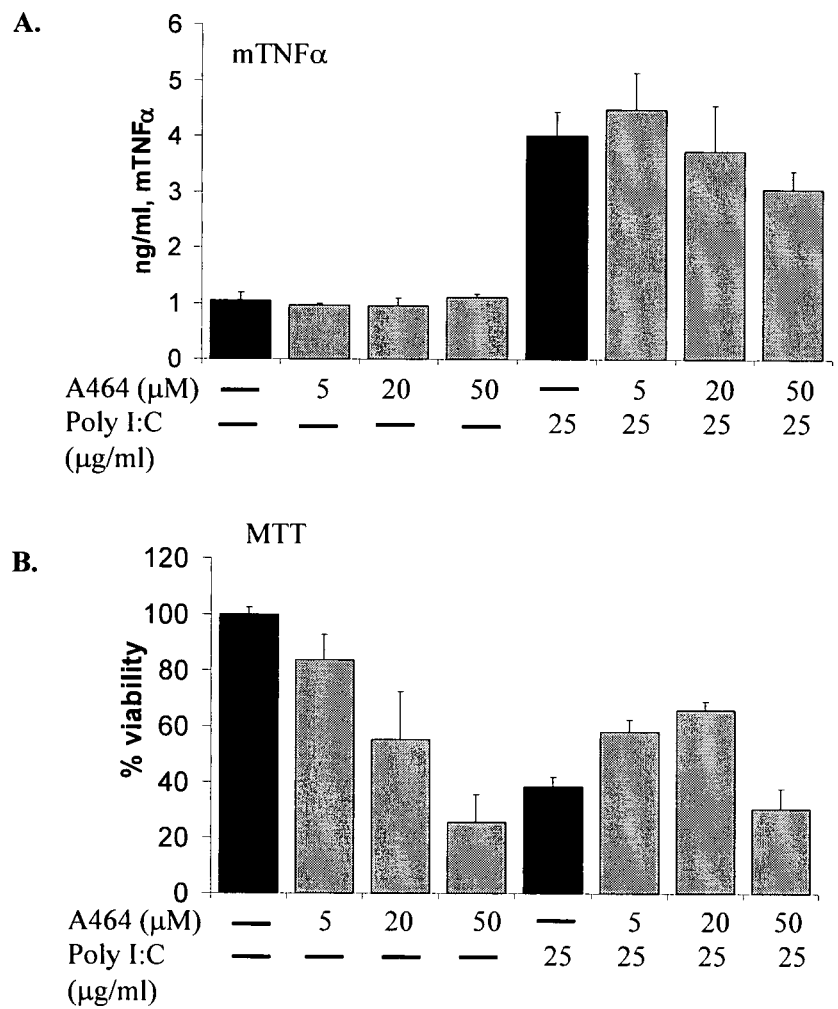
FIGS. 10A and B are bar charts showing the effect of A464 on poly(I:C)-induced TNFα in murine RAW264.7 cells. Cells were seeded in 96 well plates ($1.5 \times 10^5$ cells/nil) 24 hours before treatment. A464 (SEQ ID NO. 20) was added to the cells at a concentration of 5, 20 or 50 μM 1 hour before stimulating with 25 μg/ml Poly(I:C). Supernatants were collected 24 hours after stimulation and assayed for TNFα by ELISA (A) and cells were assayed for viability by the MTT assay (B). No peptides were added to the control wells (black bars). Data is representative of at least three experiments each performed in triplicate and is expressed as mean±s.d.

Thus far, A464 (SEQ ID No. 20) had been shown to inhibit both murine and human TLR4, but not murine TLR9. In order to determine whether A464 (SEQ ID No. 20) was specific for TLR4, other TLR pathways were next assayed for sensitivity to A464 (SEQ ID No. 20). A scrambled version of A464 (SEQ ID No. 20) peptide was designed to use as a further control peptide, and this had the sequence: KALSIFYEKYLR-RRRRRRRR (ConA464, SEQ ID No. 32). The A464R (SEQ ID No. 20) and ConA464 (SEQ ID No. 32) peptides were assayed for inhibition of TLR2 signalling in THP-1 cells. Pam3CysK4 (S-(2,3-bis(palmitoyloxy)-(2-RS)-propyl)-N-palmitoyl-(R)-Cys-(S)-Ser-(S)-Lys(4)) is a synthetic tripalmitoylated lipopeptide that is recognized by a TLR2/ TLR1 heterodimer and leads to activation of NFκB through a Mal- and MyD88-dependent pathway. A464 (SEQ ID No. 20) and ConA464 (SEQ ID No. 32) had only very minor inhibitory effects on hTNFα secretion by 100 ng/ml Pam3CysK4 (FIG. 9A), which were slightly heightened when 10 ng/ml Pam3CysK4 was used instead (FIG. 9B). However, these effects were likely not significant since there was a similar level of toxicity upon peptide treatment (FIG. 9C). Similar results were obtained in murine cells, in that TLR2 was unaffected by A464 (SEQ ID No. 20). Next, the effect of A464 (SEQ ID No. 20) on RAW264.7 cells was assayed. TLR3, like TLR4, uses TRIF to mediate both NFκB and IRF3 activation (O'Neill and Bowie, 2007). Here some inhibition of mTNFα production in response to stimulation with 25 mg/ml Poly(I:C) was seen but only at a concentration of 50 μM (FIG. 10A), where there was toxicity (FIG. 10B). TLR3-mediated NFκB activation and ISRE induction was also assayed, and found to be insensitive to inhibition by either ConA464 (SEQ ID No. 32) or A464 (SEQ ID No. 20) (FIG. 11). In fact A464 (SEQ ID No. 20) slightly enhanced activation of NFκB and induction of ISRE (FIG. 11). These luciferase reporter gene assays were performed in human HEK293_TLR3 cells, which stably express TLR3. The cells were transfected with either NFκB- or ISRE-luciferase and TK-Renilla-luciferase plasmid constructs 24 hours before treatment with the peptide. As before, peptide was added to the cells at various concentrations and the cells were stimulated with poly(I.C) for 6 hours.

A464 (SEQ ID No. 20) was also tested for an effect on NFκB activation via TLR8 in HEK293 cells. TLR8-dependent NFκB activation proceeds via MyD88 (O'Neill and Bowie, 2007). Cells were stimulated with 2.5 μg/ml CL075, a thiazoloquinolone derivative which is a potent synthetic TLR8 agonist (Gorden et al, 2005). It was found that neither A467 (SEQ ID No. 23) nor A464 (SEQ ID No. 20) had any inhibitory effect on TLR8-signalling, even at doses of 25 μM (FIG. 12). Although murine TLR8 is non-functional, the closely related murine TLR7 is functional and this was also found to be insensitive to A464 (SEQ ID No. 20) inhibition.

Next, the A464 (SEQ ID No. 20) peptide was tested in primary human cells. Peripheral blood mononuclear cells (PBMCs) were purified from uncoagulated whole blood using the Ficol Gradient method, and seeded in 96 well plates 24 hours before treatment. A464 (SEQ ID No. 20) and A467 (SEQ ID No. 23) were then added to the cells at concentrations of 1, 5 and 25 μM 1 hour before stimulation with 10 ng/ml LPS for 6 hours. As shown in FIG. 13A, 5 μM A464 (SEQ ID No. 20) peptide almost completely blocked hTNFα production in response to LPS, while A467 (SEQ ID No. 23) had no effect at any dose. The MTT assay showed that both peptides were not toxic for these cells at all concentrations used (FIG. 13B).

Thus, A464 (SEQ ID No. 20) is a potent inhibitor of human and murine TLR4, but has little or no inhibitory effect against human TLR2, TLR3 or TLR8, or murine TLR2, TLR3, TLR7 or TLR9. Further, it is capable of inhibiting LPS responses in primary human cells.

Example 3

Effect of Altered Stereochemistry and Delivery Peptide on the Inhibitory Potential of A464

For further development of the peptide as a potential therapeutic agent it was of use to investigate A464's (SEQ ID No. 4) behaviour if the orientation of the amino acids were changed from the natural L-(lavarotatory)-form to D-(dextrarotatory)-form, since the D-form increases peptide stability and is therefore often used in vivo. Thus, the D-form of A464 (SEQ ID No. 20) (D-A464) was chemically synthesised and tested for inhibitory effects on LPS-induced TNFα production in primary human PBMCs and immortalized murine macrophages. In PBMCs D-A464 still inhibited TNFα, although it was less potent than A464 (SEQ ID No. 20), since it only blocked TNFα secretion at 25 µM (FIG. 14A). However, in the murine cells D-A464 was as potent as A464 (SEQ ID No. 20), since both demonstrated complete inhibition at 1 (FIG. 14B).

We also compared the TAT delivery peptide (SEQ ID No. 34) to 9R (SEQ ID No. 33) since although here 9R (SEQ ID No. 33) proved to be very efficient in vitro, there are reports that TAT (SEQ ID No. 34) is more efficient in vivo (Schwarze et al, 1999). Bearing this in mind it was decided to test the TAT delivery sequence (SEQ ID No. 34) for delivering the 464 (SEQ ID No. 4) peptide into primary cells in vitro. Therefore D-A464 TAT (SEQ ID No. 36) and D-A467 TAT (SEQ ID No. 37) peptides with the TAT delivery sequence (SEQ ID No. 34) at the C-terminus rather than 9R (SEQ ID No. 33) were synthesised and tested in primary human and murine cells. In PBMCs D-A464-TAT (SEQ ID No. 36) failed to inhibit LPS-induced hTNFα production at 1-25 µM (FIG. 15A), while in murine cells it still inhibited, but only at 5-25 µM (FIG. 15B).

Next we tested whether attaching the 9R delivery sequence (SEQ ID No. 33) to the N-terminus of the peptide instead of C-terminus would affect the inhibitory potential, since this might further protect the inhibitory amino acids from degradation. Thus new 9RN-A464 (SEQ ID No. 38) and 9RN-A467 (SEQ ID No. 39) peptides with the 9R delivery sequence on N-termini were synthesised and tested in primary human and murine cells. It was found that 9RN-A464 (SEQ ID No. 38) peptide inhibited LPS-induced mTNFα more potently than A464 (SEQ ID No. 20) in murine cells, since complete inhibition was observed at 1 µM peptide (FIG. 16A). However this modification did not improve inhibitory potential of the peptide in the human PBMCs, since inhibition was only observed from 5-25 µM (FIG. 16B). Changing the peptide with the 9R at the N-terminus to the D-form did not improve but weakened its inhibitory potential. In the murine cells no inhibition at 1 µM was now observed (FIG. 17A), while in the human cells it inhibited TNFα only at concentration of 24 µM (FIG. 17B).

These results demonstrate that the amino acid residues derived from A46 which are represented in 464 (SEQ ID No. 4) can still inhibit TLR4 responses when the stereochemistry of the peptide, or the orientation and nature of delivery peptide, are altered. However, in murine cells, attachment of the 9R delivery peptide (SEQ ID No. 33) to the N-terminus rather than the C-terminus improves the potency of inhibition of TLR4.

Example 4

Identification of Amino Acids in A464 Critical for Inhibition of TLR4

Previously we showed that peptides derived from the regions of A46 surrounding the A464 sequence (SEQ ID No. 20), namely A463 (SEQ ID No. 19) and A465 (SEQ ID No. 21), did not inhibit TLR4 responses (FIG. 3). Since these peptides partially overlapped with A464 (SEQ ID No. 4), it was possible that a shorter sequence within A464 (SEQ ID No. 4) might be critical for TLR4 inhibition, and that a shorter inhibitory peptide could be designed. Thus four shorter peptides with amino acids removed from either end of the A46-derived amino acids in A464 (SEQ ID No. 4) were designed and synthesized: A464N-1: YSFKLILAEY-9R (SEQ ID No. 40)—a peptide with a deletion of the first amino acid from the N-terminus; A464N-2: SFKLILAEY-9R (SEQ ID No. 41)—a peptide with a deletion of the first two amino acids from the N-terminus; A464C-3: KYSFKLIL-9R (SEQ ID No. 42)—a peptide with a deletion of the last three amino acids from the C-terminus; and A464C-6: KYSFK-9R (SEQ ID No. 43)—a peptide with a deletion of the last six amino acids from the C-terminus.

Figure 18:
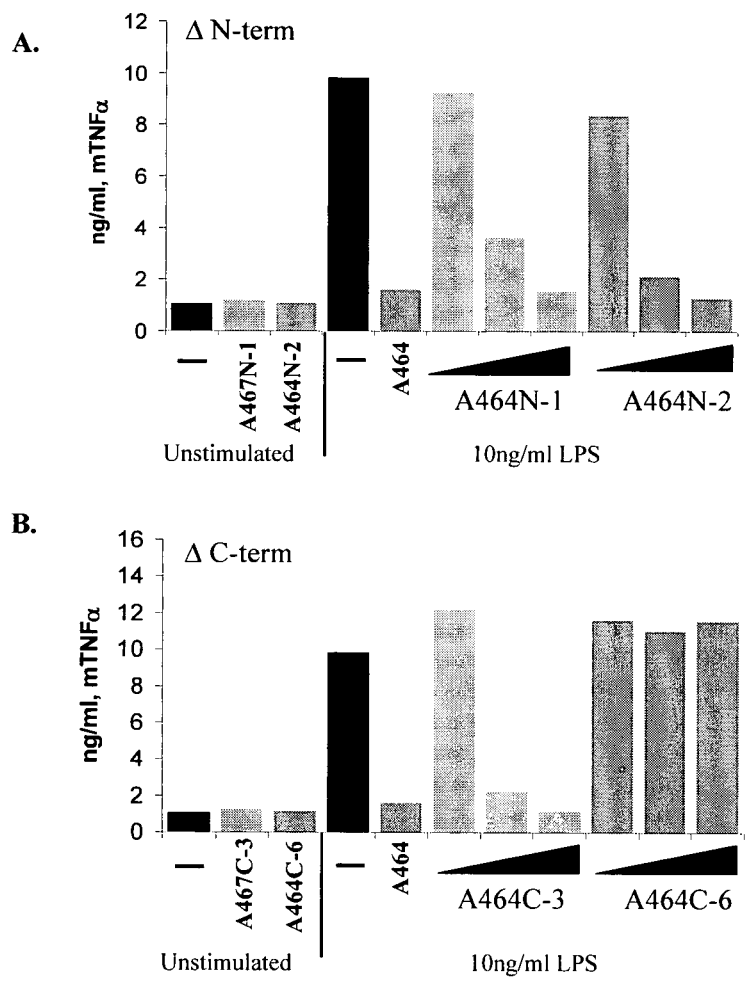
Figure 19:
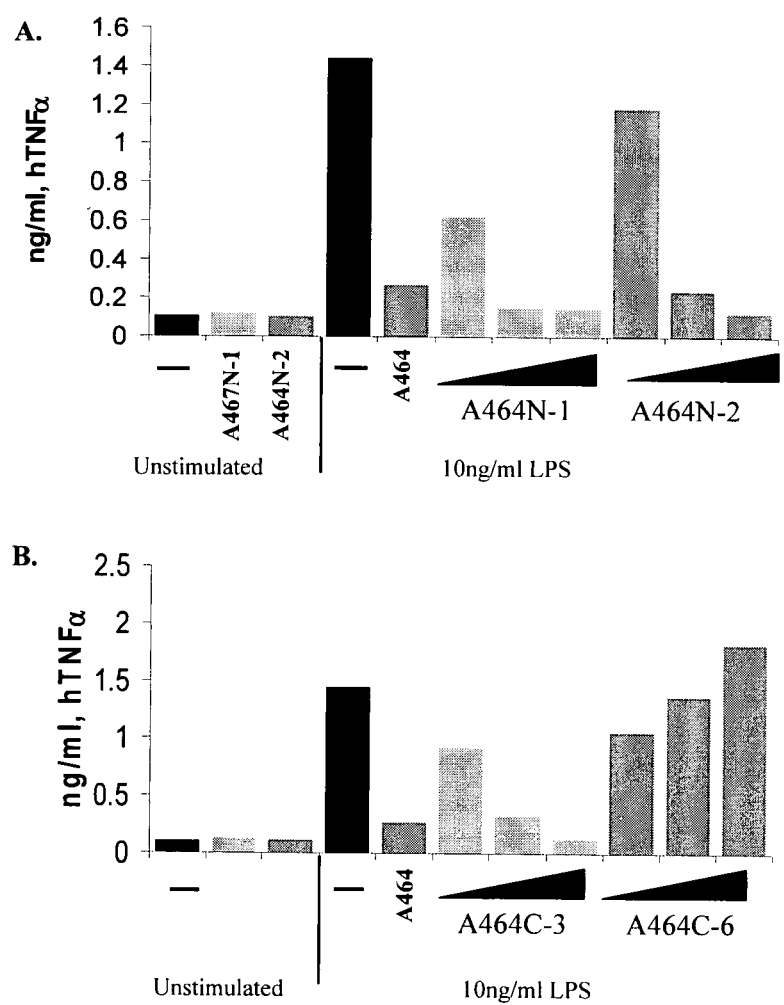
Figure 20:
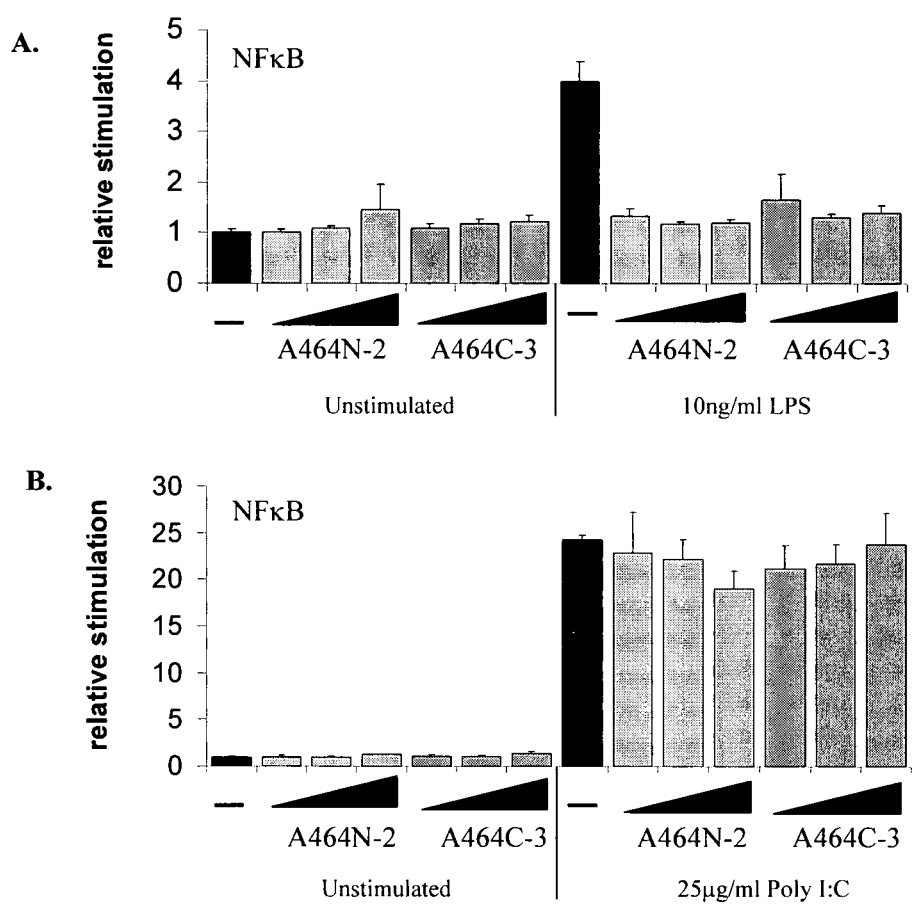

When these peptides were assayed in murine macrophages for the ability to inhibit TLR4, it was found that only the peptide with the deletion of the 6 amino acids from the C-terminus (A464C-6) (SEQ ID No. 43) lost its ability to inhibit LPS-induced TNFα production (FIG. 18). Other deletions appeared to affect the inhibitory potential of the peptide to a minor extent, since they did not inhibit TNFα production at 1 µM but only at 5 µM inhibition (FIG. 18). Importantly, the same results were obtained when primary human cells (PBMCs) were used (FIG. 19). A464N-2 (SEQ ID No. 41) and A464C-3 (SEQ ID No. 42) were then assayed for inhibition of LPS- and Poly(I:C)-induced NFκB activation in HEK293_TLR4 and HEK293_TLR3 cells. Both peptides inhibited LPS-induced NFκB activation completely at 1 µM; at the same time there was no inhibition of TLR3 signalling to NFκB up to 25 µM peptide (FIG. 20). Based on these experiments, the amino acids SFKLIL (SEQ ID NO. 55) were defined as the ones essential for inhibition by A464 (SEQ ID No. 20).

Next an alanine scan of A464 (SEQ ID No. 20) was performed, which involved synthesis of a series of A464 (SEQ ID No. 20) peptides with a substitution of each individual amino acid for alanine. Thus, 10 new peptides were designed with the following sequences (position 9 in A464 (SEQ ID No. 20) is already occupied by an alanine):

```
 1. K1A:     AYSFKLILAEY-9R    (SEQ ID No. 44)

2. Y2A:     KASFKLILAEY-9R    (SEQ ID No. 45)

3. S3A:     KYAFKLILAEY-9R    (SEQ ID No. 46)

4. F4A:     KYSAKLILAEY-9R    (SEQ ID No. 47)

5. K5A:     KYSFALILAEY-9R    (SEQ ID No. 48)

6. L6A:     KYSFKAILAEY-9R    (SEQ ID No. 49)

7. I7A:     KYSFKLALAEY-9R    (SEQ ID No. 50)

8. L8A:     KYSFKLIAAEY-9R    (SEQ ID No. 51)

9. E10A:    KYSFKLILAAY-9R    (SEQ ID No. 52)

10. Y11A:    KYSFKLILAEA-9R    (SEQ ID No. 53)
```

These peptides were assayed for LPS-induced cytokine inhibition in primary human and murine cells, and compared to A464R (SEQ ID No. 20). The parental A464 peptide (SEQ ID No. 20) was used at the concentration of 5 µM as a positive control. The dashed line represents the level of inhibition by parental peptide (SEQ ID No. 20). In the human PBMCs peptides F4A (SEQ ID NO. 47), K5A (SEQ ID NO. 48), L6A (SEQ ID NO. 49), I7A (SEQ ID NO. 50) and E10A (SEQ ID NO. 52) showed reduced inhibitory potential compared to the parental A464 (SEQ ID No. 20) (FIG. 21A). Of note, substitution of the glutamic acid for alanine in E10A (SEQ ID No. 52) made the peptide insoluble, which was the likely reason for the reduced inhibitory effect. In the murine cells only L6A (SEQ ID No. 49) displayed reduced inhibition compared to A464R (SEQ ID No. 20) at 5 µM (FIG. 21B). These results largely correlate with the data obtained using truncated A464 peptides above (SEQ ID No. 44 to 53): namely that (in human cells at least), FKLI (SEQ ID No. 54) is essential for optimal inhibition of TLR4.

Figure 22:
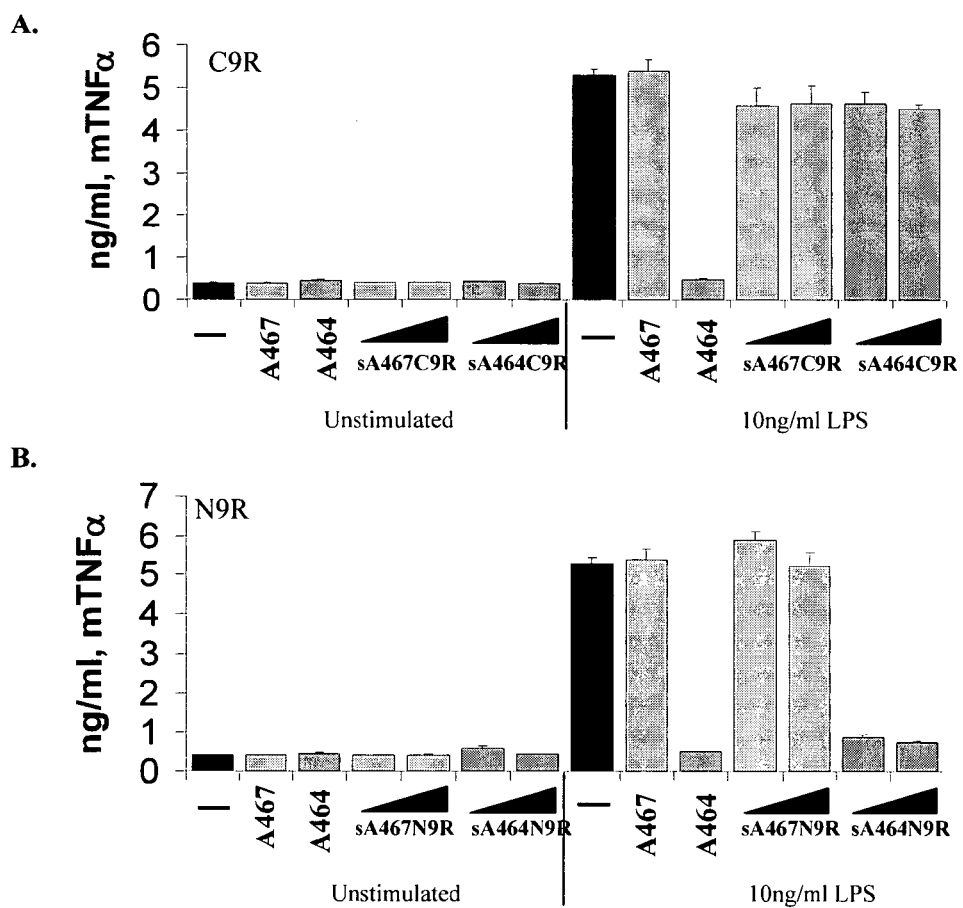

Based on the previous experiments with the deletions and alanine scanning a new shorter version of the A464 peptide (SEQ ID No. 20) was synthesised. This new peptide, called sA464 (SEQ ID No. 55), had the sequence SFKLIL, with the 9R delivery sequence attached to either C- or N-terminus, named accordingly sA464C9R (SEQ ID No. 56) or sA464N9R (SEQ ID No. 57). The control A467 peptide (SEQ ID No. 7) underwent similar modifications and its amino acid sequence became TISGNI (SEQ ID No. 58) with the 9R delivery sequence attached to either N- or C-terminus. sA467C9R (SEQ ID No. 59) or sA467N9R (SEQ ID No. 60). The short A464 (SEQ ID No. 55, 56 and 57) and A467 (SEQ ID No. 58, 59 and 60) peptides were assayed in murine RAW264.7 cells. The peptides were added to the cells at concentrations of 5 and 25 µM. A464 (SEQ ID No. 20) and A467 (SEQ ID No. 23) were used at concentrations of 5 µM as a positive and negative controls. It was found that sA464 (SEQ ID No. 55) was able to inhibit LPS-induced TNFα, but only when the delivery sequence was at the N-terminus (SEQ ID No. 57) (FIG. 22). Further sA464N9R (SEQ ID No. 57) inhibited LPS-induced TNFα production as potently as A464 (SEQ ID No. 20) at 5 µM, demonstrating that the removal of the flanking amino acids did not affect the potency of the peptide to inhibit TLR4 at this concentration in murine cells (FIG. 22). Next the effect of even shorter versions of A464 on TLR4-induced murine TNFα in immortalised murine macrophages was tested. The peptide sA464N9R (SEQ ID NO. 57) was further reduced in size with a deletion of one amino acid from either N-terminus (9R-FKLIL) (SEQ ID NO. 62) or C-terminus (9R-SFKLI) (SEQ ID NO. 63) or both (9R-FKLI) (SEQ ID NO. 64) and one with substitution of Isoleucine (I) to Phenylalanine (F) (9R-SFKLFL) (SEQ ID NO. 65). This showed that 9R-FKLIL retained the ability to inhibit TLR4, while 9R-SFKLI, 9R-FKLI, or 9R-SFKLFL did not (FIG. 23A). None of these peptides were toxic to cells (FIG. 23B).

Thus the sequence FKLIL (SEQ ID No. 68), or a derivative of it such as a peptidomimetic, is a strong candidate for drug development of a specific TLR4 inhibitor with efficacy in human cells.

Example 5

Figure 24:
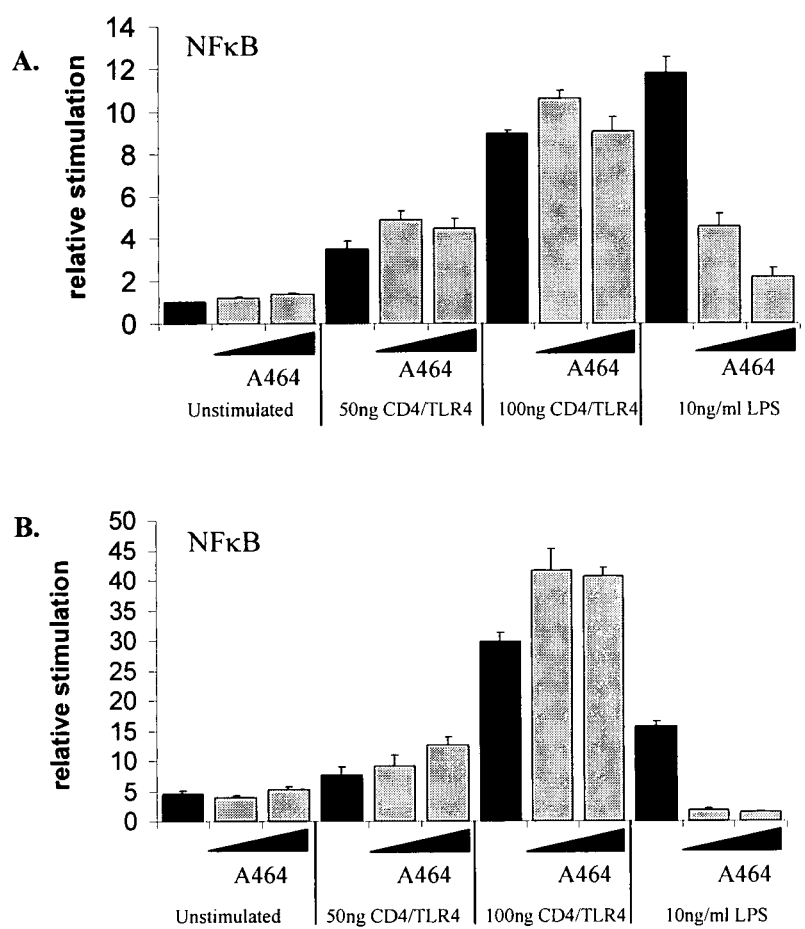

A464 Inhibits TLR4-Dependent Signaling Pathways (Transcription Factors and MAP Kinases) and Interacts with Adaptor Components of the TLR4 Receptor Complex Activation of TLR4 by LPS stimulates activation of the transcription factors NFκB and IRFs, as well as MAPKs, such as p38 and JNK, all of which contribute to altered gene expression. A464 (SEQ ID No. 20) was shown to be capable of inhibiting LPS-induced NFκB activation (FIG. 24). In contrast, NFκB activated by forced dimerisation of TLR4 TIR domains in the absence of LPS (by overexpressing the fusion protein CD4-TLR4) was insensitive to inhibition by A464 (SEQ ID No. 20) (FIG. 24). Thus preformed dimers of TLR4 may be insensitive to A464 (SEQ ID No. 20) and therefore A464 (SEQ ID No. 20) may act to prevent normal TLR4 dimerisation after LPS stimulation.

To further assay activation of NFκB, the degradation of its inhibitor IκBα, an event required for the translocation of the NFκB into the nucleus, was measured. RAW264.7 cells were seeded at $1.5 \times 10^5$ cells/ml in 12 well plates 24 hours before treatment. A467 (SEQ ID No. 23) and A464 (SEQ ID No. 20) were added to the cells at concentrations of 4 µM 1 hour before stimulating with 10 ng/ml LPS for 5, 15, 30 or 60 min. Cells were then harvested and lysed in 1% (v/v) NP-40 Lysis Buffer (see Materials and Methods). The protein concentration in each sample was determined by Bradford assay and samples were diluted accordingly to ensure equal protein loading onto a 12% (w/v) SDS-PAGE gel. Resolved proteins were transferred from the gel onto PVDF membrane by semi-dry transfer and immunoblotted for IκBα. As seen in FIG. 25A, IκBα was present in the control untreated samples and in the unstimulated samples treated with A464 (SEQ ID No. 20) or A467 (SEQ ID No. 23). Stimulation with LPS for 5 min did not significantly affect levels of IκBα in the samples, but after 15 min of LPS treatment IκBα had completely disappeared in the sample treated with A467 (SEQ ID No. 23), and re-appeared again at 60 min treatment, due to rapid re-synthesis of IκB protein (Krappmann and Scheidereit, 1997). However, A464 (SEQ ID No. 20) blocked the degradation of IκBα seen at 15 and 30 min (FIG. 25A). Re-probing for β-actin protein confirmed that the gel was loaded evenly (FIG. 25B). As well as NFκB, A464 (SEQ ID No. 20) also completely inhibited LPS-induced IRF3 activation at 1 µM in HEK293 cells (FIG. 26).

Figure 27:
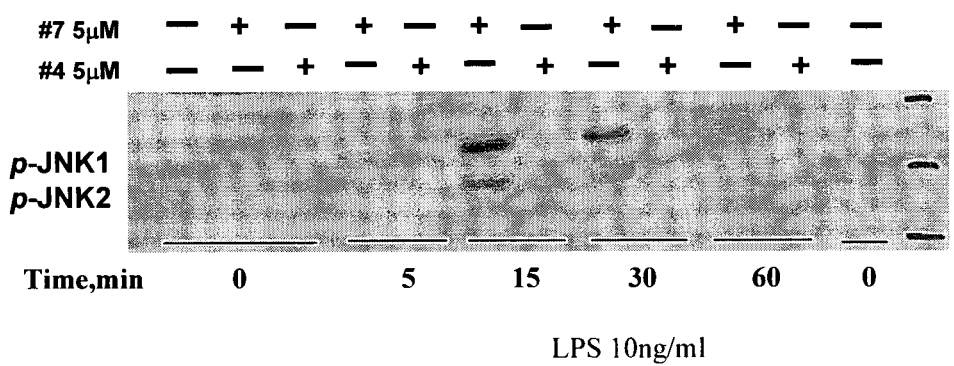
Figure 27:
Figure 27:
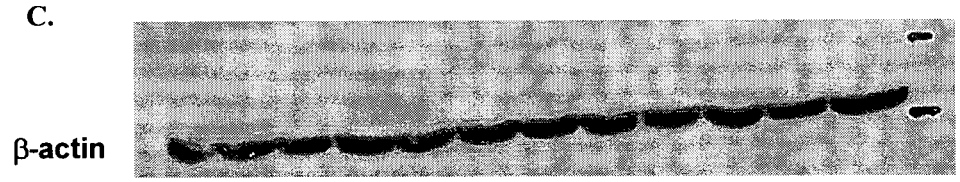

Next, the effect of A464 (SEQ ID No. 20) on MAPK activation was measured by assaying the phosphorylation of p38 and JNK by Western blot. To examine the effect of A464 (SEQ ID No. 20) on the phosphorylation of JNK, RAW264.7 cells were treated with 10 ng/ml LPS for 5-60 min. The membrane was probed with the antibody specific for phospho-JNK protein and the levels of JNK expression in the samples were checked by re-probing the blot for total JNK. As before the protein concentration in the samples was determined by Bradford assay and the accuracy of the loading was confirmed by re-probing the blot for β-actin. As shown in FIG. 27 there was no phosphorylated JNK detected in the unstimulated samples in the presence of A467 (SEQ ID No. 23) or A464 (SEQ ID No. 20), or in the untreated sample. When stimulated with 10 ng/ml for 5 min the phosphorylation of both JNK1 and JNK2 isoforms was detected as two faint bands in the sample treated with A467 (SEQ ID No. 23), which became much stronger at 15 min, and then diminished at 30 and 60 min treatment with LPS. A464 (SEQ ID No. 20) completely inhibited phosphorylation of JNK at all times of the LPS stimulation (FIG. 27A). The levels of the total JNK protein were equal throughout the all samples (FIG. 27B) and the loading was even (FIG. 27C).

The effect of the A464 (SEQ ID No. 20) peptide on p38 MAPK was also examined, and this was of particular interest since p38 has been shown to play an important role in the development of various autoimmune diseases (Kumar et al, 2003). Phosphorylation of p38 was assayed in a manner similar to the experiment described for JNK above. Cells were pretreated with no peptide, or with A467 (SEQ ID No. 23) or A464 (SEQ ID No. 20) prior to stimulation with 10 ng/ml LPS for 5, 30 or 60 min. As in the previous experiment, A464 (SEQ ID No. 20) showed very potent inhibition of LPS-induced p38 phosphorylation at all the time points of LPS stimulation (FIG. 28A). FIG. 28B shows that the expression of total p38 was equal throughout.

Consistent with TLR4 inhibition by A464 (SEQ ID No. 20) and not A467 (SEQ ID NO. 23), a His-tagged version of 464 (without the 9R delivery sequence, SEQ ID NO. 66) but not 467 (SEQ ID NO. 67) was capable of pulling down overexpressed Mal or TRAM from cell lysates (FIG. 29), demonstrating the ability of the peptide 464 to interact with critical adaptor components of the active TLR4 receptor complex.

Example 6

A464 Inhibits LPS-Induced Cytokine Production In Vivo

Figure 16:
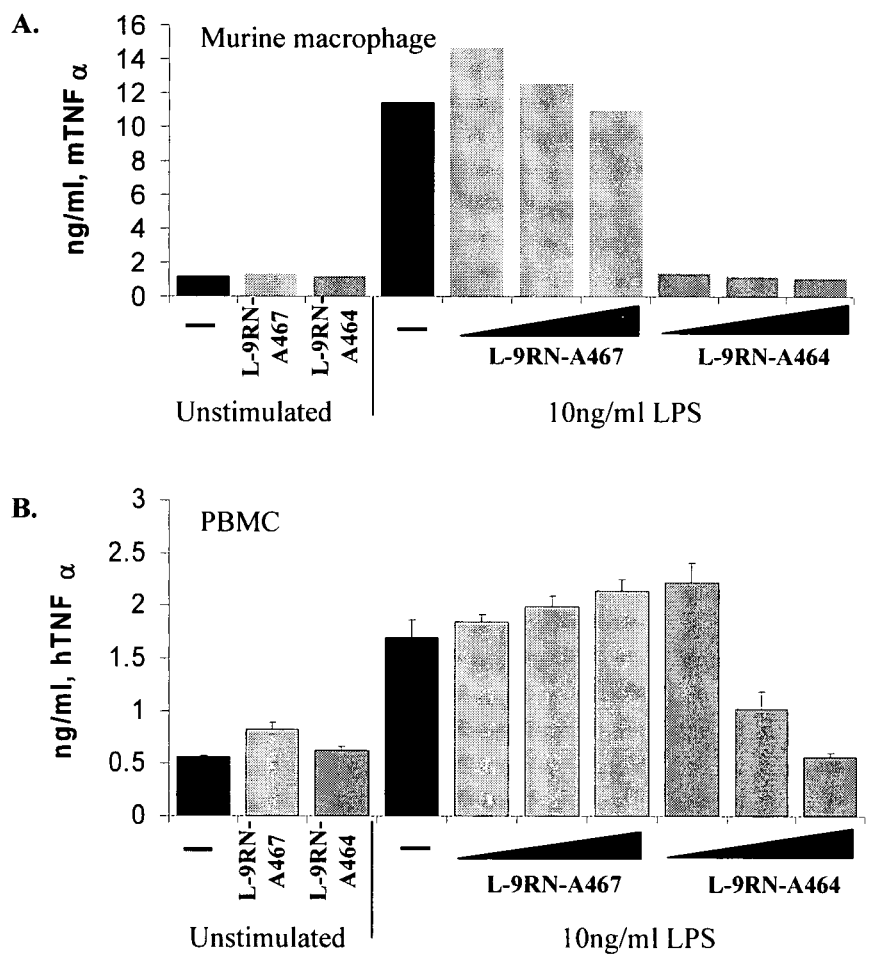
Figure 17:
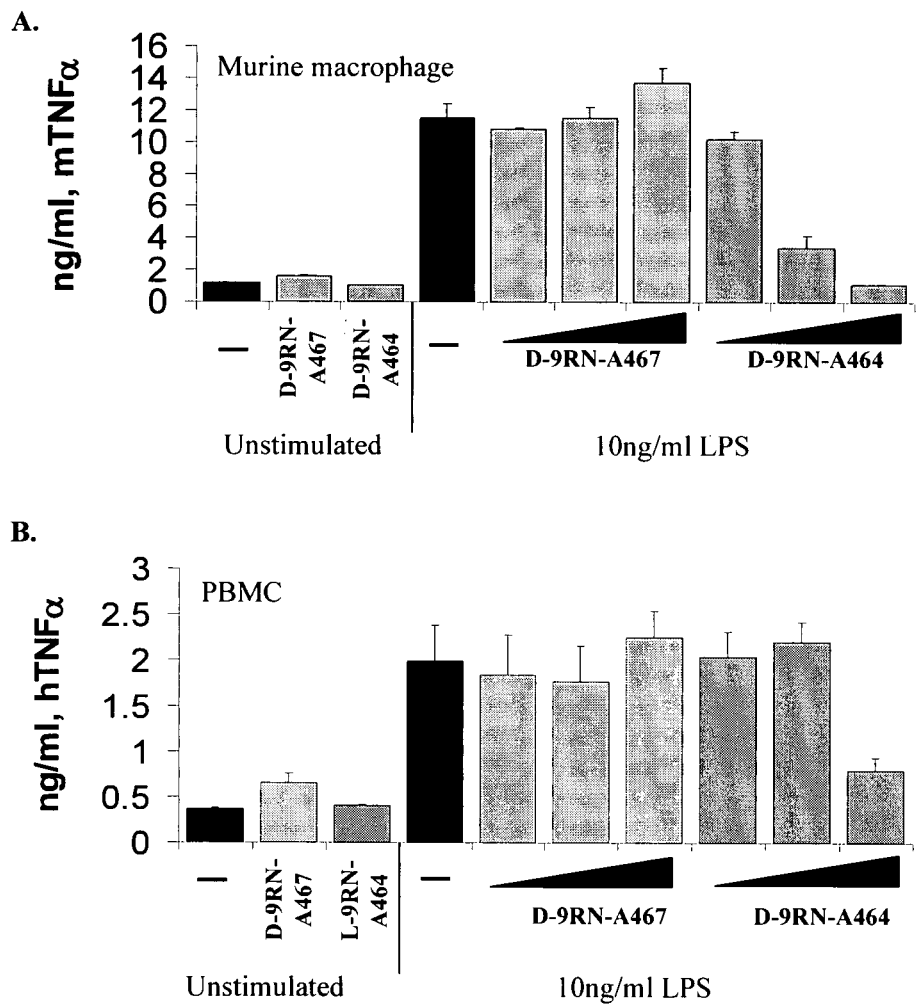

Given that A464 (SEQ ID No. 20) was shown to be a specific TLR4 inhibitor in both human and murine cells, it was of interest to determine whether a related peptide could block LPS responses in vivo. To do this we used a well characterised model of Gram negative sepsis, where mice are injected with LPS and serum cytokines are later analysed by ELISA. For this, the effect of D-9RN-A464 (SEQ ID No. 38) or L-9RN-A464 (SEQ ID No. 38) was compared to L-9RN-A467 (SEQ ID No. 34), since both of these forms of A464 (SEQ ID No. 38) were shown to inhibit TNF production in murine macrophages (FIGS. 16 and 17). Mice were injected i.v. with LPS alone, or with peptide in the presence of LPS. Four hours later serum IL-12p40 concentrations were measured. FIG. 30 shows that both D-9RN-A464 (SEQ ID No. 38) or L-9RN-A464 (SEQ ID No. 38) significantly inhibited LPS-induced IL-12p40 to the extent that mice treated with these peptides displayed levels of IL-12p40 which were not significantly different from the PBS-treated animals. In contrast, although the control peptide L-9RN-A467 (SEQ ID No. 39) did display some inhibition of LPS-induced IL-12p40, it failed to cause as dramatic a reduction as the A464 peptides (FIG. 30). Thus peptides based on the 464 sequence (SEQ ID No. 4) have efficacy in vivo. Thus peptides comprising the 464 sequence (SEQ ID No.4) can inhibit LPS induced proinflammatory IL-12p40 in vivo.

We have shown that A464 (SEQ ID No. 20) inhibits TLR4-induced MAP kinase activation, transcription factor activation and induction of gene expression leading to cytokine and interferon production. Therefore biological responses, including but not limited to MAP kinase activation, transcription factor activation and gene induction, that are inhibited by administration of A464 (SEQ ID No. 20) would be expected to be TLR4-dependent. In this way, in vitro treatment of cells in culture or in vivo treatment of a whole animal with A464 (SEQ ID No. 20), and measuring alterations in biological responses perturbed by the administration of A464 (SEQ ID No. 20) compared to control cells or an untreated animal, can be used as a method to implicate TLR4 in such a biological response. Thus a pathogen- or host-derived substance which induces a biological response in cells or animals could be tested for its ability to activate TLR4 in the presence and absence of A464 (SEQ ID No. 20). In this way compounds or substances that activate TLR4 could be identified and such activators may have use as adjuvants and boosters of an immune response.

LPS signals via TLR4 in order to induce its proinflammatory effects. TLR4 has been implicated in many diseases in man. In autoimmune and inflammatory conditions, endogenous ligands for TLRs have been implicated in their pathogenesis. Although LPS is not be the causative agent of many of these diseases, it follows that potential endogenous ligands that signal via TLR4 could also be blocked using this approach, as 464 (SEQ ID No. 4) peptides block internally.

TLR antagonists hold promise as therapeutics in immune and inflammatory diseases (Kanzler at al, 2007). Further, TLR4 inhibitors warrant particular interest for use in the prophylaxis and/or treatment of severe sepsis, which kills more than 200,000 people in the US each year (Lolis and Bucala, 2003). Sepsis results from uncontrolled activation of LPS/TLR4-induced cytokine induction, and is also amplified by the endogenous TLR4 activators myeloid-related protein-8 (Mrp8) and Mrp14 (Vogl et al, 2007). Mrp8 and Mrp14 are cytosolic proteins in neutrophils and monocytes whose expression are strongly upregulated in inflammatory diseases such as sepsis, rheumatoid arthritis, inflammatory bowel disease and cancer. Mrp8 and Mrp14 are secreted by activated phagocytes and were shown to have a significant role in the pathogenesis of sepsis and to promote lethality in a murine septic shock model. Mrp8 bound directly to the TLR4-MD2 complex to mediate its effects (Vogl et al, 2007). Thus a specific TLR4 inhibitor would be expected to have a significant protective effect if administered to patients at risk of sepsis. Traditionally, attempts to control sepsis have centred on blockage of pro-inflammatory cytokines such as TNFα, a presumed critical effector of LPS/TLR4 toxicity. However TLR4 itself may be a much more effective target for intervention in sepsis, since cellular activation by Mrp8-TLR4 amplifies inflammation (Vogl et al, 2007).

Apart from sepsis, specific inhibition of TLR4 while leaving other pathogen detection pathways intact would have great therapeutic potential in a number of other diseases. Sterile inflammation, which is caused by chemical insult and/or tissue damage rather than by pathogens, may also be mediated by TLR4 in certain contexts such as bleomycin-induced lung inflammation (Kanzler at al, 2007). TLR4 has also been implicated in kidney ischemia/reperfusion injury (IRI), since in a murine model of IRI, mice lacking TLR4 were protected against kidney dysfunction, tubular damage, neutrophil and macrophage accumulation in the kidney, and cytokine production after ischemia (Wu et al, 2007). Further, TLR4 may also have a role in liver IRI (Zhai et al, 2004), in ischemic brain injury (Tang et al, 2007) and in plaque development in atherosclerosis-prone apolipoprotein E-deficient mice (Michelsen et al, 2004). Acute lung injury (ALI), for which treatment options are currently limited and which is a leading cause of death in human H5N1 avian influenza infections, is also TLR4 dependent. ALI is triggered by oxidized phospholipids in the lung which stimulate TLR4 signalling through the TRIF-dependent pathway, leading to cytokine production (Imai et al, 2008).

Given the important role of TLR4 in disease pathogenesis, the development of specific TLR4 inhibitors is important. Viral immunosuppressive proteins have been finely-tuned and honed by evolution to target the host immune system with maximal effectiveness. This is analogous to a 'naturally occurring drug development programme', whereby the protein has already undergone cycles of modification due to natural selection, leading to enhanced inhibitory function. Vaccinia virus has developed effective ways of inhibiting TLRs. Thus peptides derived from such proteins may more potently and specifically target TLR-mediated inflammation compared to current non-specific therapeutic strategies.

The A46 protein, when expressed in human or murine cells, has been shown to inhibit activation of NFκB (which is a critical transcription factor in mediating inflammation) in response to IL-1 (Bowie et al, 2000), to TLR agonists including TLR4 (Stack et al, 2005; Aravalli et al, 2007), and in murine cells to HSV infection (Aravalli et al, 2007). Furthermore, A46 can also block IL-1 and TLR-mediated MAP kinase and IRF activation in human cells (Stack et al, 2005). A46 works by binding to TIR domains in host proteins, and has been shown to be able to associate with TLR4, IL-1RAcP, MyD88, Mal, TRIF and TRAM, which explains how A46 can inhibit multiple TLR pathways (Stack et al, 2005). In contrast, the effects of the A464 peptide (SEQ ID No. 20) are specific to inhibition of TLR4 signalling. A46 protein inhibits TLRs by interacting with TIR domains, it is likely that the A464 peptide (SEQ ID No. 20) acts in a similar manner to prevent critical TIR-TIR interactions in TLR4 signalling.

TLR4 signalling involves five distinct TIR-domain containing proteins: TLR4, Mal, MyD88, TRAM and TRIF. Given that A464 (SEQ ID No. 20) did not inhibit TLRs which use TRIF (TLR3) or MyD88 (TLR9) it is unlikely that the peptide targets either of these two adaptors directly. Rather it is likely that A464 (SEQ ID No. 20) targets TLR4, Mal or TRAM in order to disrupt TLR4-TLR4 and/or TLR4-TRAM and/or TLR4-Mal TIR interactions. Consistent with this, His-tagged A464 (SEQ ID NO. 66) was capable of interacting with overexpressed Mal or TRAM when added to cell lysates.

It is likely that A464 is binding to a novel site on Mal or TRAM that is essential for TLR4 function. Therefore the A464 or related peptides may be useful in screening for novel inhibitors of TLR4 or Mal or TRAM. Assuming that A464 binds to a site on Mal or TRAM essential for TLR4 function, a screen could be established to assay for small molecules that would bind to this site and thus displace A464. For example, FITC-labelled A464 displacement from recombinant TRAM or recombinant Mal could be measured as an assay of small molecule binding to said site.

The invention is not limited to the embodiment hereinbefore described, with reference to the accompanying drawings, which may be varied in construction and detail.

REFERENCES

Akira S, Uematsu S, Takeuchi O. 2006. Pathogen recognition and innate immunity. Cell 124, 783-801.

Ansel's Pharmaceutical Dosage Forms and Drug Delivery Systems; Allen, L. V., Papovich N. G and Ansel, H. C. 2005 8$^{th}$ Edition ISBN 0-781746-12-4, pp185-505; 653-671.

Aravalli et al., 2007. Inhibition of Toll-like Receptor Signaling in Primary Murine Microglia. *J Neuroimmune Pharmacol* doi 10.1007/s11481-007-9097-8

Bowie et al., 2000. A46R and A52R from vaccinia virus are antagonists of host IL-1 and Toll-like receptor signaling. *Proc Natl Acad Sci USA* 97, 10162-10167

De Filippo et al., 2008. Neutrophil Chemokines KC and Macrophage-Inflammatory Protein-2 Are Newly Synthesized by Tissue Macrophages Using Distinct TLR Signaling Pathways. *J Immunol* 180, 4308-4315.

Domart-Coulon et al., 2000. Cytotoxicity assessment of antibiofouling compounds and by-products in marine bivalve cell cultures. Toxicol In Vitro 14, 245-251.

Gorden et al., 2005. Synthetic TLR agonists reveal functional differences between human TLR7 and TLR8. *J Immunol* 174, 1259-1268.

Harte, M T et al, 2003. The poxvirus protein A52R targets Toll-like receptor signalling complexes to suppress host defence. *J. Exp. Med.* 197, 343-351.

Henneke et al., 2002. Cellular Activation, Phagocytosis, and Bactericidal Activity Against Group B Streptococcus Involve Parallel Myeloid Differentiation Factor 88-Dependent and Independent Signaling Pathways. *J Immunol* 169, 3970-3977.

Imai et al., 2008. Identification of Oxidative Stress and Toll-like Receptor 4 Signaling as a Key Pathway of Acute Lung Injury. *Cell* 133, 235-249.

Kanzler et al., 2007. Therapeutic targeting of innate immunity with Toll-like receptor agonists and antagonists. *Nat Medicine* 13, 552-559.

Keating, S E, Maloney, G M, Moran, E M, Bowie, A G, 2007. IRAK-2 participates in multiple toll-like receptor signalling pathways to NF☐B via activation of TRAF6 ubiquitination. *J. Biol. Chem.* 282, 33435-33443.

Krappmann and Scheidereit, 1997. Regulation of NF-kappa B activity by I kappa B alpha and I kappa B beta stability. *Immunobiology* 198, 3-13.

Kumar et al., 2003. p38 MAP kinases: key signalling molecules as therapeutic targets for inflammatory diseases. *Nat Rev Drug Discov* 2, 717-726.

Langer et al, *J. Biomed. Mater. Res.* 15: 167-277, 1981

Langer, *Chem. Tech.* 12:98-105, 1982

Latz et al., 2004. TLR9 signals after translocating from the ER to CpG DNA in the lysosome. *Nat Immunol* 5, 190-198.

Loiarro et al., 2005. Peptide-mediated Interference of TIR Domain Dimerization in MyD88 Inhibits Interleukin-1-dependent Activation of NF-κB. *J. Biol. Chem.* 280, 15809-15814.

Lolis and Bucala, 2003. Therapeutic approaches to severe sepsis *Nat Rev Drug Discov* 2, 635-645.

McCoy et al. 2005. Identification of a Peptide Derived from Vaccinia Virus A52R Protein That Inhibits Cytokine Secretion in Response to TLR-Dependent Signaling and Reduces In Vivo Bacterial-Induced Inflammation. *J. Immunol.* 174, 3006-3014.

Michelsen et al., 2004. Lack of Toll-like receptor 4 or myeloid differentiation factor 88 reduces atherosclerosis and alters plaque phenotype in mice deficient in apolipoprotein E *Proc Natl Acad Sci USA* 101, 10679-10684.

Murriel & Dowdy, 2006. Influence of protein transduction domains on intracellular delivery of macromolecules. *Expert Opin. Drug Deliv.* 3, 739-746.

O'Neill, L A J, 2006. Targeting signal transduction as a strategy to treat inflammatory diseases. *Nature Rev. Drug Disc.* 7, 549-563.

O'Neill, L A J, Bowie, A G, 2007. The family of five: TIR-domain-containing adaptors in Toll-like receptor signalling. *Nat. Reviews Immunol.* 7, 353-364.

Schwarze et al., 1999. In vivo protein transduction: delivery of a biologically active protein into the mouse. *Science* 285, 1569-1572.

Sidman et al, *Biopolymers* 22(1): 547-556, 1985

Stack, J et al, 2005. Vaccinia virus protein A46R targets multiple Toll-like-interleukin-1 receptor adaptors and contributes to virulence. *J Exp. Med.* 201, 1007-1018

Takashiba et al., 1999. Differentiation of monocytes to macrophages primes cells for lipopolysaccharide stimulation via accumulation of cytoplasmic nuclear factor kappaB. *Infect Immun* 67, 5573-5578.

Tang et al., 2007. Pivotal role for neuronal Toll-like receptors in ischemic brain injury and functional deficits. *Proc Natl Acad Sci USA* 104, 13798-13803.

Toshchakov et al., 2005. Differential Involvement of BB Loops of Toll-IL-1 Resistance (TIR) Domain-Containing Adapter Proteins in TLR4-versus TLR2-Mediated Signal Transduction. *J. Immunol* 175, 494-500.

Toshchakov et al., 2007. Cutting Edge: Differential Inhibition of TLR Signaling Pathways by Cell-Permeable Peptides Representing BB Loops of TLRs. *J. Immunol* 178, 2655-2660.

Toshchakov and Vogel, 2007. Cell-penetrating TIR BB loop decoy peptides a novel class of TLR signaling inhibitors and a tool to study topology of TIR-TIR interactions. *Expert Opin. Biol. Ther.* 7, 1035-1050.

Tsung et al., 2007. A novel inhibitory peptide of toll-like receptor signaling limits lipopolysaccharide-induced production of Inflammatory mediators and enhances survival in mice. *Shock* 27, 364-369

Vogl et al., 2007. Mrp8 and Mrp14 are endogenous activators of Toll-like receptor 4, promoting lethal, endotoxin-induced shock. *Nat Medicine* 13, 1042-1049

Wender et al., 2000. The design, synthesis, and evaluation of molecules that enable or enhance cellular uptake: peptoid molecular transporters. *Proc Natl Acad Sci USA* 97, 13003-13008.

Wu et al., 2007. TLR4 activation mediates kidney ischemia/reperfusion injury. *J. Clin Invest* 117, 2847-2859.

Zhai et al., 2004. Cutting Edge: TLR4 Activation Mediates Liver Ischemia/Reperfusion Inflammatory Response via IFN Regulatory Factor 3-Dependent MyD88-Independent Pathway. *J Immunol* 15, 7115-7119.

U.S. Pat. No. 3,773,919

EP-A-0058481

The invention claimed is:

1. A peptide for inhibiting Toll-like receptor 4 (TLR4) signalling wherein said peptide consists of the amino acid sequence of SEQ ID NO:4.

2. The peptide as claimed in claim 1 wherein the amino acid sequence is in the L-form.

3. The peptide as claimed in claim 1 wherein the amino acid sequence is in the D-form.

4. The peptide as claimed in claim 1 comprising a delivery sequence.

5. The peptide as claimed in claim 4 wherein the delivery sequence is a cationic peptide.

6. The peptide as claimed in claim 4 wherein the delivery sequence is between 8 and 16 amino acids in length.

7. The peptide as claimed in claim 4 wherein the delivery sequence comprises the amino acid sequence of SEQ ID NO:33, SEQ ID NO:34, or SEQ ID NO:35.

8. The peptide as claimed in claim 4 wherein the delivery sequence is attached to the C terminus of the peptide.

9. The peptide as claimed in claim 8 wherein said peptide consists of the amino acid sequence of SEQ ID NO:20.

* * * * *